United States Patent
Zeng et al.

(10) Patent No.: US 8,652,656 B2
(45) Date of Patent: Feb. 18, 2014

(54) TRIPHENYLENE SILANE HOSTS

(75) Inventors: Lichang Zeng, Lawrenceville, NJ (US);
Alexey Dyatkin, Ambler, PA (US);
Gregg Kottas, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 139 days.

(21) Appl. No.: 13/295,660

(22) Filed: Nov. 14, 2011

(65) Prior Publication Data

US 2013/0119353 A1    May 16, 2013

(51) Int. Cl.
*H01L 51/50* (2006.01)

(52) U.S. Cl.
USPC ........... 428/690; 428/917; 313/504; 313/505; 313/506; 257/40; 257/E51.05; 257/E51.026; 257/E51.032; 548/418; 548/440

(58) Field of Classification Search
USPC ............ 428/690, 917; 313/504, 505, 506; 257/40, E51.05, E51.026, E51.032; 548/418, 440
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |

(Continued)

FOREIGN PATENT DOCUMENTS

EP  0650955  5/1995
EP  1725079  11/2006

(Continued)

OTHER PUBLICATIONS

Kuwabara, Yoshiyuki et al., "Thermally Stable Multilayered Organic Electroluminescent Devices Using Novel Starburst Molecules, 4,4',4"-Tri(*N*-carbazolyl)triphenylamine (TCTA) and 4,4',4"-Tris(3-methylphenylphenyl-amino)triphenylamine (*m*-MTDATA), as Hole-Transport Materials," *Adv. Mater.*, 6(9):677-679 (1994).

(Continued)

*Primary Examiner* — Gregory Clark
(74) *Attorney, Agent, or Firm* — Duane Morris LLP

(57) ABSTRACT

Novel aryl silicon and aryl germanium host materials, and in particular host materials containing triphenylene and pyrene fragments, are described. These compounds improve OLED device performance when used as hosts in the emissive layer of the OLED.

23 Claims, 5 Drawing Sheets

(56) References Cited

U.S. PATENT DOCUMENTS

| | | |
|---|---|---|
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | | | |
|---|---|---|---|---|
| EP | 2034 538 | * | 3/2009 | ............ H01L 51/50 |
| EP | 2034538 | | 3/2009 | |
| JP | 200511610 | | 1/2005 | |
| JP | 2005071983 | | 3/2005 | |
| JP | 2007123392 | | 5/2007 | |
| JP | 2007254297 | | 10/2007 | |
| JP | 2008074939 | | 10/2009 | |
| KR | 2009073928 | | 7/2009 | |
| KR | 2011043270 | | 4/2011 | |
| WO | WO 0139234 | | 5/2001 | |
| WO | WO 0202714 | | 1/2002 | |
| WO | WO 0215645 | | 2/2002 | |
| WO | WO 03040257 | | 5/2003 | |
| WO | WO 03060956 | | 7/2003 | |
| WO | WO 2004093207 | | 10/2004 | |
| WO | WO 2004107822 | | 12/2004 | |
| WO | WO 2005014551 | | 2/2005 | |
| WO | WO 2005019373 | | 3/2005 | |
| WO | WO 2005030900 | | 4/2005 | |
| WO | WO 2005089025 | | 8/2005 | |
| WO | WO 2005123873 | | 12/2005 | |
| WO | WO 2006009024 | | 1/2006 | |
| WO | WO 2006056418 | | 6/2006 | |
| WO | WO 2006072002 | | 7/2006 | |
| WO | WO 2006082742 | | 8/2006 | |
| WO | WO 2006098120 | | 9/2006 | |
| WO | WO 2006100298 | | 9/2006 | |
| WO | WO 2006103874 | | 10/2006 | |
| WO | WO 2006114966 | | 11/2006 | |
| WO | WO 2006132173 | | 12/2006 | |
| WO | WO 2007002683 | | 1/2007 | |
| WO | WO 2007004380 | | 1/2007 | |
| WO | WO 2007063754 | | 6/2007 | |
| WO | WO 2007063796 | | 6/2007 | |
| WO | WO 2008101842 | | 8/2008 | |
| WO | WO 2008132085 | | 11/2008 | |
| WO | WO 2009000673 | | 12/2008 | |
| WO | WO 2009003898 | | 1/2009 | |
| WO | WO 2009008311 | | 1/2009 | |
| WO | WO 2009018009 | | 2/2009 | |
| WO | WO 2009050290 | | 4/2009 | |
| WO | WO 2008056746 | | 5/2009 | |
| WO | WO 2009021126 | | 5/2009 | |
| WO | WO 2009062578 | | 5/2009 | |
| WO | WO 2009063833 | | 5/2009 | |
| WO | WO 2009066778 | | 5/2009 | |
| WO | WO 2009066779 | | 5/2009 | |
| WO | WO 2009086028 | | 7/2009 | |
| WO | WO 2009100991 | | 8/2009 | |
| WO | WO 2010 126234 | * | 11/2010 | ............ H01L 51/50 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

(56) References Cited

OTHER PUBLICATIONS

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NΛCΛN-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko at al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko,"1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kidd, Junji et al., 1,2,4-Triazole Derivative as an Electron Transport Layer in Organic Electroluminescent Devices,' *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing at al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 3, 4-6 (1999).

\* cited by examiner

Formula I

TRIPHENYLENE SILANE HOSTS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds suitable for use as host materials in OLEDs, specifically compounds comprising arylgermane and arylsilane groups.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the following structure:

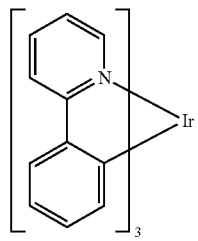

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the Formula I is provided:

Formula I

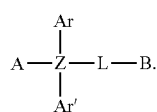

In the compound of Formula I, Ar and Ar' are independently selected from the group consisting of phenyl, biphenyl, naphthalene, dibenzothiophene and dibenzofuran, which are optionally further substituted. Z is selected from Si and Ge. L is a single bond or comprises an aryl or heteroaryl group having from 5-20 carbon atoms, which is optionally further substituted. A is a group directly bonded to Z and is selected from the group consisting of triphenylene, tetraphenylene, pyrene, naphthalene, fluoranthene, chrysene, phenanthrene, azatriphenylene, azatetraphenylene, azapyrene, azanaphthalene, azafluoranthene, azachrysene, azaphenanthrene, and combinations thereof, which are optionally further substituted with one or more groups selected from the group consisting of hydrogen, deuterium, halide, alkyl, cycloalkyl, heteroalkyl, arylalkyl, aryl, aryloxy, and combinations thereof.

B contains a group selected from the group consisting of carbazole, dibenzofuran, dibenzothiophene, dibenzoselenophene, aza-carbazole, aza-dibenzofuran, aza-dibenzothiophene, azadibenzoselenophene, and combinations thereof, which are optionally further substituted with one or more groups selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole, dibenzofuran, dibenzothiophene, dibenzoselenophene, aza-carbazole, aza-dibenzofuran, azadibenzothiophene or azadibenzoselenophene group.

In one aspect, A is

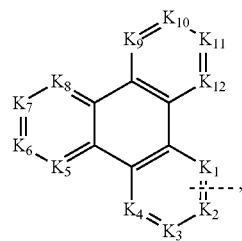

wherein $K_1$ to $K_{12}$ are independently selected from N and C—R', and wherein R' is selected from the group consisting of hydrogen, deuterium, halide, alkyl, cycloalkyl, heteroalkyl, arylalkyl, aryl, aryloxy, and combinations thereof.

In one aspect, B is selected from the group consisting of:

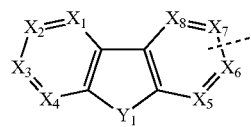

-continued

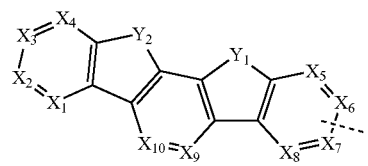

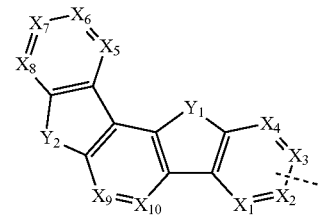

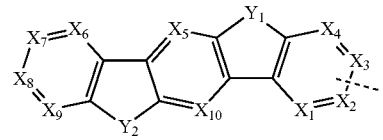

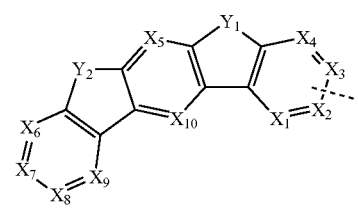

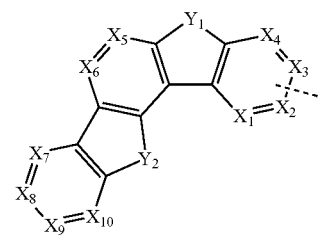

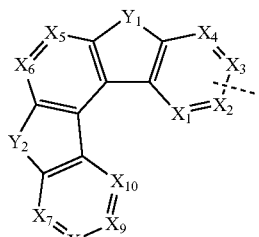
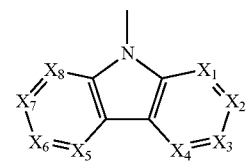

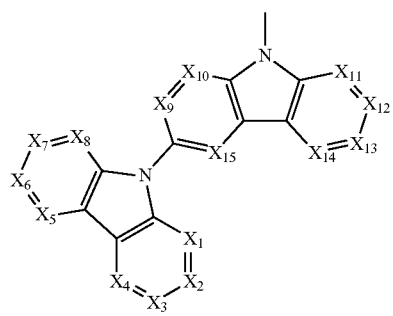

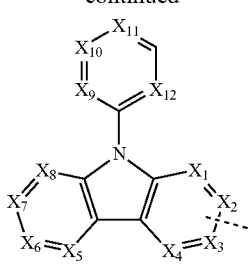

wherein $X_1$-$X_{15}$ are independently selected from the group consisting of N and C—R", wherein R" is selected from a group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $Y_1$ and $Y_2$ are independently selected from the group consisting of O, S, and Se.

In one aspect, A is selected from the group consisting of:

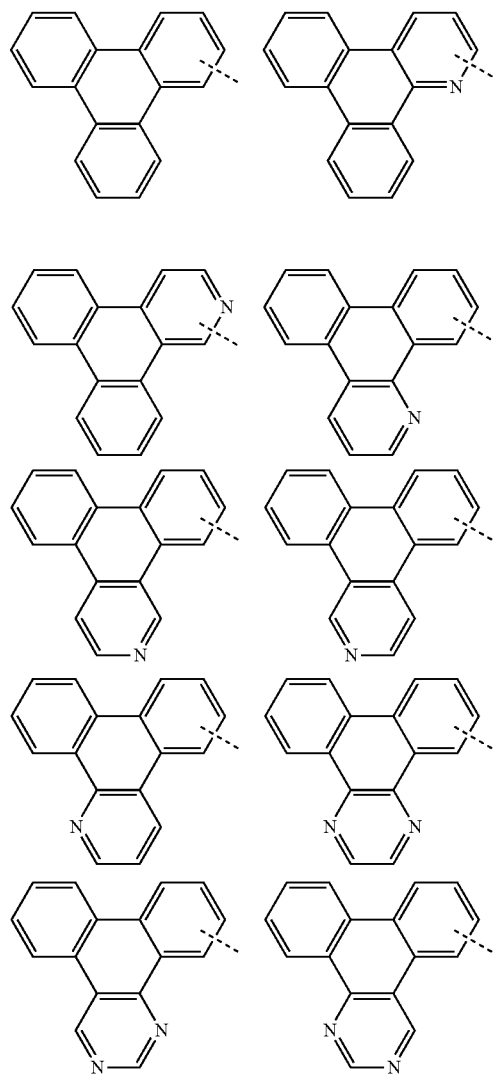

In one aspect, A is selected from the group consisting of:

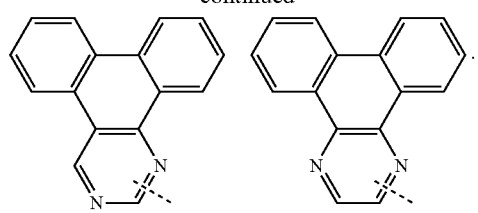

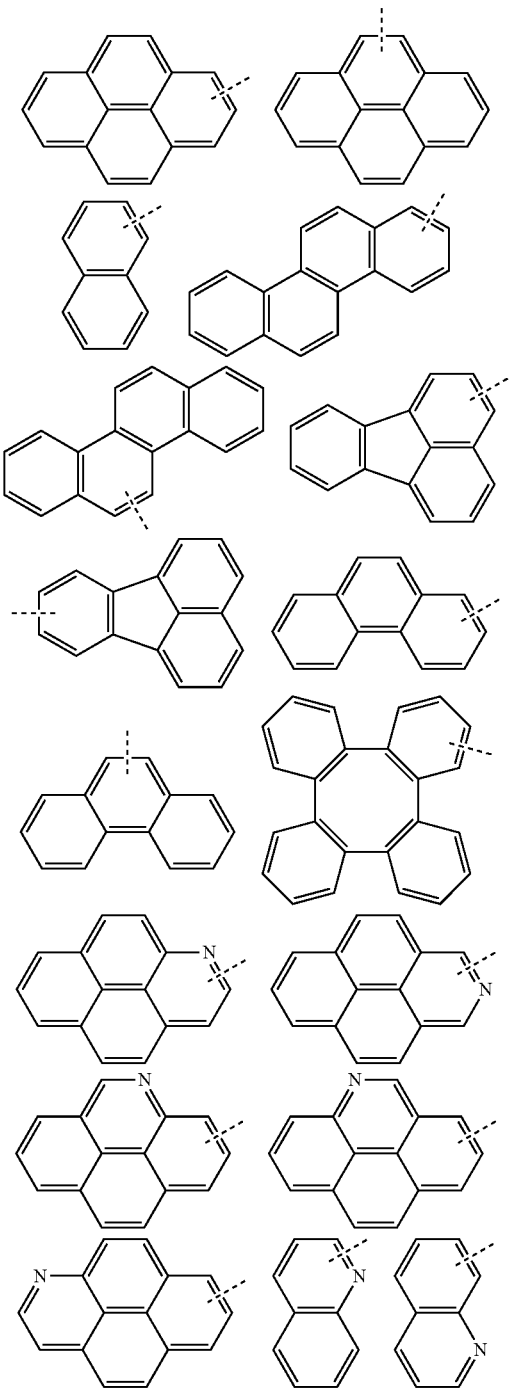

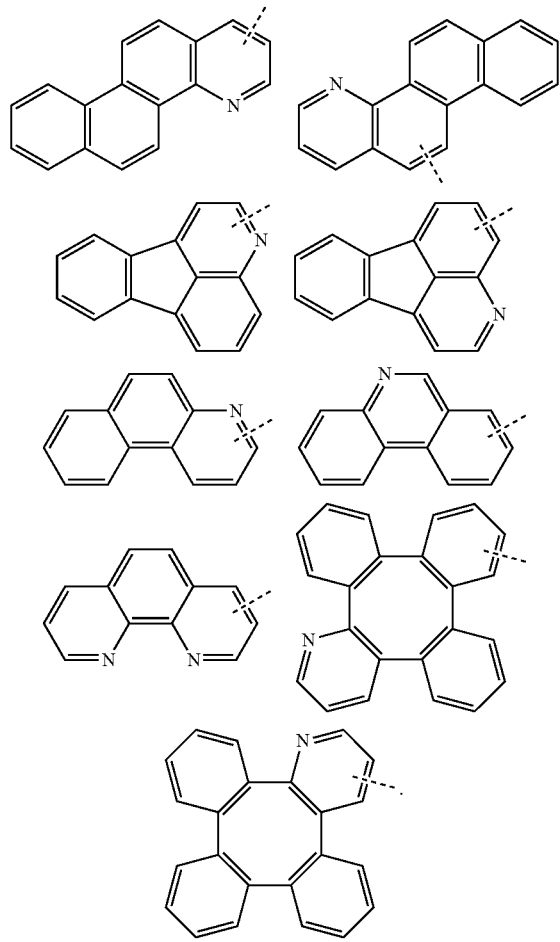
In one aspect, B is selected from the group consisting of:
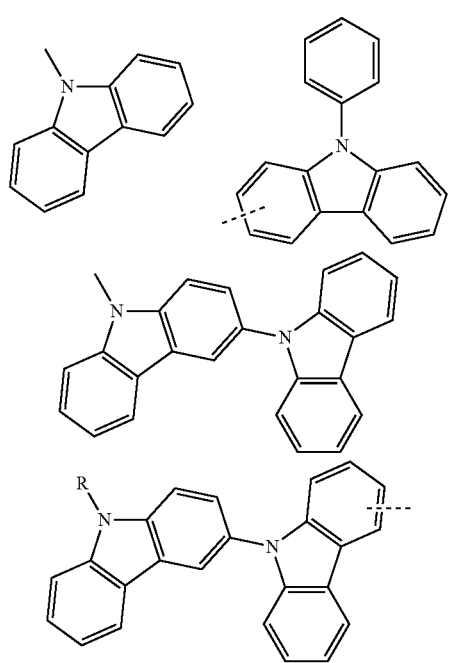
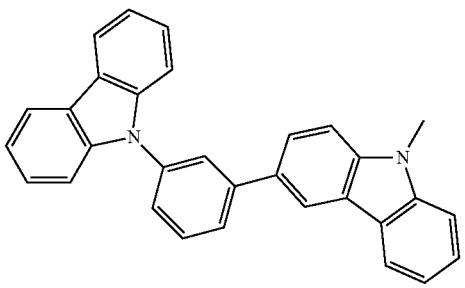
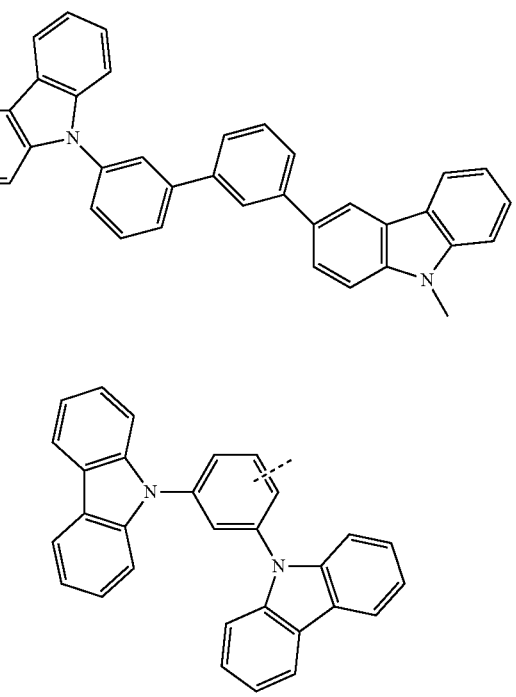
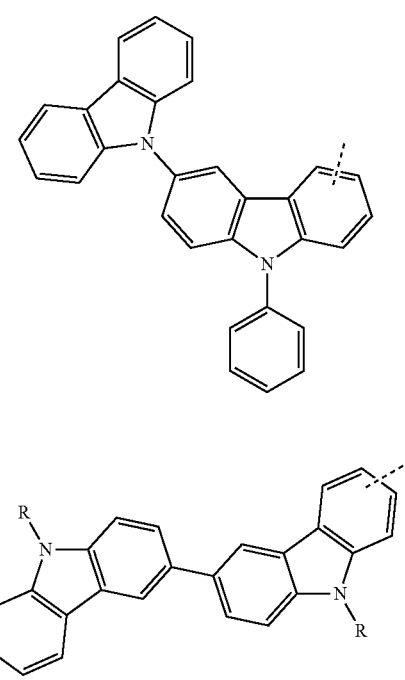

-continued
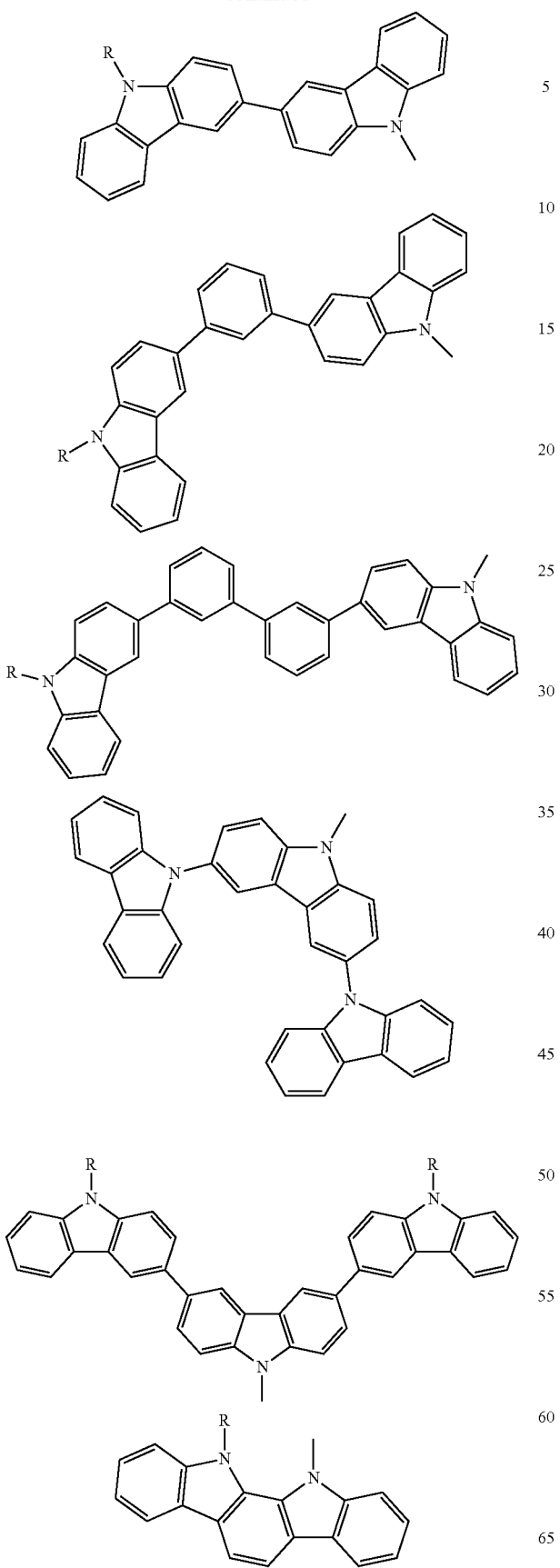
-continued
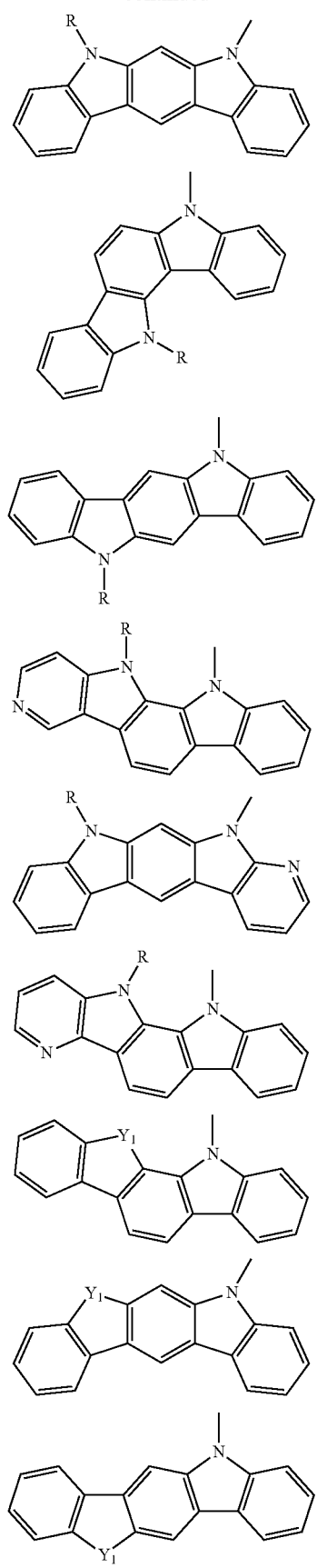

-continued

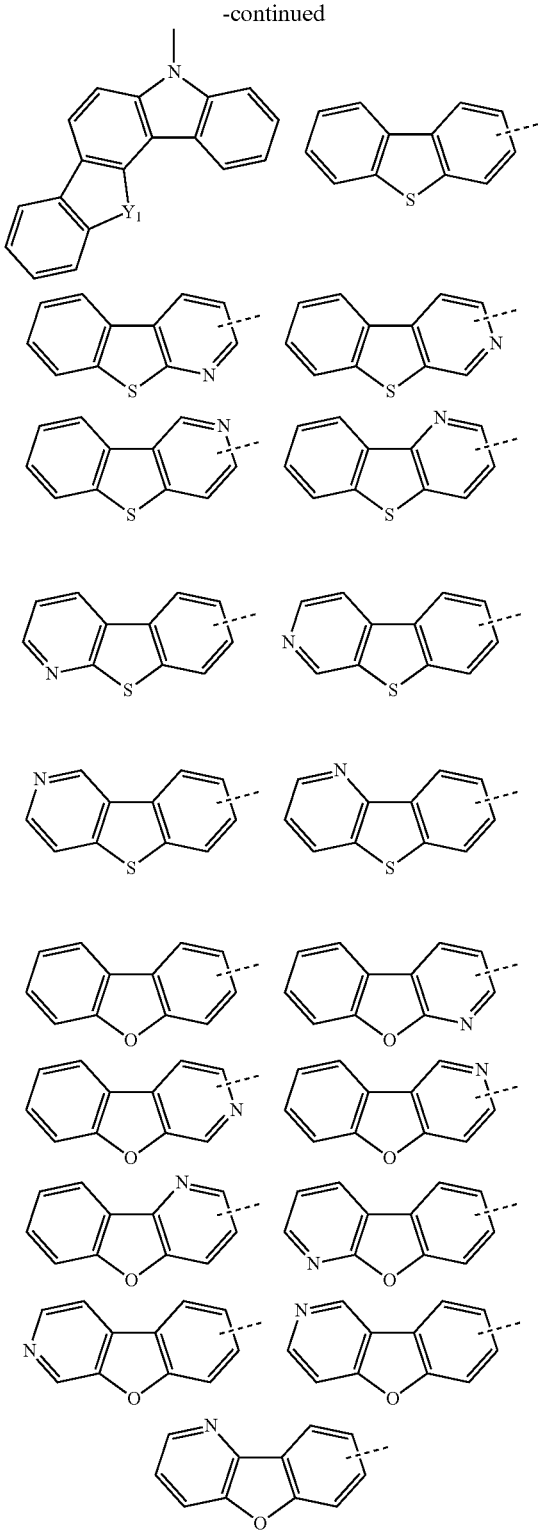

wherein Y₁ is selected from the group consisting of O, S, and Se, wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

In one aspect, L is independently selected from the group consisting of:

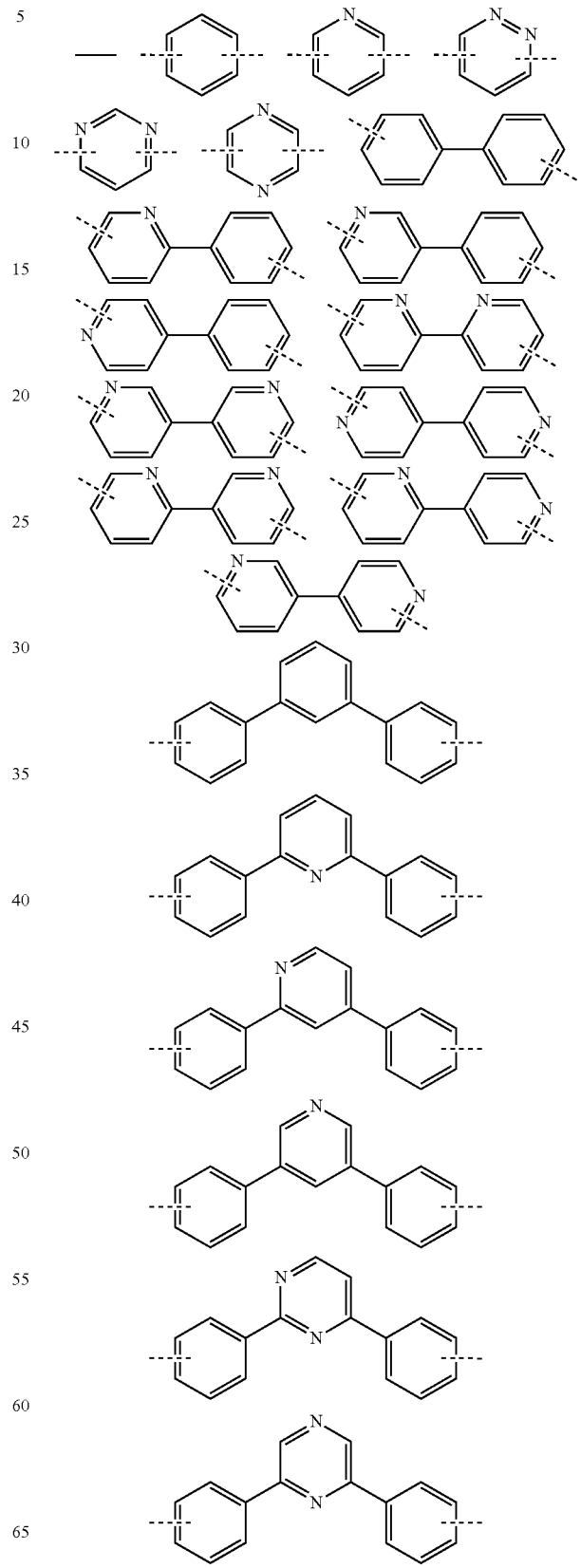

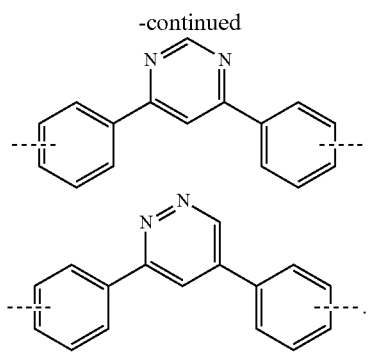

In one aspect, A is tripheynylene. In another aspect, A is pyrene. In one aspect, Ar and Ar' are phenyl. In one aspect, L is phenyl.

In one aspect, the compound is selected from the group consisting of Compound 1-Compound 35.

In one aspect, a first device is provided. The first device comprises an organic light-emitting device, which further comprises an anode, a cathode, and an organic layer, disposed between the anode and the cathode, comprising a compound having the Formula I:

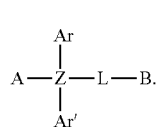

Formula I

In the compound of Formula I, Ar and Ar' are independently selected from the group consisting of phenyl, biphenyl, naphthalene, dibenzothiophene and dibenzofuran, which are optionally further substituted. Z is selected from Si and Ge. L is a single bond or comprises an aryl or heteroaryl group having from 5-20 carbon atoms, which is optionally further substituted. A is a group directly bonded to Z and is selected from the group consisting of triphenylene, tetraphenylene, pyrene, naphthalene, fluoranthene, chrysene, phenanthrene, azatriphenylene, azatetraphenylene, azapyrene, azanaphthalene, azafluoranthene, azachrysene, azaphenanthrene, and combinations thereof, which are optionally further substituted with one or more groups selected from the group consisting of hydrogen, deuterium, halide, alkyl, cycloalkyl, heteroalkyl, arylalkyl, aryl, aryloxy, and combinations thereof.

B contains a group selected from the group consisting of carbazole, dibenzofuran, dibenzothiophene, dibenzoselenophene, aza-carbazole, aza-dibenzofuran, aza-dibenzothiophene, azadibenzoselenophene, and combinations thereof, which are optionally further substituted with one or more groups selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole, dibenzofuran, dibenzothiophene, dibenzoselenophene, aza-carbazole, aza-dibenzofuran, azadibenzothiophene or azadibenzoselenophene group.

In one aspect, the organic layer is an emissive layer and the compound of Formula I is a host. In another aspect, the organic layer further comprises an emissive dopant.

In one aspect, the emissive dopant is a transition metal complex having at least one ligand selected from the group consisting of:

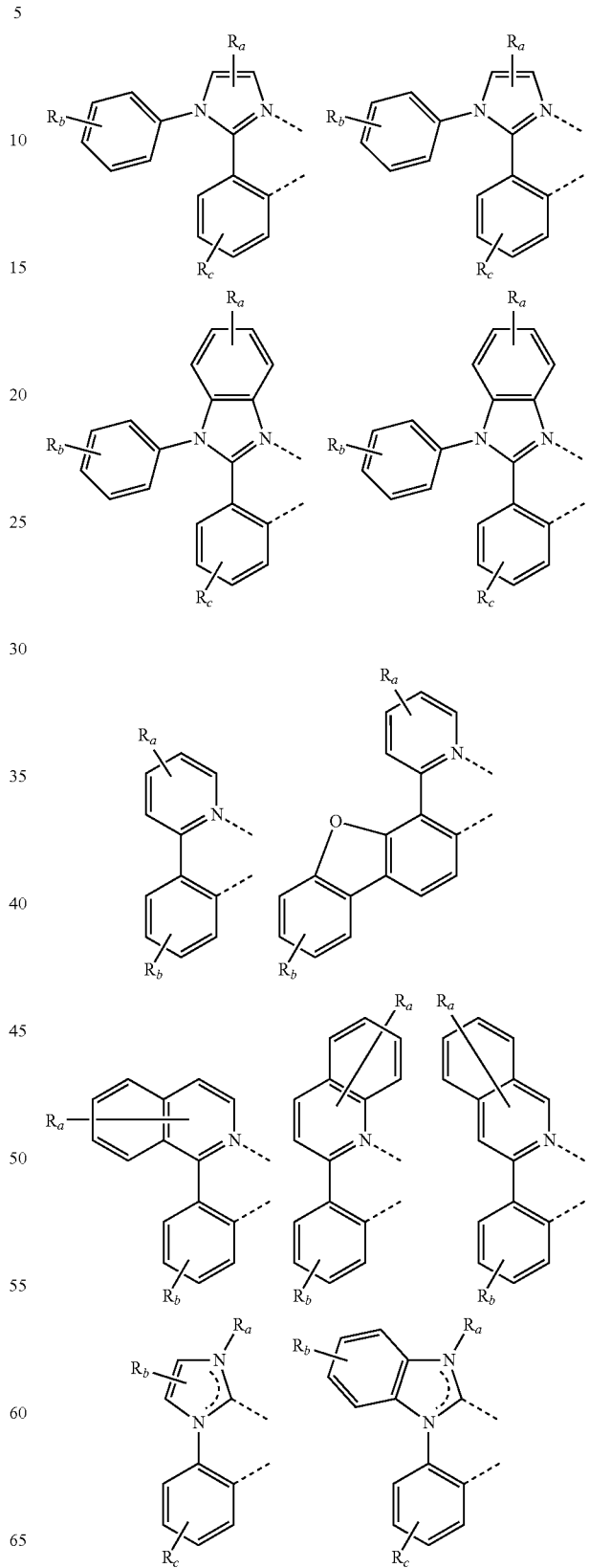

-continued

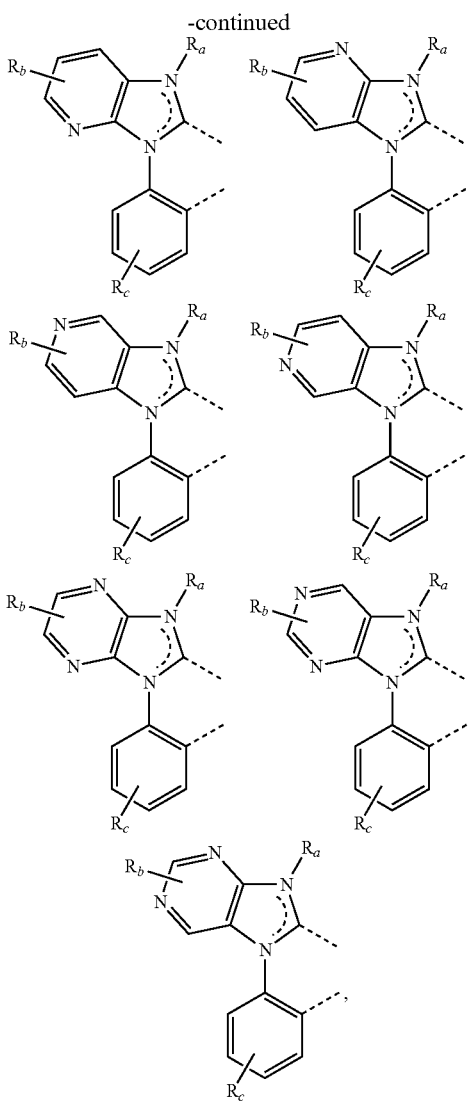

wherein $R_a$, $R_b$, and $R_c$ may represent mono, di, tri or tetra substitutions, wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring.

In one aspect, the emissive dopant has the formula

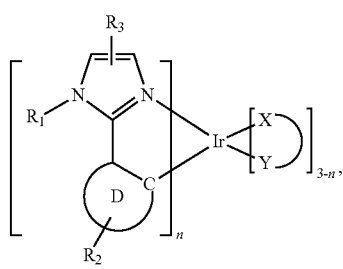

wherein D is a 5- or 6-membered carbocyclic or heterocyclic ring, wherein $R_1$, $R_2$, and $R_3$ independently represent mono, di, tri or tetra substitution, wherein each of $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein $R_1$ can be optionally linked to ring D, wherein n is 1, 2, or 3, and wherein X—Y is another ligand.

In one aspect, the device further comprises a second organic layer that is a non-emissive layer and the compound having Formula I is a material in the second organic layer.

In another aspect, the second organic layer is a blocking layer and the compound having Formula I is a blocking material in the second organic layer. In one aspect, the second organic layer is an electron transporting layer and the compound having the Formula I is an electron transporting material in the second organic layer.

In one aspect, the first device is a consumer product. In another aspect, the first device is an organic light-emitting device. In one aspect, the first device comprises a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
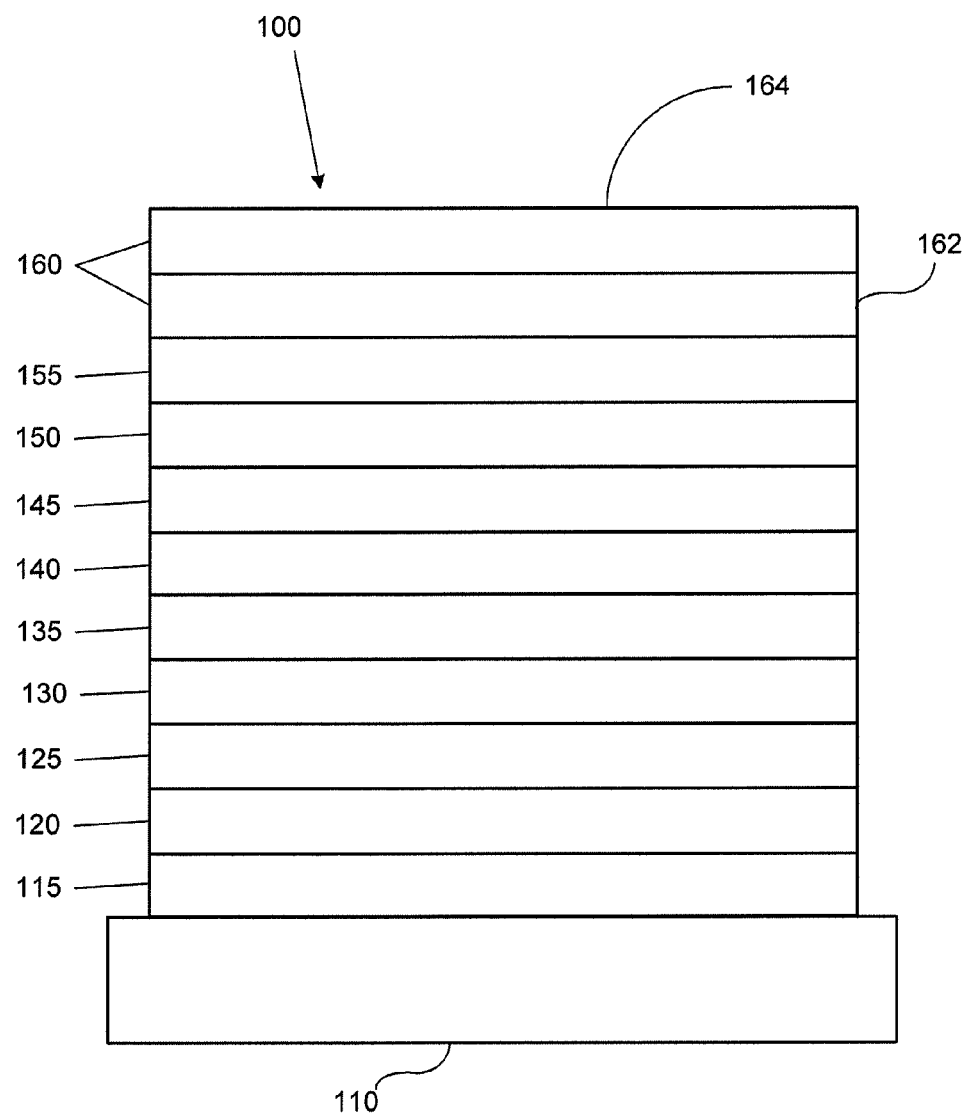
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
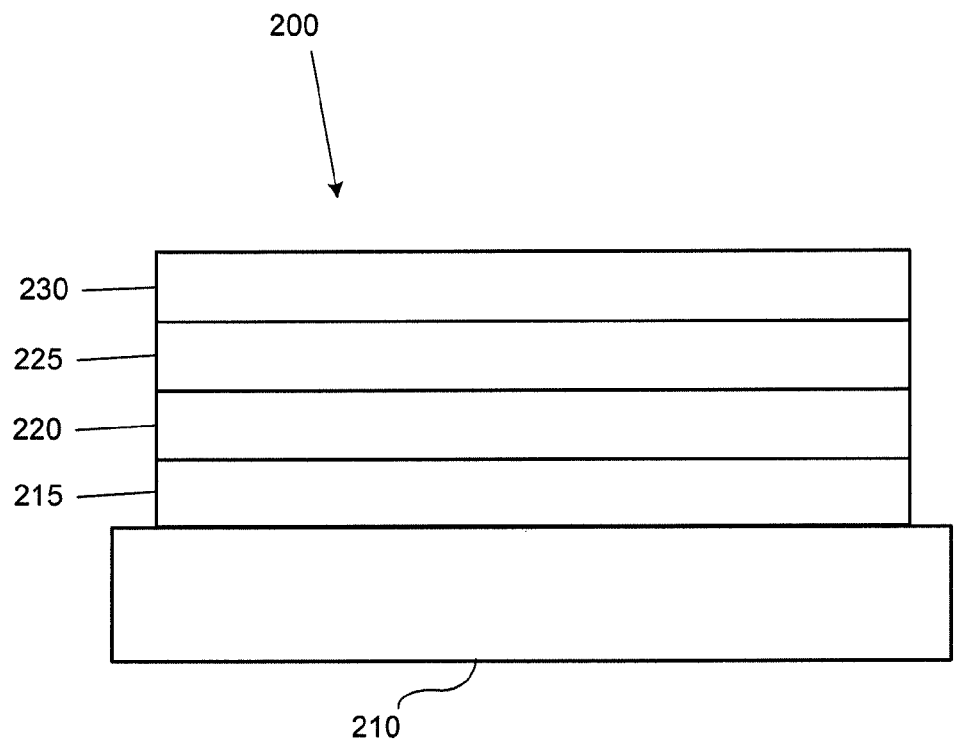
FIG. 2 shows an inverted organic light emitting device that does not have a separate electron transport layer.
Figure 3:
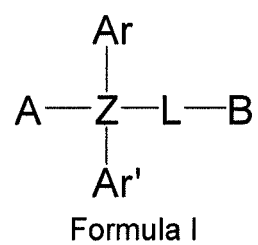
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the Formula I is provided:

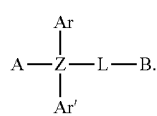

Formula I

In the compound of Formula I, Ar and Ar' are independently selected from the group consisting of phenyl, biphenyl, naphthalene, dibenzothiophene and dibenzofuran, which are optionally further substituted. Z is selected from Si and Ge. L is a single bond or comprises an aryl or heteroaryl group having from 5-20 carbon atoms, which is optionally further substituted. A is a group directly bonded to Z and is selected from the group consisting of triphenylene, tetraphenylene, pyrene, naphthalene, fluoranthene, chrysene, phenanthrene, azatriphenylene, azatetraphenylene, azapyrene, azanaphthalene, azafluoranthene, azachrysene, azaphenanthrene, and combinations thereof, which are optionally further substituted with one or more groups selected from the group consisting of hydrogen, deuterium, halide, alkyl, cycloalkyl, heteroalkyl, arylalkyl, aryl, aryloxy, and combinations thereof.

B contains a group selected from the group consisting of carbazole, dibenzofuran, dibenzothiophene, dibenzoselenophene, aza-carbazole, aza-dibenzofuran, aza-dibenzothiophene, azadibenzoselenophene, and combinations thereof, which are optionally further substituted with one or more groups selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole, dibenzofuran, dibenzothiophene, dibenzoselenophene, aza-carbazole, aza-dibenzofuran, aza-dibenzothiophene or azadibenzoselenophene group.

An "aryl" group is an aromatic all carbon group, which can contain one or more fused rings within it. Merely by way of example, and without any limitation, exemplary aryl groups can be phenyl, naphthalene, phenanthrene, corannulene, etc. A "heteroaryl" group is an "aryl" group containing at least one heteroatom. Merely by way of example, and without any limitation, exemplary heteroaryl groups can be pyridine, quinoline, phenanthroline, azacorannulene, etc. Both "aryl" and "heteroaryl" groups can have multiple attachment points connecting them to other fragments.

The "aza" designation in the fragments described above, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofurna). As used herein, these different ways of designating a substituent or attached fragment are considered to be equivalent.

As used herein, fragments containing the following structure:

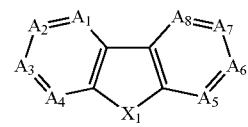

are called DBX groups, i.e. dibenzo $X_1$, where $X_1$ is any of the atoms or groups described herein. In the DBX group, $A_1$-$A_8$ can comprise carbon or nitrogen.

The novel compounds disclosed herein contain two distinctly different groups, polycyclic aromatic hydrocarbon, such as triphenylene/pyrene-based group A, and DBX- or carbazole-based group B, connected with a silane or germane spacer, resulting in an asymmetric structure. These compounds have a number of advantageous properties when used in OLED devices. Firstly, triphenylene and pyrene have excellent charge-transport capabilities, while DBX and carbazole have appropriate LUMO and HOMO levels, for electron and hole injection from adjacent layers. The combination of triphenylene/pyrene and DBX or carbazole results in compounds favorable for both charge injection and transport. Further derivatization on these groups can maintain, and even improve, the excellent charge injection and transport characteristics. Secondly, the silane and germane spacers break the conjugation between groups A and B, retaining the high triplet energies of the individual groups in the entire molecule, and thus effectively reducing quenching and allowing for the use of compounds of Formula I with high triplet energy emitters.

The compounds of Formula I have additional advantages over known symmetric analogs because compounds of Formula I are less prone to crystallization. As a result, compounds of Formula I possess improved film uniformity, which, without being bound by theory, is believed to be a result of reduction in phase separation between the emitters and host materials in OLEDs. The novel compounds of Formula I can be used to improve OLED device performance parameters, such as emission spectrum line shape, efficiency and lifetime. Furthermore, compounds of Formula I also tend to be soluble in organic solvents such as toluene, xylene, and 3-phenoxytoluene, and are amenable to solution processing which is highly desirable for low-cost lighting applications.

In one embodiment, A is

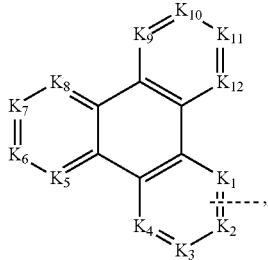

wherein $K_1$ to $K_{12}$ are independently selected from N and C—R', and wherein R' is selected from the group consisting of hydrogen, deuterium, halide, alkyl, cycloalkyl, heteroalkyl, arylalkyl, aryl, aryloxy, and combinations thereof.

In one embodiment, B is selected from the group consisting of:

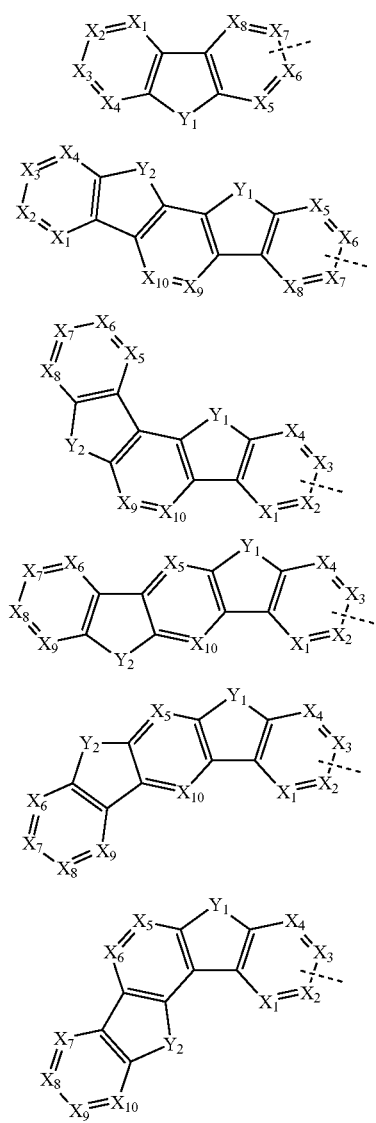

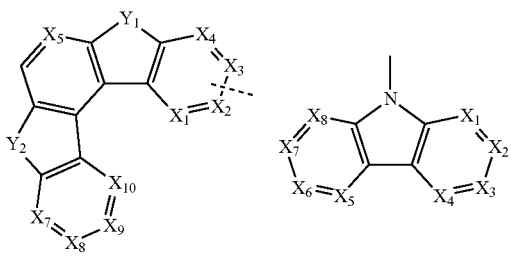

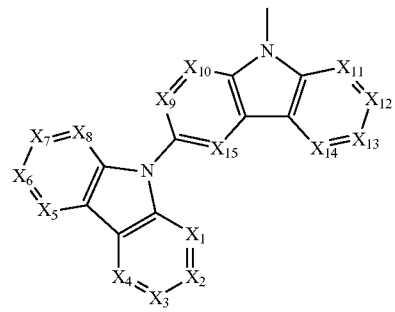

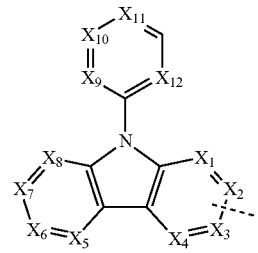

wherein $X_1$-$X_{15}$ are independently selected from the group consisting of N and C—R'', wherein R'' is selected from a group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein $Y_1$ and $Y_2$ are independently selected from the group consisting of O, S, and Se. The dashed lines in the chemical structures disclosed herein represent a bond through any position on that group capable of forming a single bond with another atom.

In one embodiment, A is selected from the group consisting of:

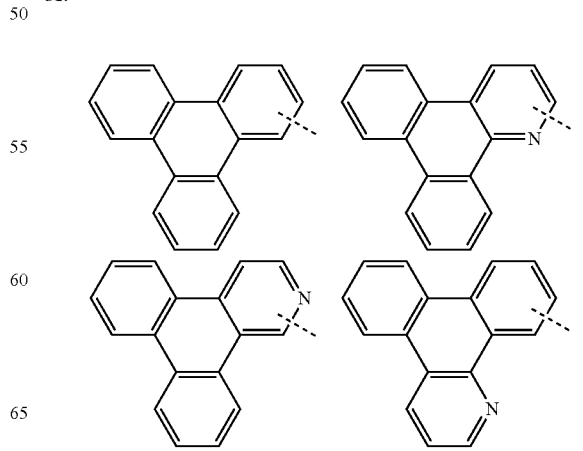

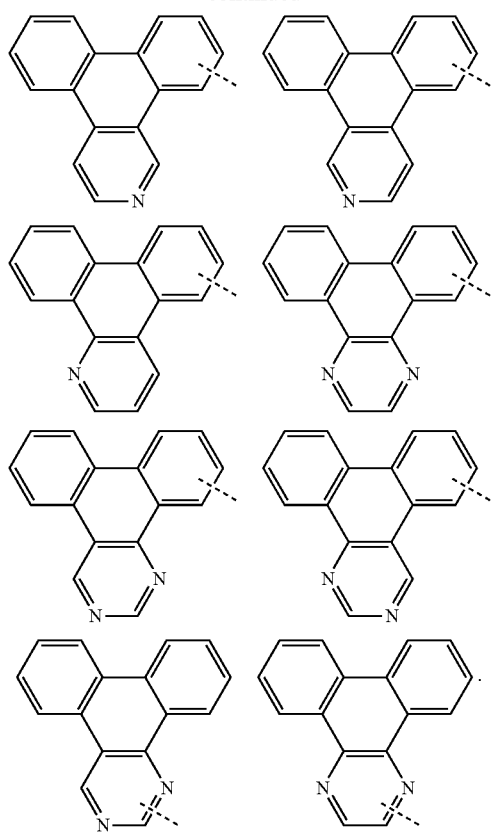
In one embodiment, A is selected from the group consisting of:
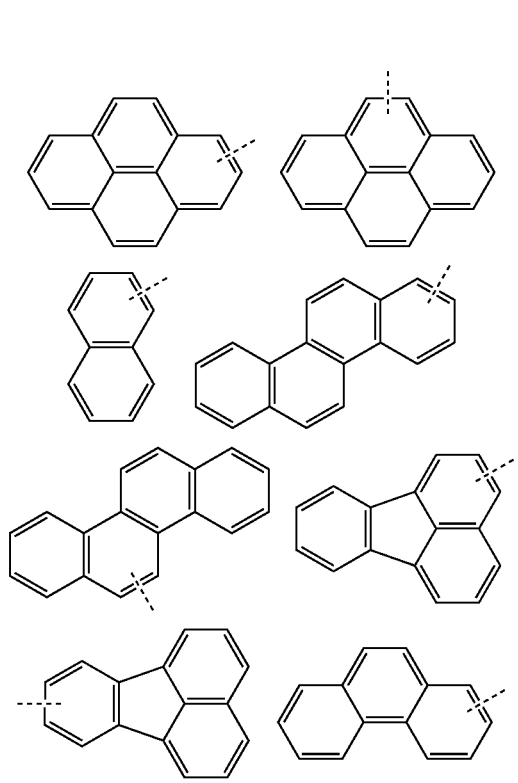
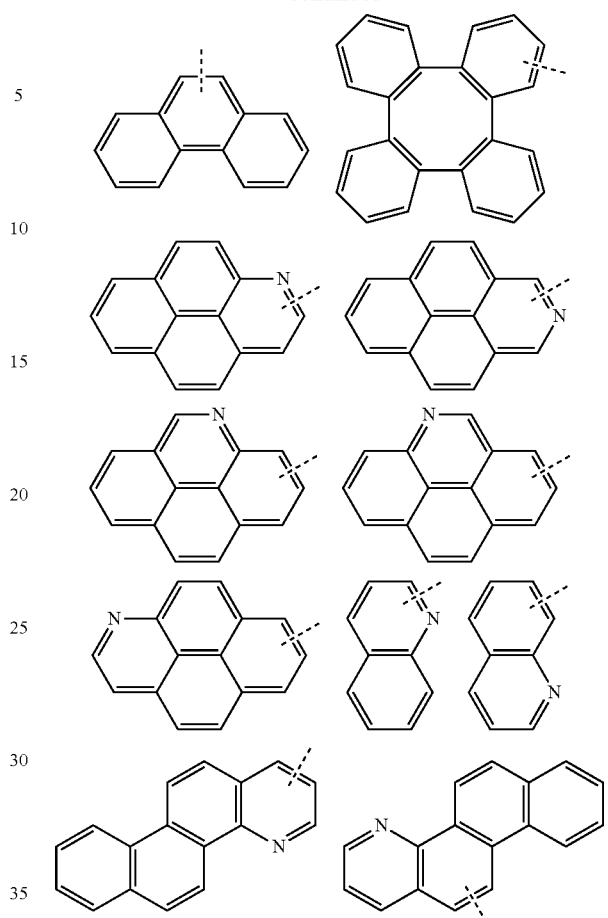

In one embodiment, B is selected from the group consisting of:
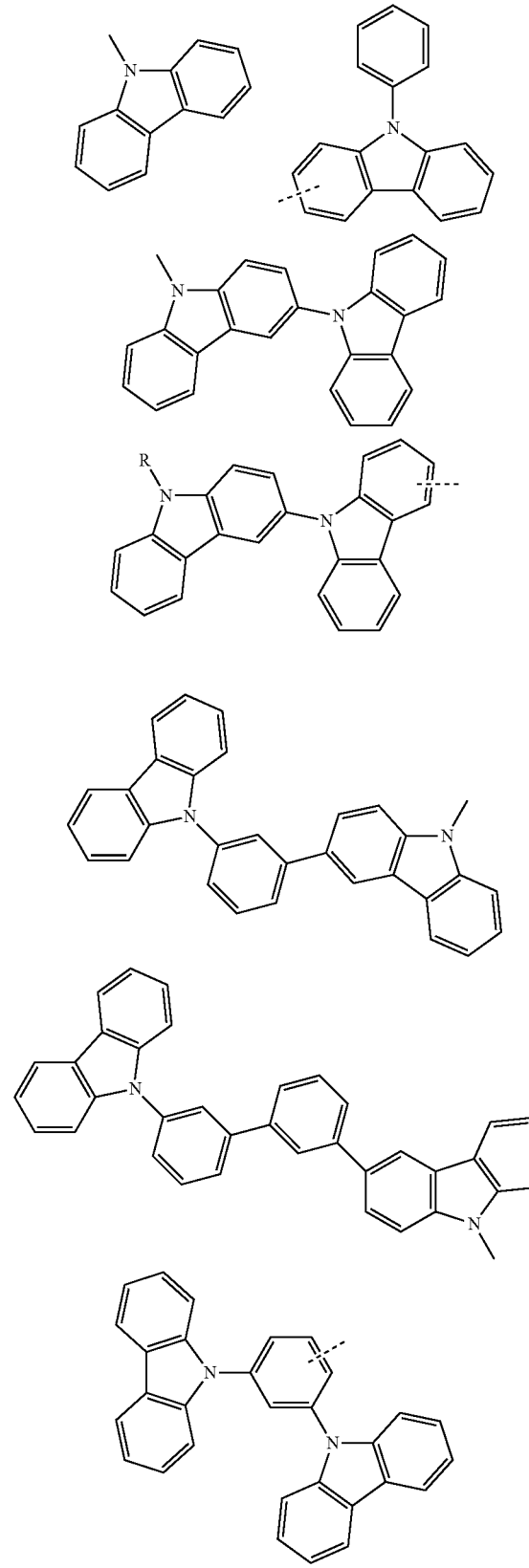
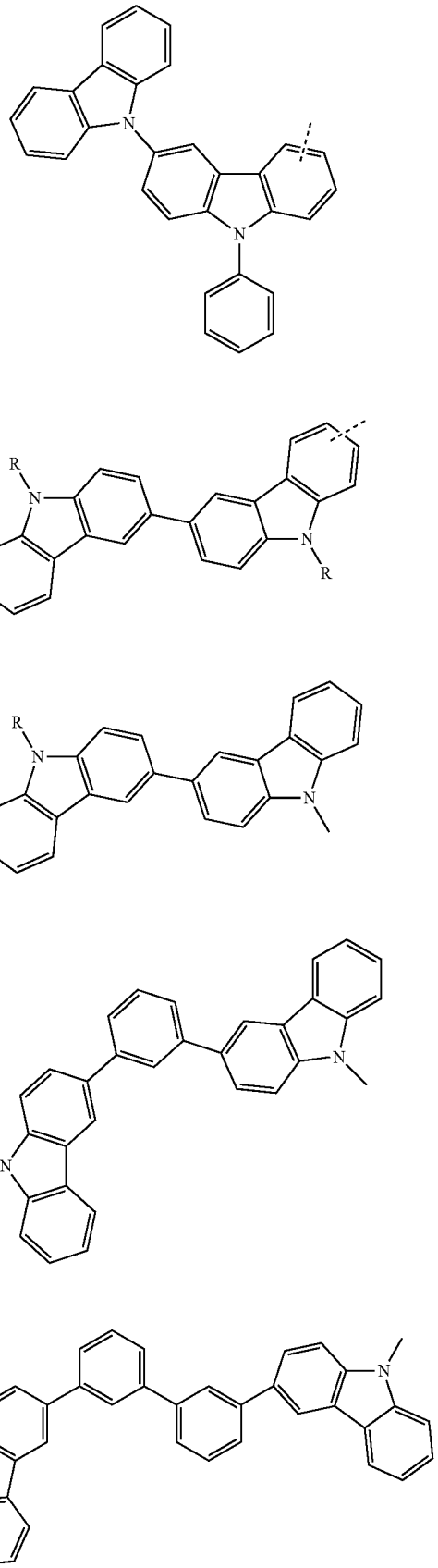

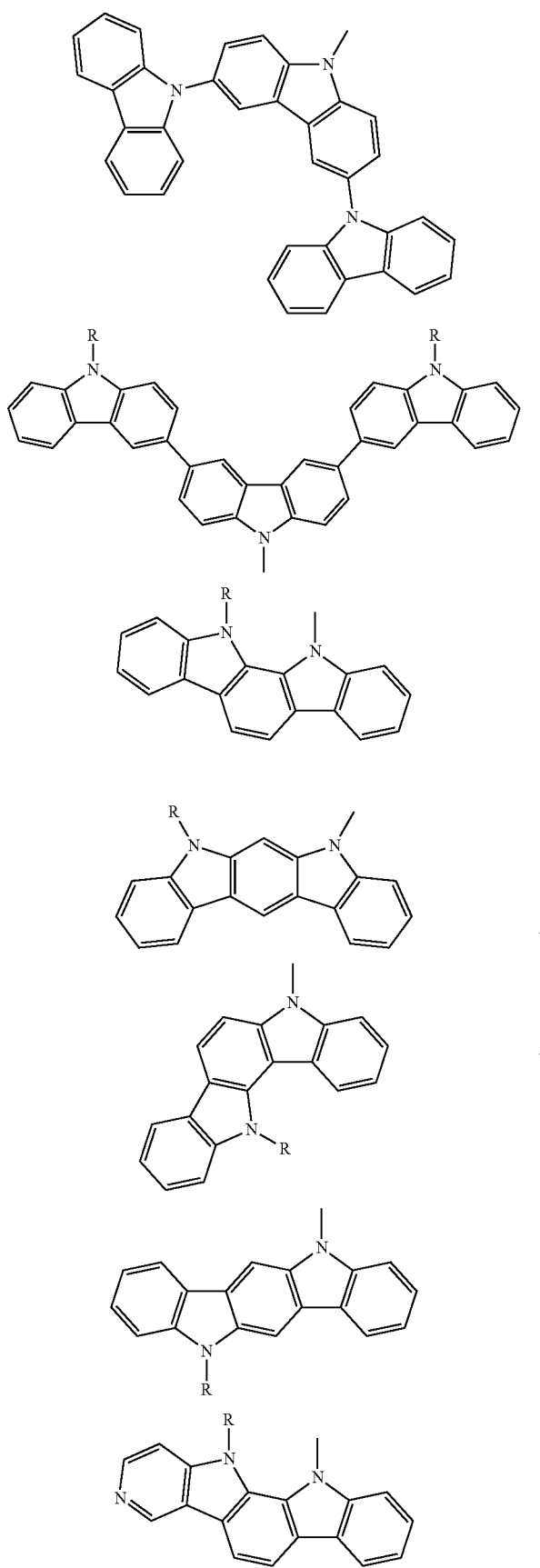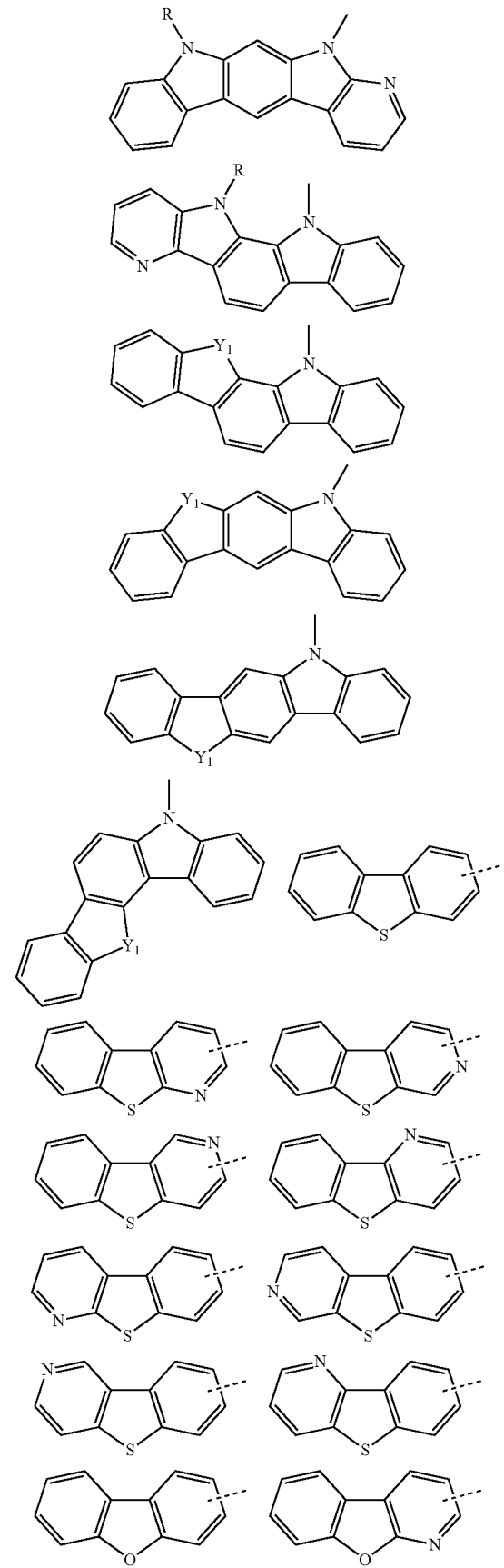

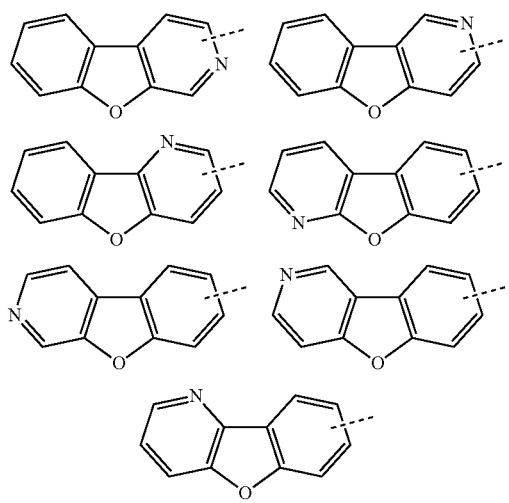

wherein $Y_1$ is selected from the group consisting of O, S, and Se, wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, L is independently selected from the group consisting of:

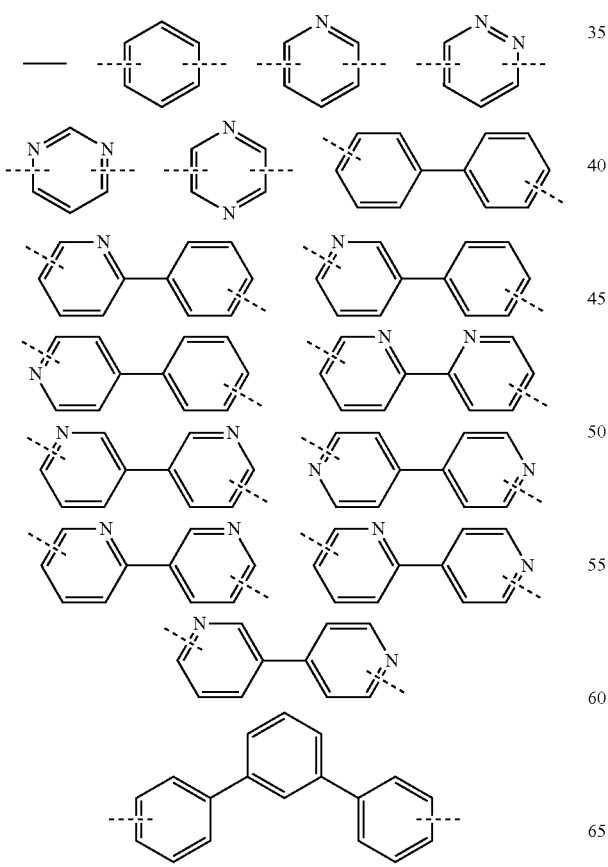

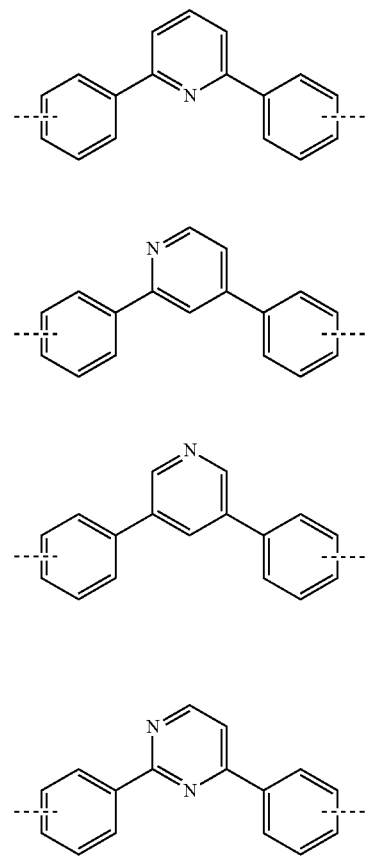

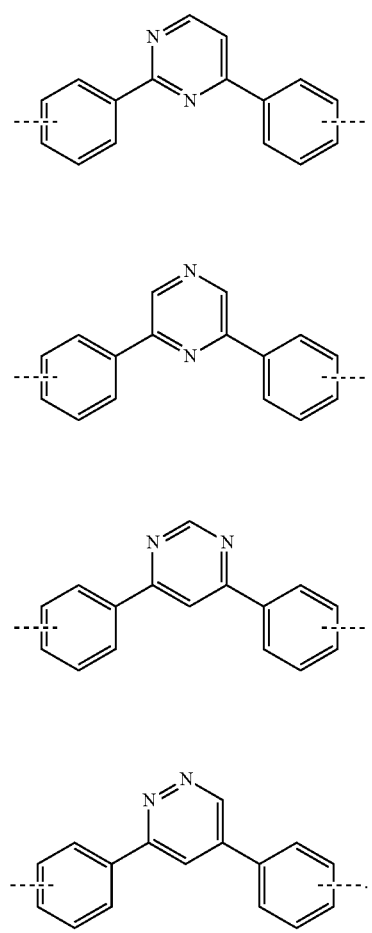

In one embodiment, A is tripheynylene. In another embodiment, A is pyrene. In one embodiment, Ar and Ar' are phenyl. In one embodiment, L is phenyl.

In one embodiment, the compound is selected from the group consisting of:
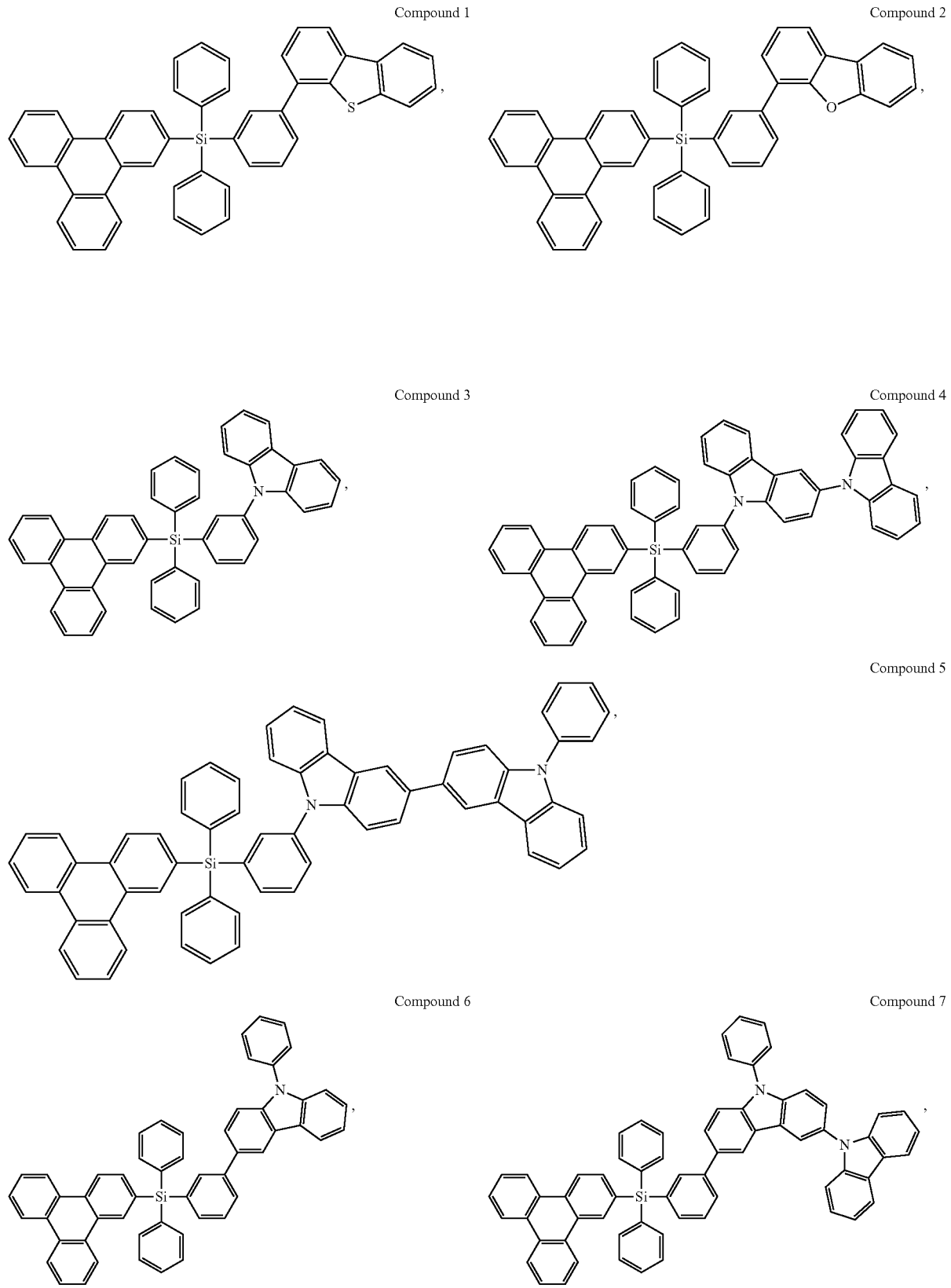

-continued
Compound 8
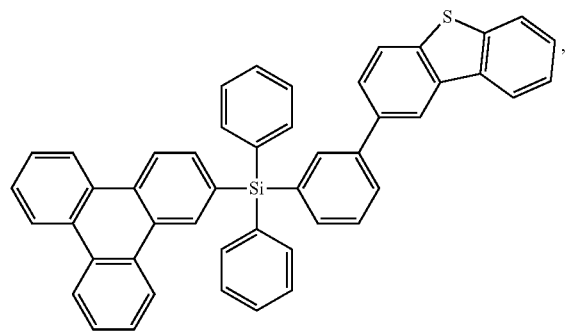
Compound 9
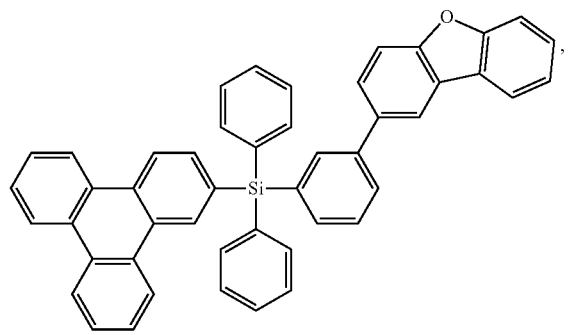
Compound 10
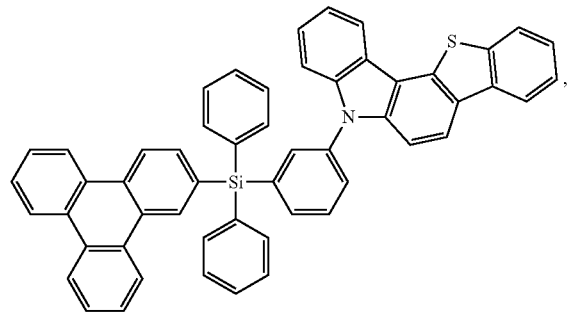
Compound 11
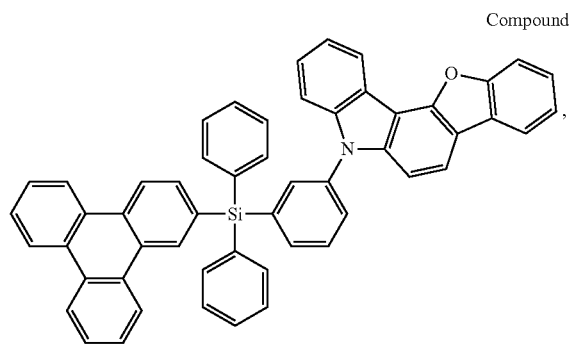
Compound 12
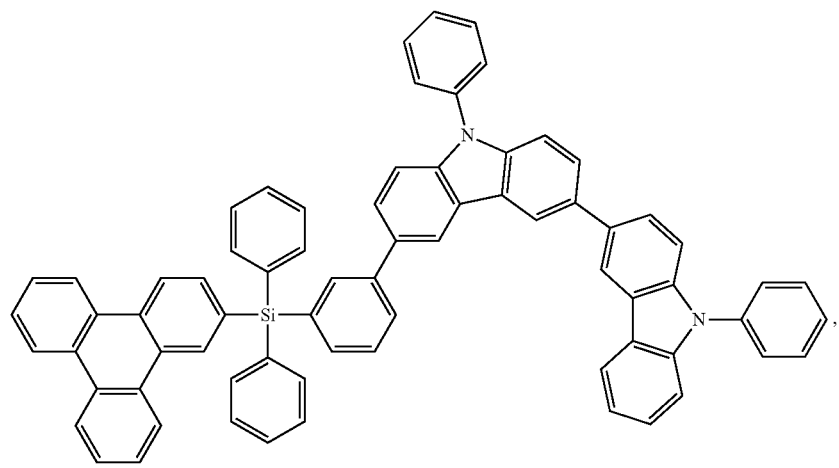
Compound 13
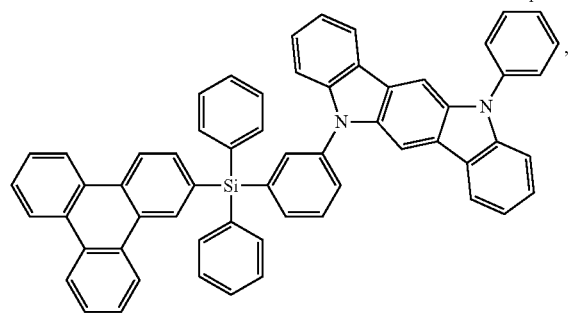
Compound 14
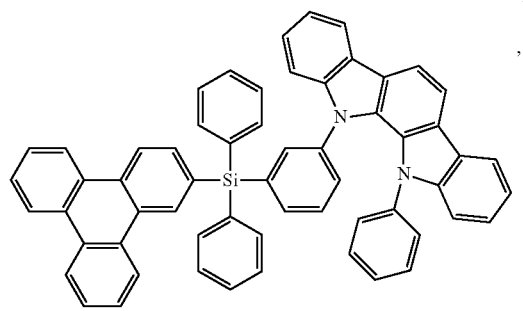

-continued
Compound 15
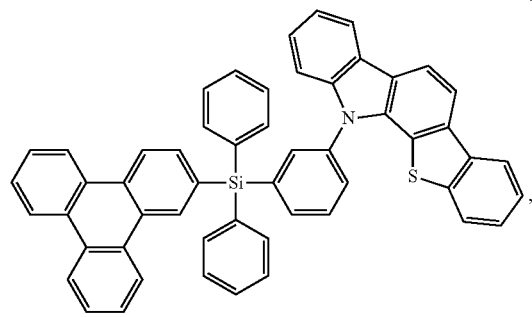
Compound 16
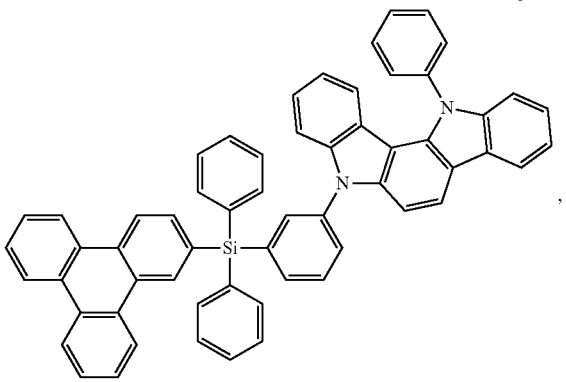
Compound 17
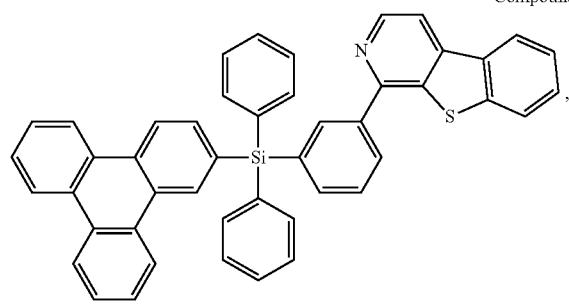
Compound 18
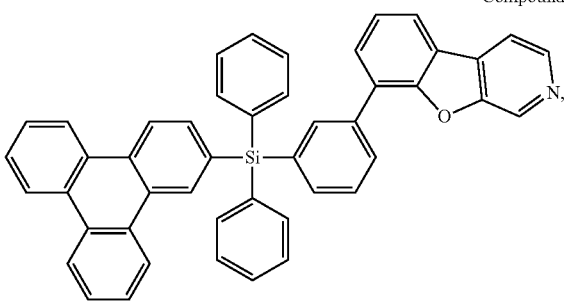
Compound 19
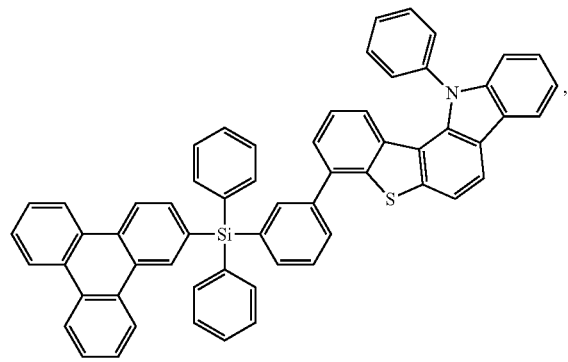
Compound 20
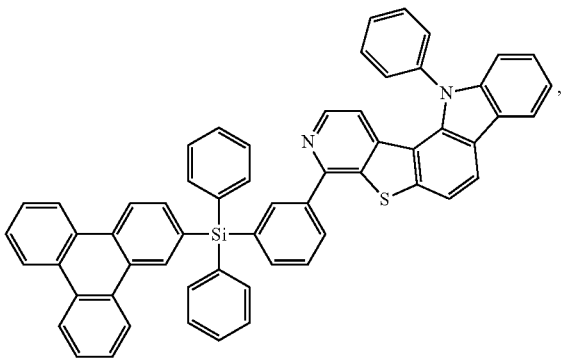
Compound 21
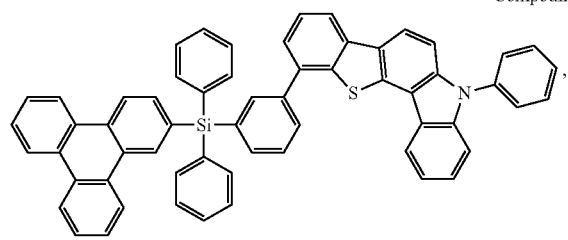
Compound 22
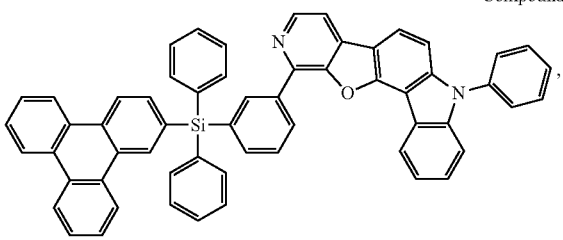
Compound 23
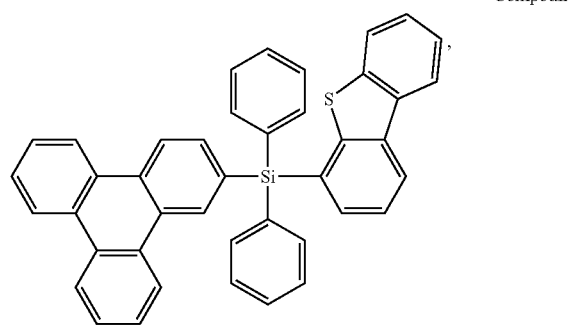
Compound 24
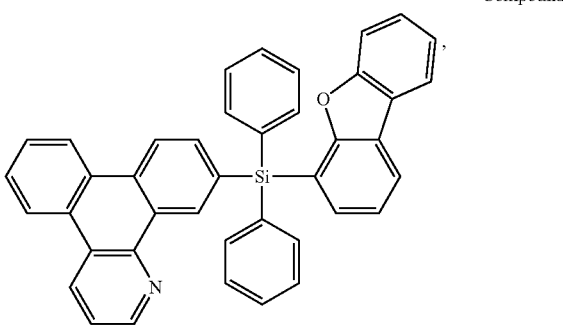

-continued
Compound 25
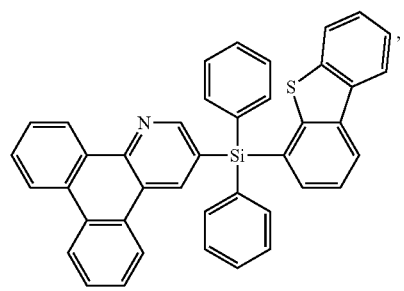
Compound 26
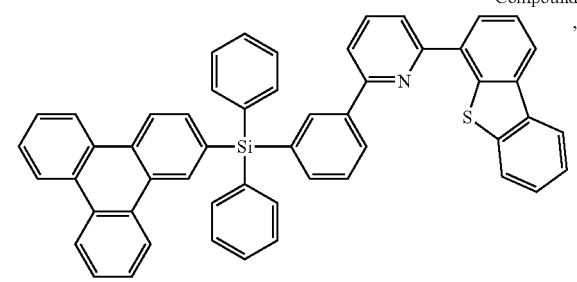
Compound 27
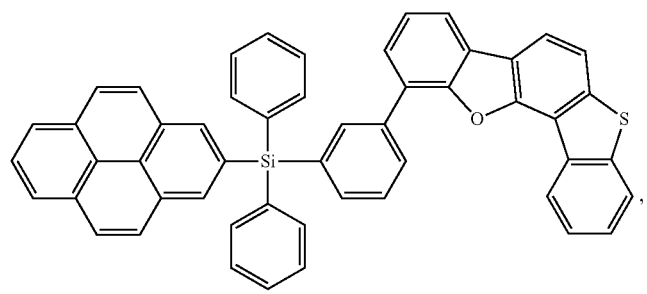
Compound 28
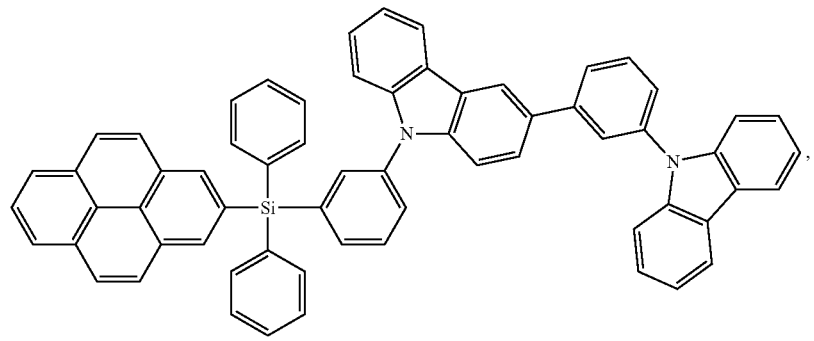
Compound 29
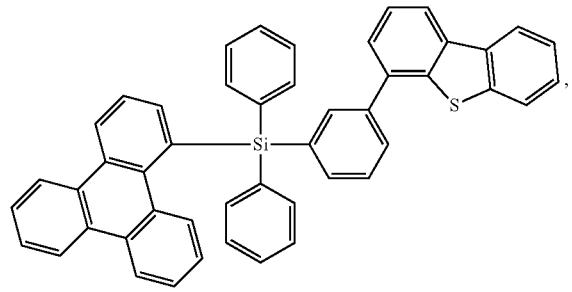
Compound 30
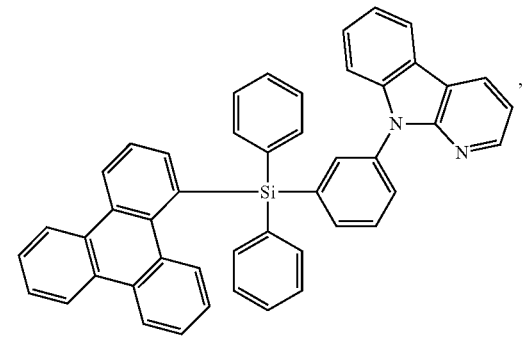
Compound 31
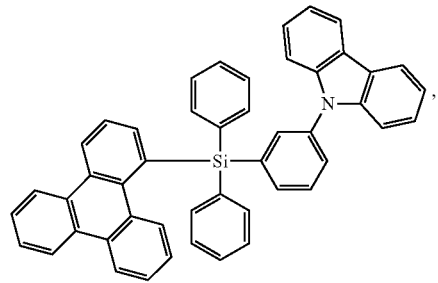
Compound 32
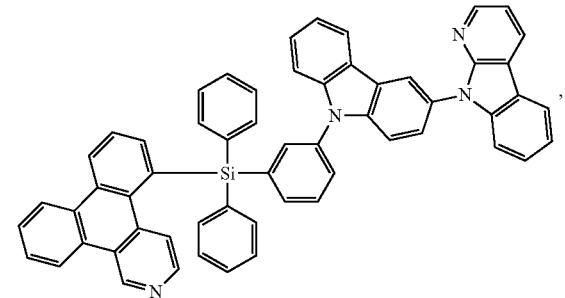

-continued

Compound 33 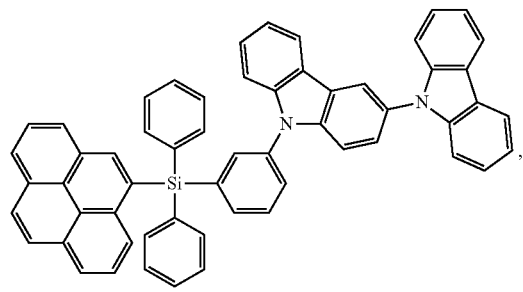,

Compound 34 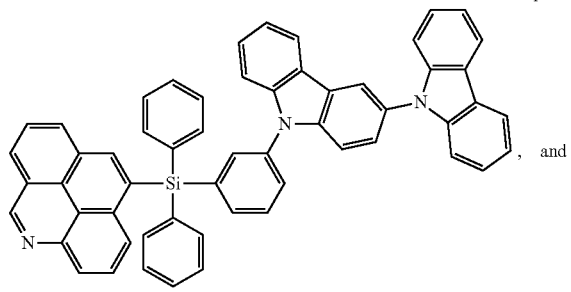, and

Compound 35 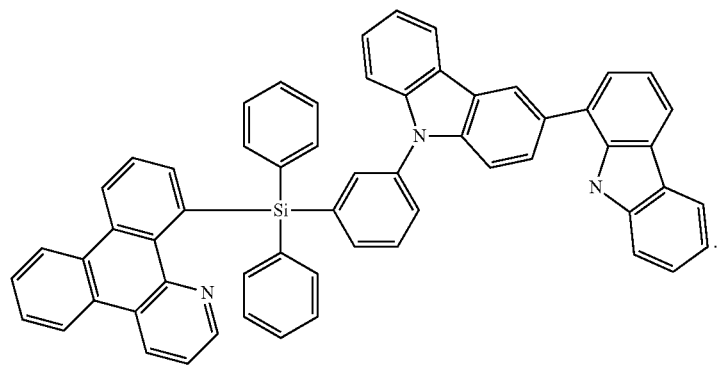.

The structures of the Comparative Compounds described herein are as follows:

CC-1 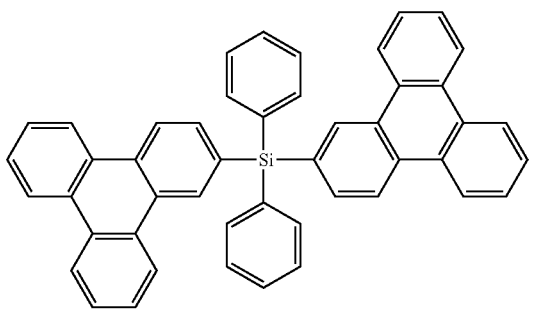

CC-2 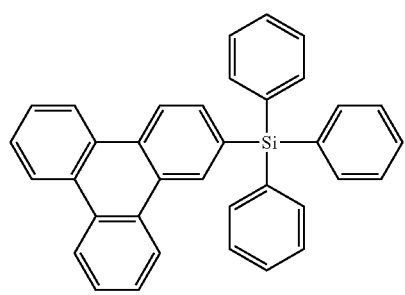

-continued

CC-3 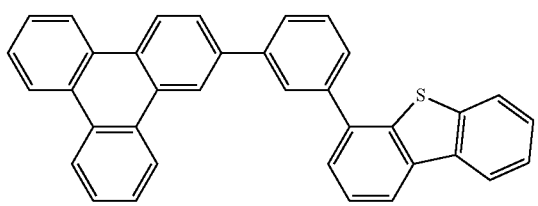

Table 1 lists the triplet energy levels for Compound 1-4 and Comparative Compounds CC-1 and CC-3. The triplet energy was measured from the maximum of the highest energy 0-0 vibronic band of the phosphorescence spectra collected in $10^{-4}$ M solution of the corresponding compound in 2-methyltetrahydrofuran at 77 K. While comparative compound CC-3, where triphenylene is connected with dibenzothiophene through a benzene unit, has a triplet energy of 2.64 eV, Compound 1 of Formula I, where a silane unit is inserted between triphenylene and the rest of the aromatic system, has a much higher triplet energy of 2.86 eV. This suggests that introduction of silane group is able to maintain a high triplet energy of triphenylene. This is also supported by the results of Compounds 2-4 and CC-1. A high triplet energy is required for the host materials to accommodate blue phosphorescent emitters.

TABLE 1

Selected Triplet Energy Levels for Compounds of Formula I and Comparison Compounds

| Compound | Triplet energy, eV |
|---|---|
| Compound 1 | 2.86 |
| Compound 2 | 2.86 |

TABLE 1-continued

Selected Triplet Energy Levels for Compounds
of Formula I and Comparison Compounds

| Compound | Triplet energy, eV |
|---|---|
| Compound 3 | 2.86 |
| Compound 4 | 2.86 |
| CC-1 | 2.88 |
| CC-3 | 2.64 |

Table 2 lists the HOMO/LUMO energy levels for selected compounds of Formula I and Comparative Compound CC-1. The HOMO/LUMO levels were measured by differential pulse voltammetry in DMF solutions at a concentration of $10^{-3}$ M, with 0.1 M tetrabutylammonium hexafluorophosphate as the supporting electrolyte. A glass carbon disk, a platinum wire and a silver wire are used as the working, counter and pseudo reference electrodes, respectively. Ferrocene is added into the solution to serve as the internal standard for each measurement. The resultant oxidation potential ($E_{ox}$) and reduction potential ($E_{red}$), adjusted to ferrocene, are used to calculate the HOMO/LUMO levels as $-4.8$ eV$-qE_{ox}$ and $-4.8$ eV$-qE_{red}$, respectively, where q is the electron charge. All compounds have LUMO levels at about $-2.1$ eV, suitable for electron injection from adjacent electron transport layers. Though comparative compound CC-1 has a HOMO level below $-6.00$ eV, which is the measurement limit, the HOMO levels for compounds of Formula I could be tuned through variation of B group. Indeed, the HOMO levels of Compounds 3, 4 and 5 were found to be $-5.67$, $-5.55$ and $-5.41$ eV, respectively. It is noted that these HOMO levels are below commonly used triplet emitters, allowing efficient hole trapping in the device operation.

TABLE 2

Selected HOMO/LUMO Energy Levels for Compounds
of Formula I and Comparison Compounds

| Compound | HOMO, eV | LUMO, eV |
|---|---|---|
| Compound 1 | <−6.00 | −2.08 |
| Compound 2 | <−6.00 | −2.06 |
| Compound 3 | −5.67 | −2.08 |
| Compound 4 | −5.55 | −2.07 |
| Compound 5 | −5.41 | −2.04 |
| CC-1 | <−6.00 | −2.05 |

Figure 5:
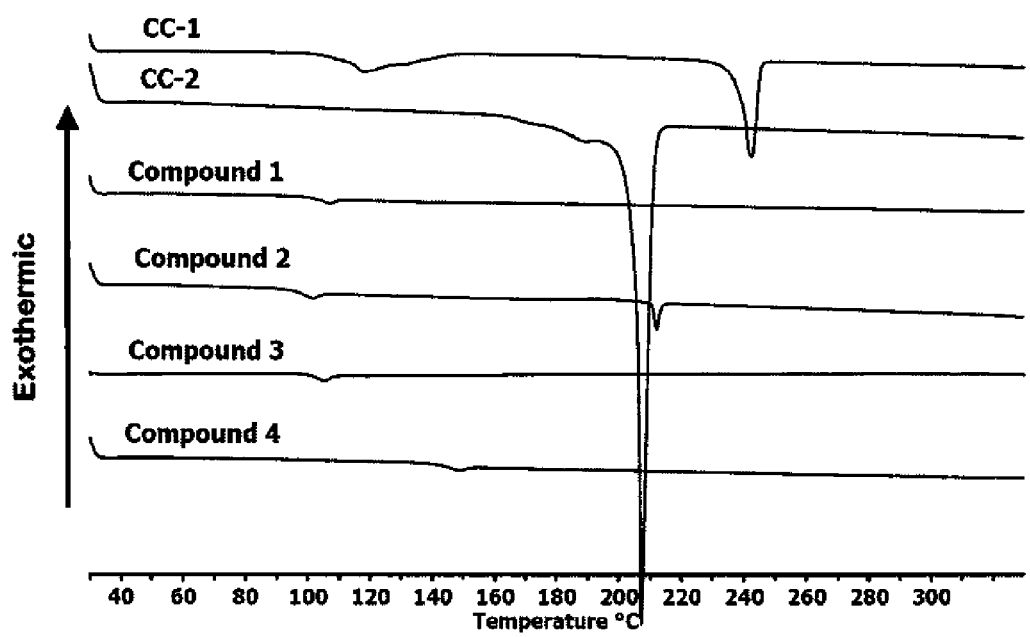
FIG. 5 shows the differential scanning calorimetry scans for selected compounds of Formula I and for selected comparative compounds.

FIG. 5 shows the differential scanning calorimetry (DSC) curves for selected compounds of Formula I and for Comparative Compounds CC-1 and CC-2. Samples were thermally vaporized under vacuum at a pressure less than $10^{-5}$ Torr and condensed in a zone 100° C. cooler than the vaporization zone. The condensed samples were gradually cooled to room temperature before subjecting to DSC measurement where the reported first heating scans were recorded at 10° C./min under nitrogen atmosphere. With asymmetric structures, compounds of Formula I are amorphous with stable morphological stability. During heating from 30° C. to 330° C., Compounds 1, 3 and 4 undergo glass transitions at 103, 101, and 144° C., respectively, without encountering any crystallization or melting. Compound 2 shows a small melting peak at 212° C. with a small melting enthalpy of 2 J/g due to residual crystals embedded in an amorphous bulk. On the other hand, CC-1 with a symmetric structure encounters a pronounced melting peak at 243° C. with a melting enthalpy of 58 J/g, suggesting the presence of significant crystals. Furthermore, CC-2 comprising a simple triphenylsilyl group attached to triphenylene is highly crystalline with a melting peak at 207° C. accompanied by a melting enthalpy of 75 J/g. In fact, CC-2 does not undergo any glass transition during the first heating scan, suggesting the absence of amorphous phase and complete crystallinity. These DSC results demonstrated that the asymmetric structure according to this invention is effective in suppressing crystallization and is conducive to a stable amorphous morphology, which is beneficial to device operational stability.

In one embodiment, a first device is provided. The first device comprises an organic light-emitting device, which further comprises an anode, a cathode, and an organic layer, disposed between the anode and the cathode, comprising a compound having the Formula I:

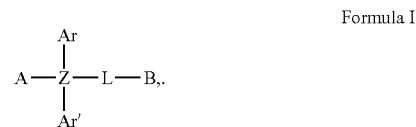

Formula I

In the compound of Formula I, Ar and Ar' are independently selected from the group consisting of phenyl, biphenyl, naphthalene, dibenzothiophene and dibenzofuran, which are optionally further substituted. Z is selected from Si and Ge. L is a single bond or comprises an aryl or heteroaryl group having from 5-20 carbon atoms, which is optionally further substituted. A is a group directly bonded to Z and is selected from the group consisting of triphenylene, tetraphenylene, pyrene, naphthalene, fluoranthene, chrysene, phenanthrene, azatriphenylene, azatetraphenylene, azapyrene, azanaphthalene, azafluoranthene, azachrysene, azaphenanthrene, and combinations thereof, which are optionally further substituted with one or more groups selected from the group consisting of hydrogen, deuterium, halide, alkyl, cycloalkyl, heteroalkyl, arylalkyl, aryl, aryloxy, and combinations thereof.

B contains a group selected from the group consisting of carbazole, dibenzofuran, dibenzothiophene, dibenzoselenophene, aza-carbazole, aza-dibenzofuran, aza-dibenzothiophene, azadibenzoselenophene, and combinations thereof, which are optionally further substituted with one or more groups selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole, dibenzofuran, dibenzothiophene, dibenzoselenophene, aza-carbazole, aza-dibenzofuran, azadibenzothiophene or azadibenzoselenophene group.

In one embodiment, the organic layer is an emissive layer and the compound of Formula I is a host. In another aspect, the organic layer further comprises an emissive dopant.

In one embodiment, the emissive dopant is a transition metal complex having at least one ligand selected from the group consisting of:

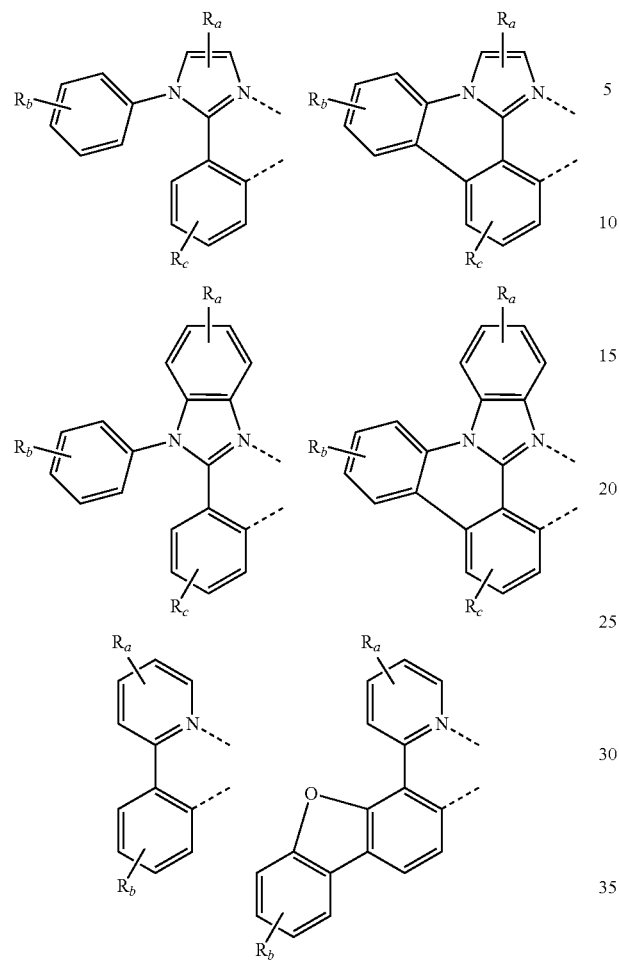

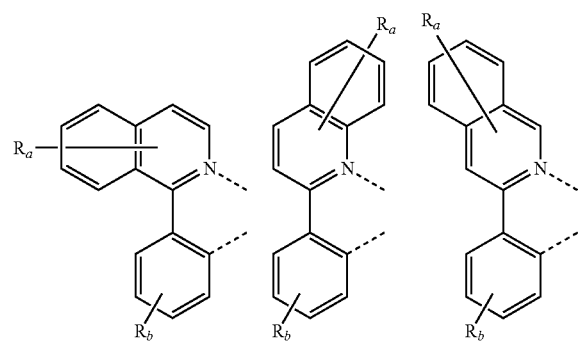

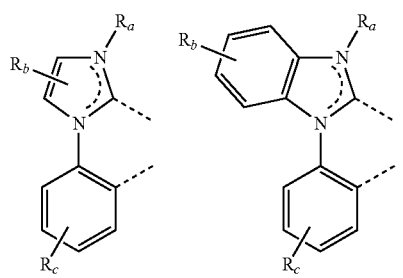

wherein $R_a$, $R_b$, and $R_c$ may represent mono, di, tri or tetra substitutions, wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring.

In one embodiment, the emissive dopant has the formula

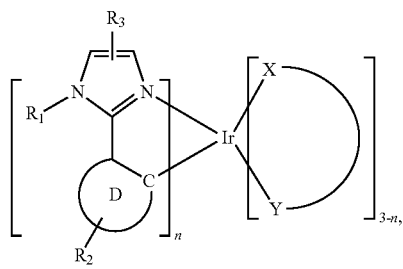

wherein D is a 5- or 6-membered carbocyclic or heterocyclic ring, wherein $R_1$, $R_2$, and $R_3$ independently represent mono, di, tri or tetra substitution, wherein each of $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein $R_1$ can be optionally linked to ring D, wherein n is 1, 2, or 3, and wherein X—Y is another ligand.

In one embodiment, the device further comprises a second organic layer that is a non-emissive layer and the compound having Formula I is a material in the second organic layer.

In another embodiment, the second organic layer is a blocking layer and the compound having Formula I is a blocking material in the second organic layer. In one embodiment, the second organic layer is an electron transporting layer and the compound having the Formula I is an electron transporting material in the second organic layer.

In one embodiment, the first device is a consumer product. In another embodiment, the first device is an organic light-emitting device. In one embodiment, the first device comprises a lighting panel.

Device Examples

The exemplary devices described below may advantageously utilize the compounds of Formula I, and are not intended to be limiting. The structures of the materials used in the device examples are shown below:

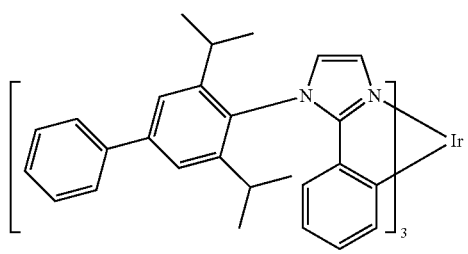

Dopant D

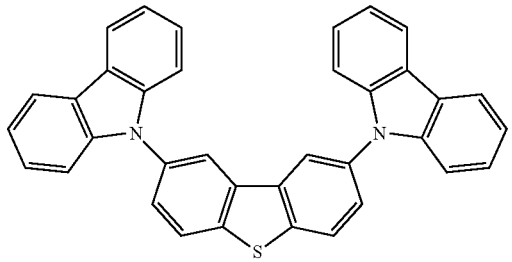

Compound BL

-continued

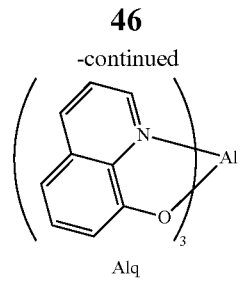

Alq

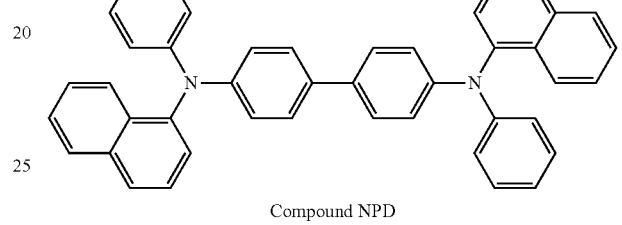

Compound NPD

All example devices were fabricated by high vacuum ($<10^{-4}$ Torr) thermal evaporation (VTE). The anode electrode is 800 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Figure 4:
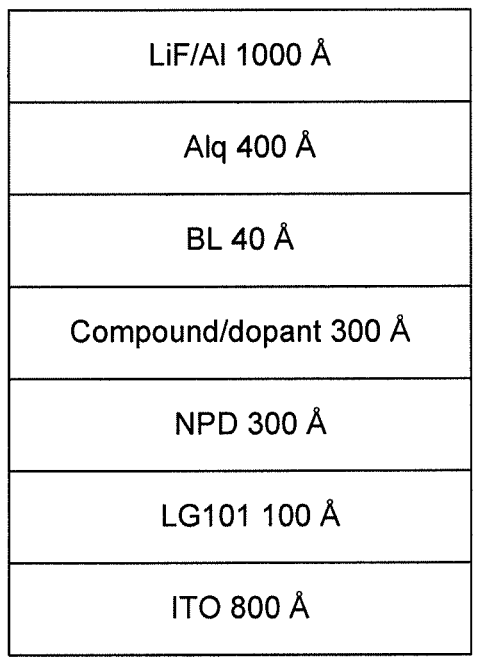
FIG. 4 shows an example device that incorporates compounds of Formula I.

The organic stack of the OLED device used in the Examples and Comparative Device Examples has the following structure: from the ITO surface, 100 Å of LG101 (purchased from LG Chem) as the hole injection layer, 300 Å of NPD as the hole transporting layer (HTL), 300 Å of a compound of Formula I (or comparative compound CC-1 or CC2) doped with 15 weight percent of Dopant D as the emissive layer (EML), 50 Å of Compound BL as the Blocking Layer (BL) and 400 Å of Alq as the electron transport layer (ETL). A schematic exemplary device structure is depicted in FIG. 4.

TABLE 3

Summary of Device Data

| Example | Host | Dopant | BL | 1931 CIE x | 1931 CIE y | $\lambda_{max}$ [nm] | At 1000 nits LE [cd/A] | At 1000 nits EQE [%] | At 1000 nits PE [lm/W] | At 20 mA/cm² $LT_{80\%}$ [h] |
|---|---|---|---|---|---|---|---|---|---|---|
| Device Example 1 | Compound 1 | Dopant D | Compound BL | 0.173 | 0.3913 | 474 | 44.7 | 19.8 | 24 | 11.4 |
| Device Example2 | Compound 3 | Dopant D | Compound BL | 0.1737 | 0.3887 | 474 | 44 | 19.5 | 23.4 | 16.0 |

TABLE 3-continued

Summary of Device Data

| Example | Host | Dopant | BL | 1931 CIE | | $\lambda_{max}$ [nm] | At 1000 nits | | | At 20 mA/cm² |
|---|---|---|---|---|---|---|---|---|---|---|
| | | | | x | y | | LE [cd/A] | EQE [%] | PE [lm/W] | $LT_{80\%}$ [h] |
| Device Example 3 | Compound 4 | Dopant D | Compound BL | 0.1781 | 0.4034 | 476 | 44.3 | 19.2 | 22.9 | 24.2 |
| Comparative Device Example 1 | CC-1 | Dopant D | Compound BL | 0.1803 | 0.3877 | 474 | 23.7 | 10.5 | 10.3 | 18.5 |
| Comparative Device Example 2 | CC-2 | Dopant D | Compound BL | 0.1853 | 0.3986 | 474 | 24.3 | 10.5 | 9.8 | 0.01 |

Table 3 contains a summary of the device data. The luminous efficiency (LE), external quantum efficiency (EQE) and power efficiency (PE) were measured at 1000 nits, while the lifetime ($LT_{80\%}$) was defined as the time required for the device to decay to 80% of its initial luminance under a constant current density of 20 mA/cm². Compared to the devices based on comparative examples, i.e. Comparative Device Examples 1 and 2, the devices based on compounds of Formula I, i.e. Device Examples 1 to 3, exhibit two-fold improvement in device efficiencies (LE, EQE and PE), while maintaining comparable or even extended operational lifetimes. The improvement in device performance is attributable to the improved charge injection and transport of the asymmetric compounds of Formula I, which helps to balance charge fluxes. Without being bound by theory, it is believed that the balanced electron/hole fluxes spread the charge recombination zone, which preserves a high efficiency at high brightness by suppressing or reducing exciton quenching. An expanded charge recombination zone also extends the device lifetime by allowing a larger population of molecules to have charge transport, exciton formation, and light emission roles. Based on the HOMO/LUMO levels reported in Table 2, compounds of Formula I can also be used in the hole blocking layers. Since compounds of Formula I can serve both as hosts and hole blocking materials in the hole blocking layers, incorporation of compounds of Formula I into optical devices is expected to reduce device fabrication costs.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

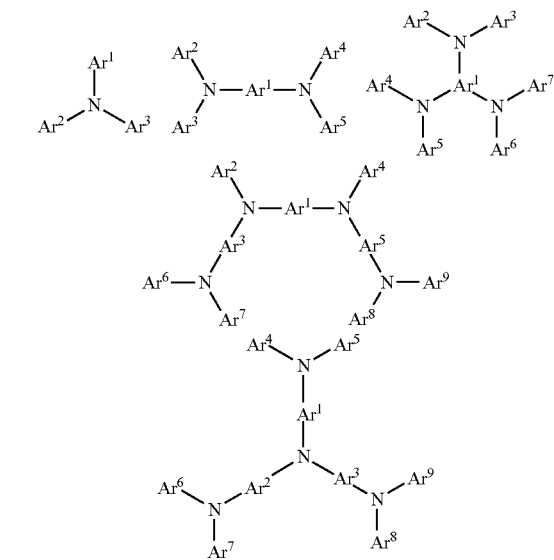

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

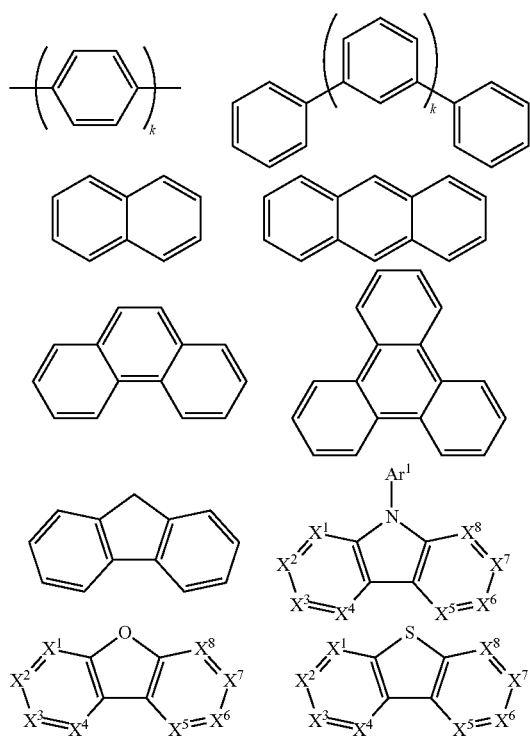

k is an integer from 1 to 20; $X^1$ to $X^8$ is C (including CH) or N; $Ar^1$ has the same group defined above.

Examples of metal complexes used in HIL or HTL include, but not limit to the following general formula:

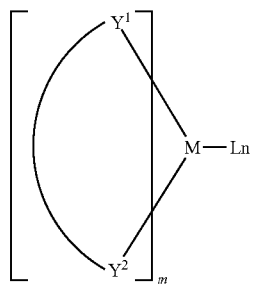

M is a metal, having an atomic weight greater than 40; $(Y^1\text{-}Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1\text{-}Y^2)$ is a 2-phenylpyridine derivative.

In another aspect, $(Y^1\text{-}Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

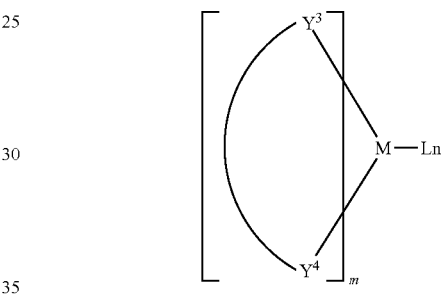

M is a metal; $(Y^3\text{-}Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

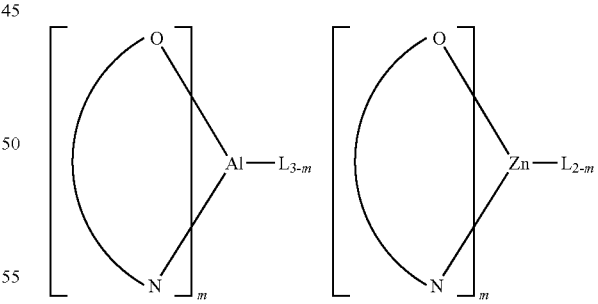

(O—N) is a bidentate ligand, having metal coordinated to atoms O and N.

In another aspect, M is selected from Ir and Pt.

In a further aspect, $(Y^3\text{-}Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

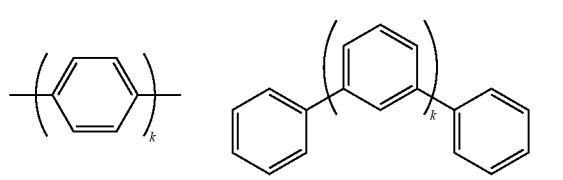

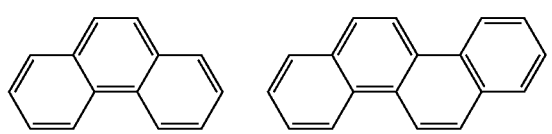

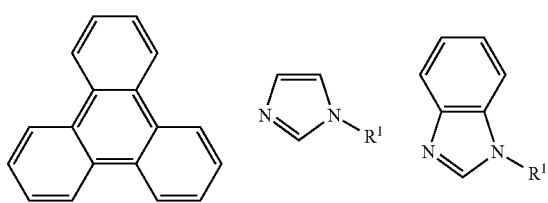

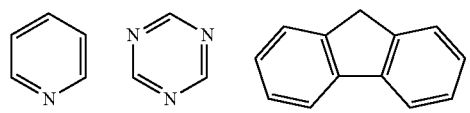

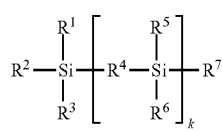

-continued

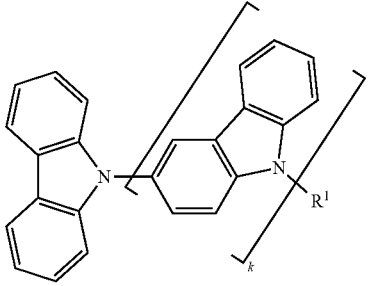

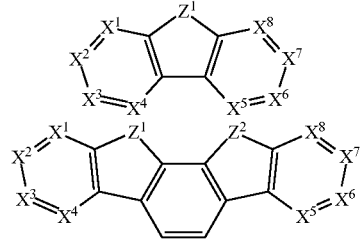

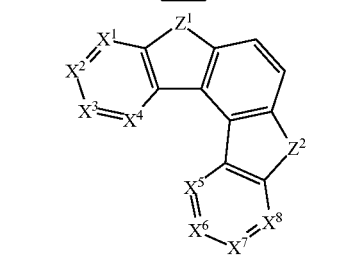

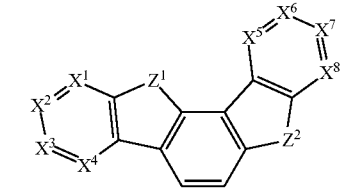

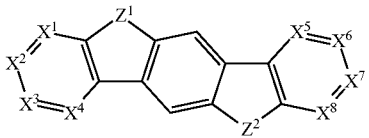

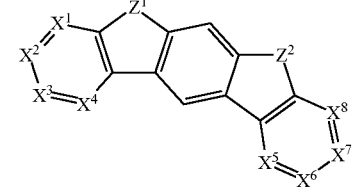

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

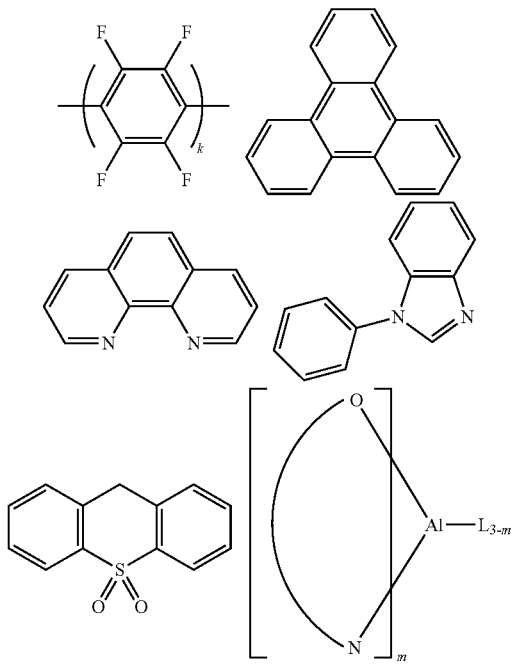

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

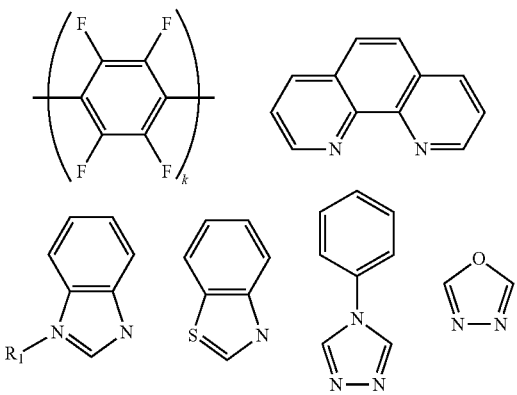

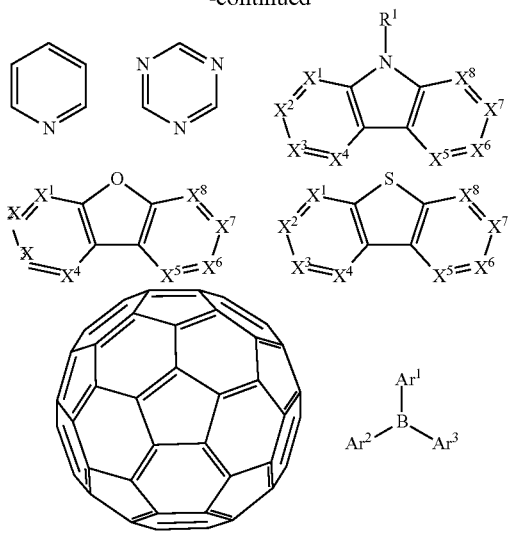

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

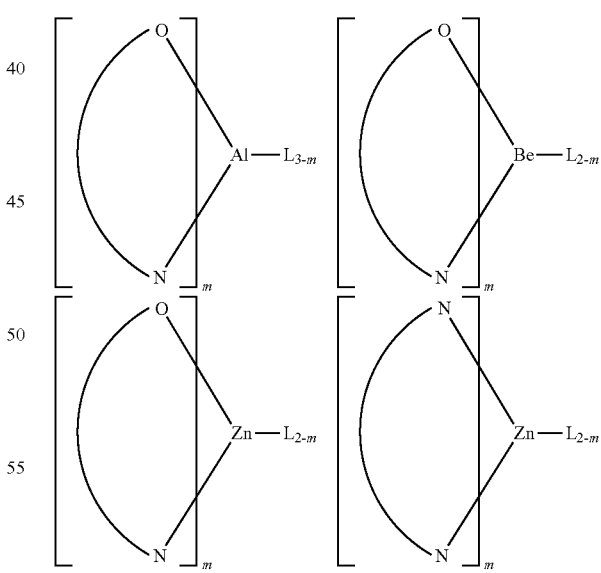

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
|---|---|---|
| Hole injection materials | | |
| Phthalocyanine and porphryin compounds | 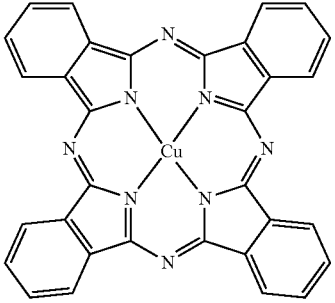 | Appl. Phys. Lett. 69, 2160 (1996) |
| Starburst triarylamines | 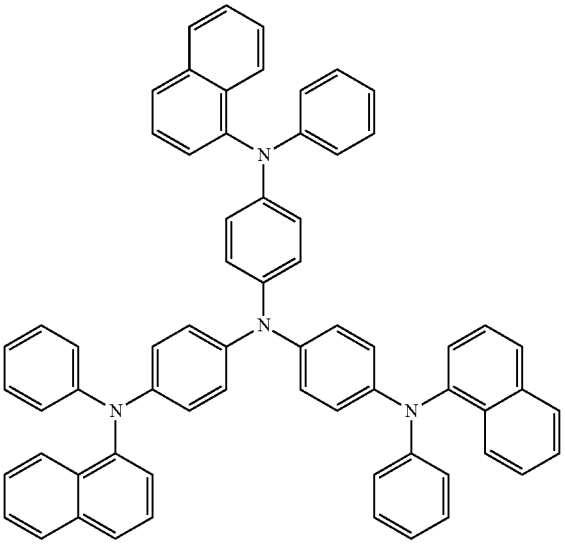 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| CF$_x$ Fluorohydrocarbon polymer | —$[CH_xF_y]_n$— | Appl. Phys. Lett. 78, 673 (2001) |
| Conducting polymers (e.g., PEDOT:PSS, polyaniline, polypthiophene) | 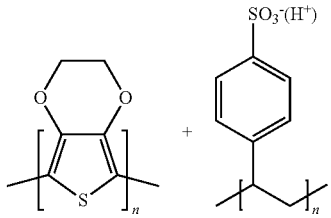 | Synth. Met. 87, 171 (1997) WO2007002683 |
| Phosphonic acid and sliane SAMs | 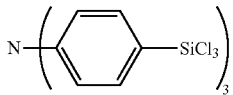 | US20030162053 |

TABLE 4-continued
| MATERIAL | EXAMPLES OF MATERIAL | PUBLICATIONS |
|---|---|---|
| Triarylamine or polythiophene polymers with conductivity dopants | 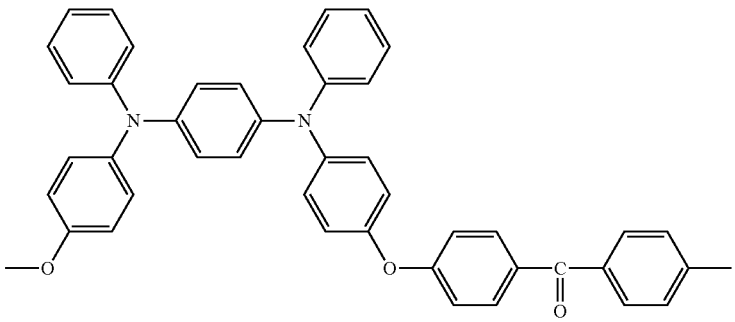 and 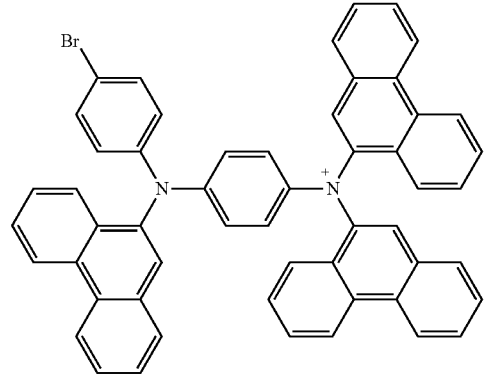 [SMILES: Brc1ccc(N(c2ccc(N(c3cc4ccccc4c4ccccc34)c3cc4ccccc4c4ccccc34)cc2)c2cc3ccccc3c3ccccc23)cc1]<br><br>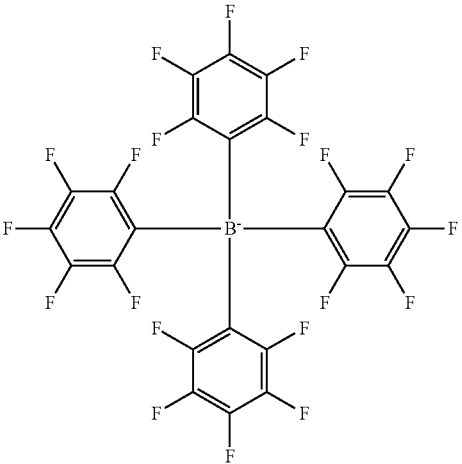 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 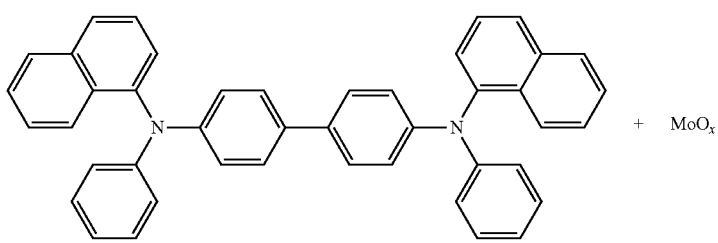 [SMILES: c1ccc(N(c2ccc(-c3ccc(N(c4ccccc4)c4cccc5ccccc45)cc3)cc2)c2cccc3ccccc23)cc1] + MoO$_x$ | US20050123751<br>SID Symposium Digest, 37, 923 (2006)<br>WO2009018009 |

TABLE 4-continued

| MATERIAL | EXAMPLES OF MATERIAL | PUBLICATIONS |
|---|---|---|
| n-type semiconducting organic complexes | (hexaazatriphenylene hexacarbonitrile structure) | US20020158242 |
| Metal organometallic complexes | (tris-cyclometalated Ir complex) | US20060240279 |
| Cross-linkable compounds | (bis-cyclometalated Ir complex with divinyl-triphenylamine substituent) | US20080220265 |
| Polythiophene based polymers and copolymers | (thiophene polymer with bis(ethoxy-ethoxy-ethoxy) side chains) | WO 2011075644<br>EP2350216 |

TABLE 4-continued
| MATERIAL | EXAMPLES OF MATERIAL | PUBLICATIONS |
|---|---|---|
| Hole transporting materials | | |
| Triarylamines (e.g., TPD, α-NPD) | 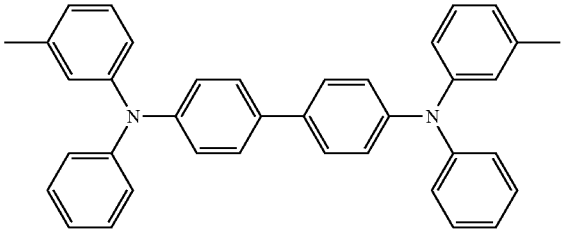 | Appl. Phys. Lett. 51, 913 (1987) |
| | 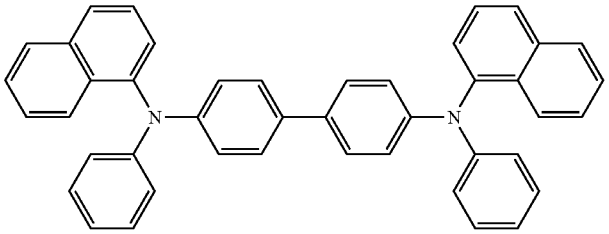 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 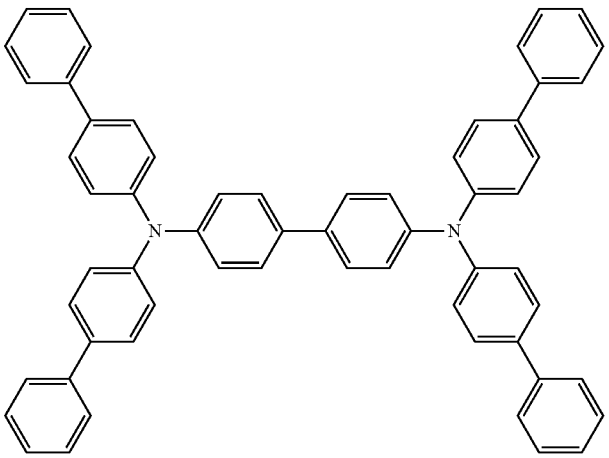 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 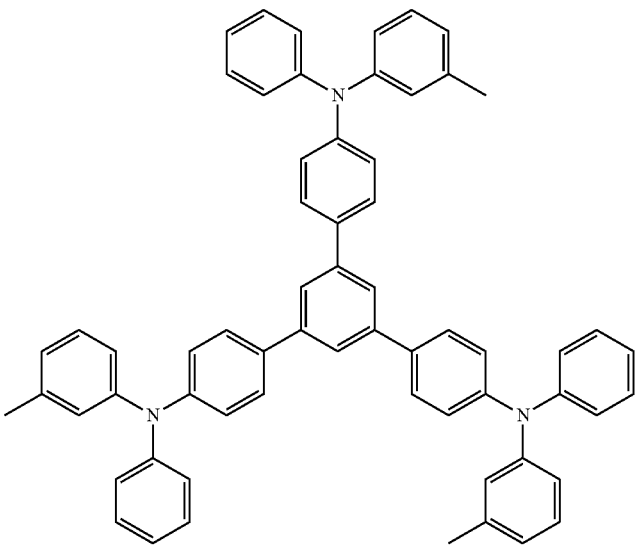 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 4-continued

| MATERIAL | EXAMPLES OF MATERIAL | PUBLICATIONS |
|---|---|---|
| | (structure) | Appl. Phys. Lett. 90, 183503 (2007) |
| | (structure) | Appl. Phys. Lett. 90, 183503 (2007) |
| Triaylamine on spirofluorene core | (structure) | Synth. Met. 91, 209 (1997) |

TABLE 4-continued

| MATERIAL | EXAMPLES OF MATERIAL | PUBLICATIONS |
|---|---|---|
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |
| Isoindole compounds | | Chem. Mater. 15, 3148 (2003) |

| MATERIAL | EXAMPLES OF MATERIAL | PUBLICATIONS |
|---|---|---|
| Metal carbene complexes | 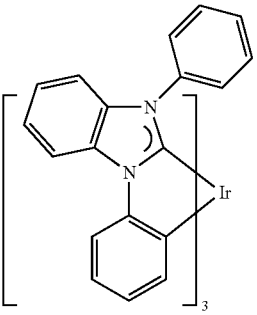 | US20080018221 |
Phosphorescent OLED host materials
Red hosts
| MATERIAL | EXAMPLES OF MATERIAL | PUBLICATIONS |
|---|---|---|
| Arylcarbazoles | 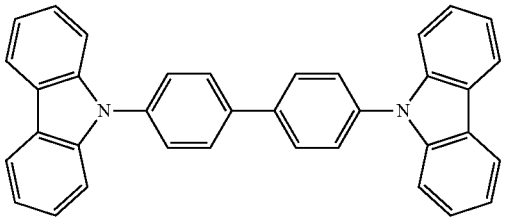 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq₃, BAlq) | 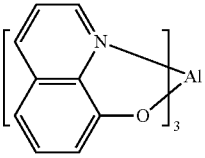 | Nature 395, 151 (1998) |
| | 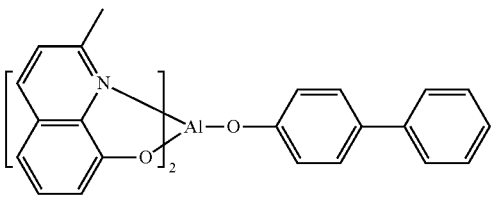 | US20060202194 |
| | 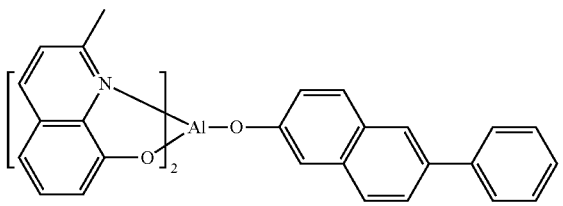 | WO2005014551 |
| | 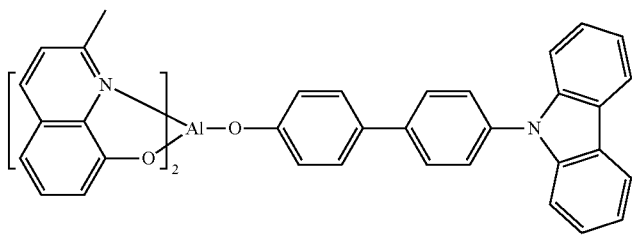 | WO2006072002 |

TABLE 4-continued

| MATERIAL | EXAMPLES OF MATERIAL | PUBLICATIONS |
|---|---|---|
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
|---|---|---|
| Arylcarbazoles | | Appl. Phys. Lett. 78, 1622 (2001) |

TABLE 4-continued
| MATERIAL | EXAMPLES OF MATERIAL | PUBLICATIONS |
|---|---|---|
| | 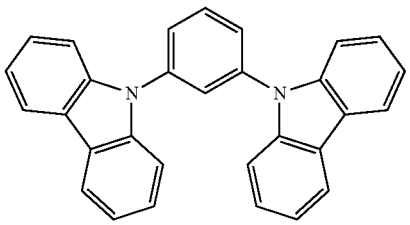 [SMILES: c1cc(-n2c3ccccc3c3ccccc32)cc(-n2c3ccccc3c3ccccc32)c1] | US20030175553 |
| | 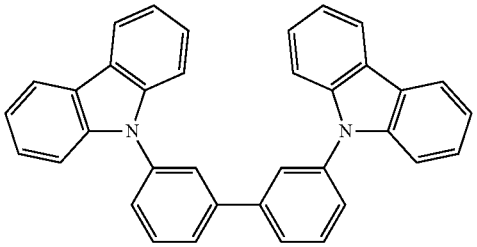 [SMILES: c1cc(-c2cccc(-n3c4ccccc4c4ccccc43)c2)cc(-n2c3ccccc3c3ccccc32)c1] | WO2001039234 |
| Aryltriphenylene compounds | 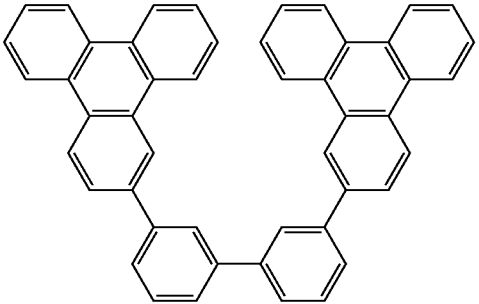 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 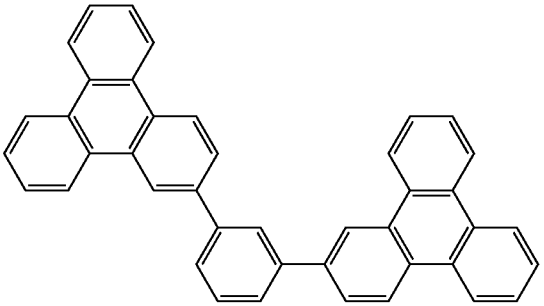 [SMILES: c1cc(-c2ccc3c4ccccc4c4ccccc4c3c2)cc(-c2ccc3c4ccccc4c4ccccc4c3c2)c1] | US20060280965 |
| | 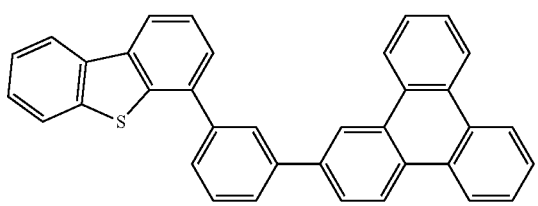 [SMILES: c1cc(-c2ccc3c4ccccc4c4ccccc4c3c2)cc(-c2cccc3c2sc2ccccc23)c1] | WO2009021126 |

TABLE 4-continued
| MATERIAL | EXAMPLES OF MATERIAL | PUBLICATIONS |
|---|---|---|
| Poly-fused heteroaryl compounds | 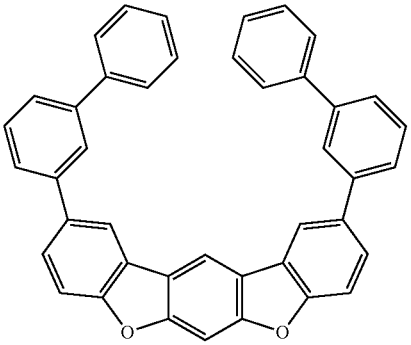 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 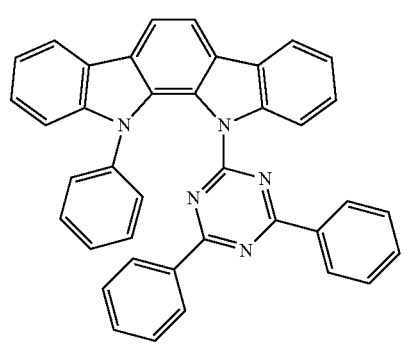 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 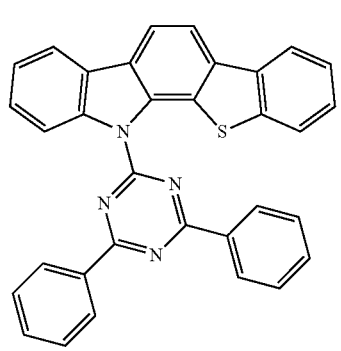 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 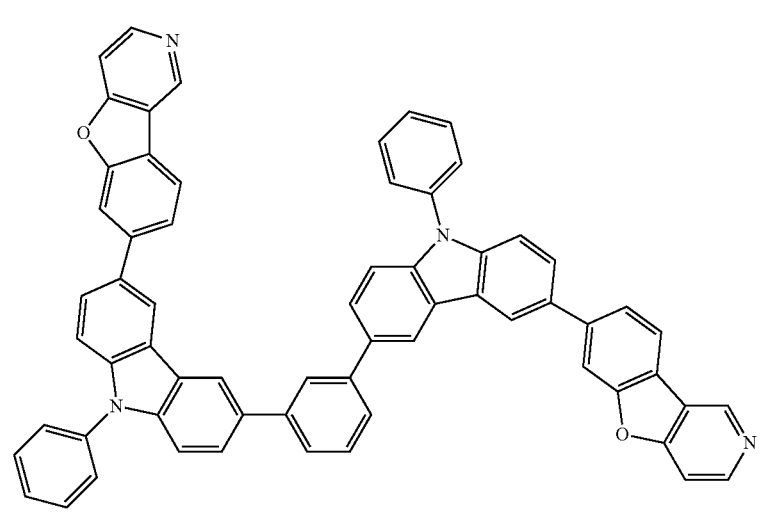 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 4-continued
| MATERIAL | EXAMPLES OF MATERIAL | PUBLICATIONS |
|---|---|---|
| | 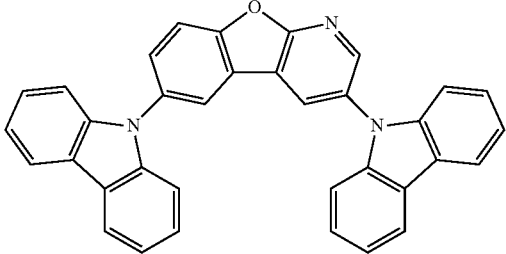 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 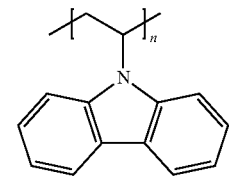 | Appl. Phys. Lett. 77, 2280 (2000) |
| Spirofluorene compounds | 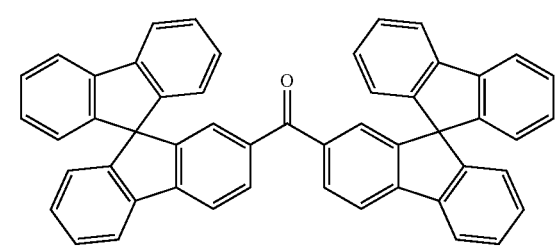 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 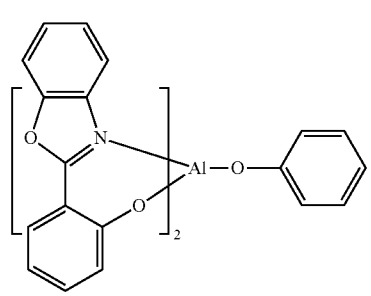 | WO2005089025 |
| | 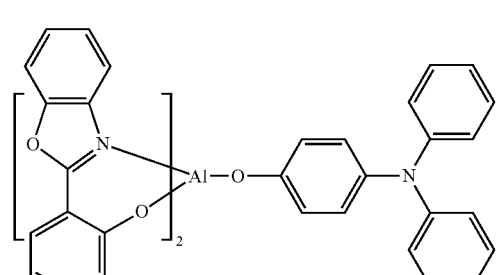 | WO2006132173 |
| | 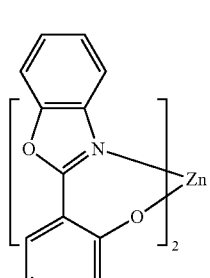 | JP200511610 |

TABLE 4-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |

TABLE 4-continued

| MATERIAL | EXAMPLES OF MATERIAL | PUBLICATIONS |
| --- | --- | --- |
|  |  | WO2004107822 |
| Tetraphenylene complexes |  | US20050112407 |
| Metal phenoxypyridine compounds |  | WO2005030900 |
| Metal coordination complexes (e.g., Zn, Al with N^N ligands) |  | US20040137268, US20040137267 |

Blue hosts

| Arylcarbazoles |  | Appl. Phys. Lett, 82, 2422 (2003) |
| --- | --- | --- |

TABLE 4-continued

| MATERIAL | EXAMPLES OF MATERIAL | PUBLICATIONS |
|---|---|---|
| | | US20070190359 |
| Dibenzothiophene/ Dibenzofuran-carbazole compounds | | WO2006114966, US20090167162 |
| | | US20090167162 |
| | | WO2009086028 |
| | | US20090030202, US20090017330 |

TABLE 4-continued
| MATERIAL | EXAMPLES OF MATERIAL | PUBLICATIONS |
|---|---|---|
|  | 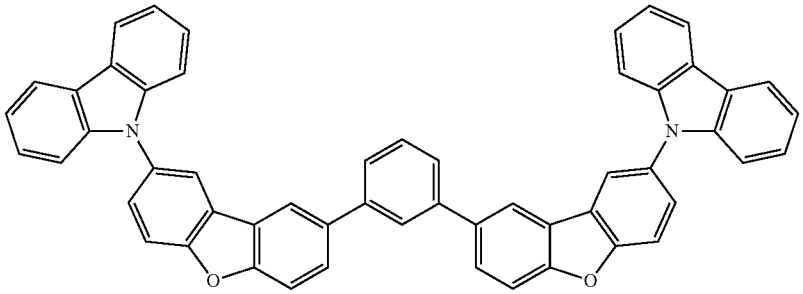 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 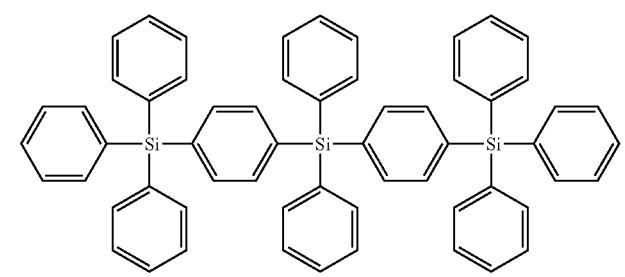 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
|  | 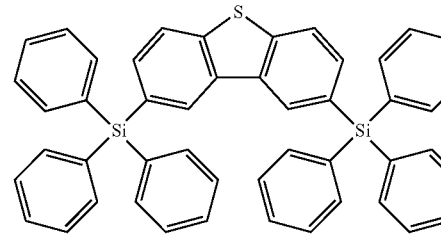 | WO2009003898 |
| Silicon/Germanium aryl compounds | 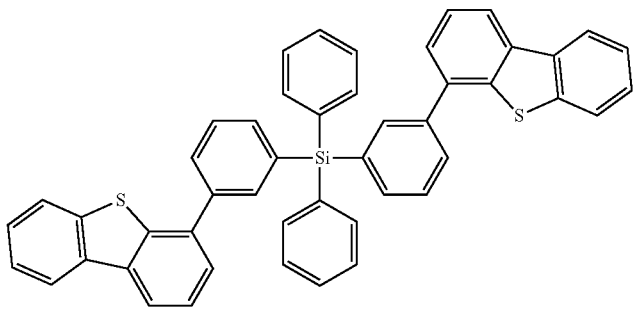 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester |  | WO2006100298 |
| Carbazole linked by non-conjugated groups | 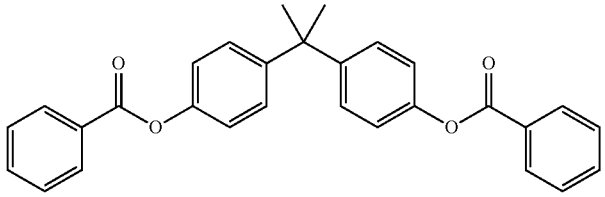 [SMILES: CC(C)(c1ccc(OC(=O)c2ccccc2)cc1)c1ccc(OC(=O)c2ccccc2)cc1] | US20040115476 |

TABLE 4-continued

| MATERIAL | EXAMPLES OF MATERIAL | PUBLICATIONS |
|---|---|---|
| Aza-carbazoles | | US20060121308 |
| High triplet metal organometallic complex | | U.S. Pat. No. 7,154,114 |ию

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |

TABLE 4-continued

| MATERIAL | EXAMPLES OF MATERIAL | PUBLICATIONS |
|---|---|---|
| | | US2006835469 |
| | | US20060202194 |
| | | US20060202194 |
| | | US20070087321 |
| | | US20080261076<br>US20100090591 |

TABLE 4-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| | | U.S. Pat. No. 7,232,618 |

TABLE 4-continued
| MATERIAL | EXAMPLES OF MATERIAL | PUBLICATIONS |
|---|---|---|
| Platinum(II) organometallic complexes | 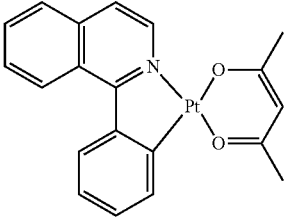 | WO2003040257 |
| | 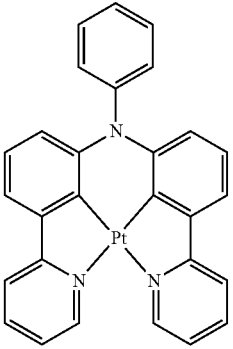 | US20070103060 |
| Osminum(III) complexes | 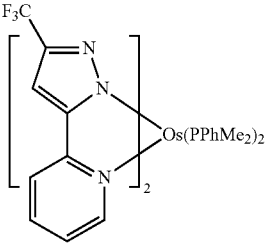 | Chem. Mater. 17, 3532 (2005) |
| Ruthenium(II) complexes | 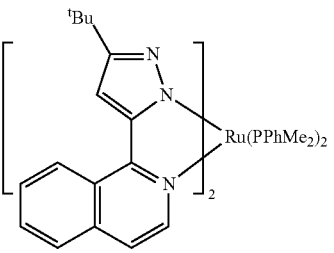 | Adv. Mater. 17, 1059 (2005) |
| Rhenium (I), (II), and (III) complexes | 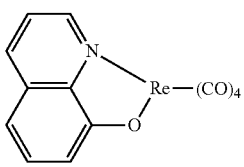 | US20050244673 |

TABLE 4-continued
| MATERIAL | EXAMPLES OF MATERIAL | PUBLICATIONS |
|---|---|---|
| | Green dopants | |
| Iridium(III) organometallic complexes | 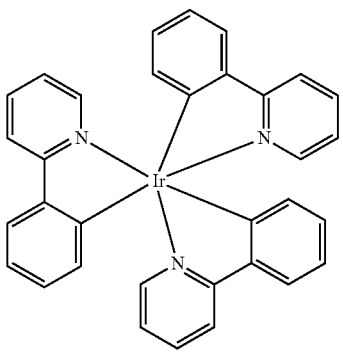<br>and its derivatives | Inorg. Chem. 40, 1704 (2001) |
| | 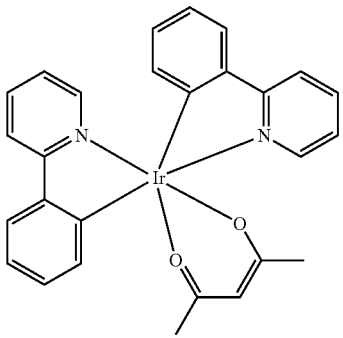 | US20020034656 |
| | 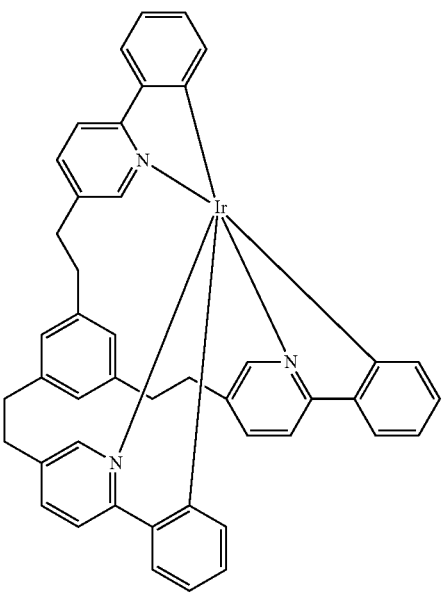 | U.S. Pat. No. 7,332,232 |

TABLE 4-continued
| MATERIAL | EXAMPLES OF MATERIAL | PUBLICATIONS |
|---|---|---|
| | 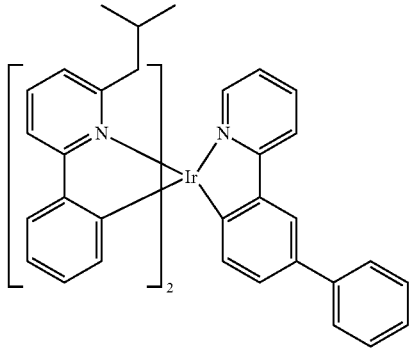 | US20090108737 |
| | 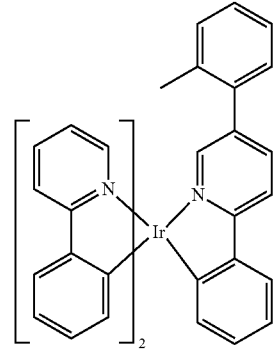 | WO2010028151 |
| | 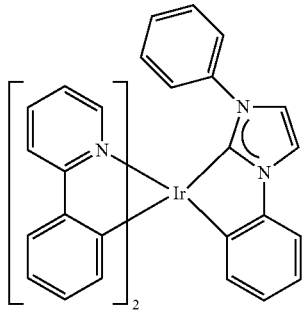 | EP1841834B |
| | 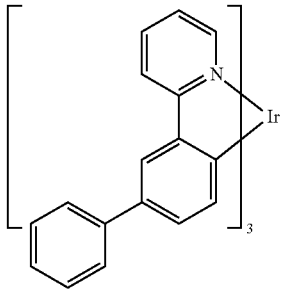 | US20060127696 |
| | 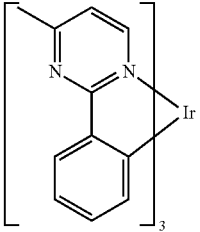 | US20090039776 |

TABLE 4-continued

| MATERIAL | EXAMPLES OF MATERIAL | PUBLICATIONS |
|---|---|---|
|  |  | U.S. Pat. No. 6,921,915 |
|  |  | US20100244004 |
|  |  | U.S. Pat. No. 6,687,266 |
|  |  | Chem. Mater. 16, 2480 (2004) |
|  |  | US20070190359 |

TABLE 4-continued

| MATERIAL | EXAMPLES OF MATERIAL | PUBLICATIONS |
|---|---|---|
| | | US 20060008670 JP2007123392 |
| | | WO2010086089, WO2011044988 |
| | | Adv. Mater. 16, 2003 (2004) |
| | | Angew. Chem. Int. Ed. 2006, 45, 7800 |
| | | WO2009050290 |
| | | US20090165846 |

TABLE 4-continued
| MATERIAL | EXAMPLES OF MATERIAL | PUBLICATIONS |
|---|---|---|
| | 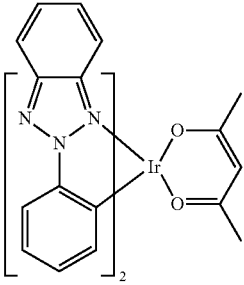 | US20080015355 |
| | 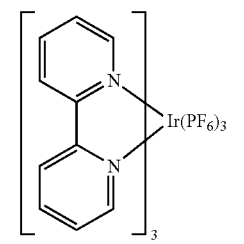 | US20010015432 |
| | 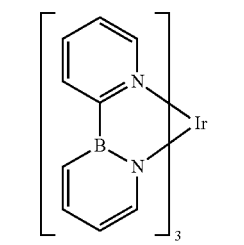 | US20100295032 |
| Monomer for polymeric metal organometallic compounds | 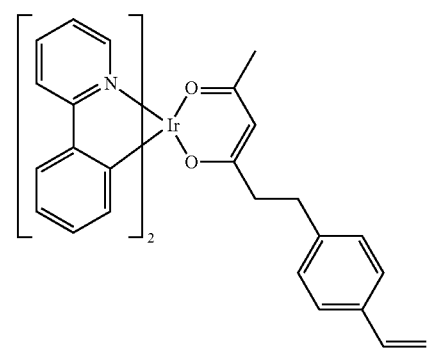 | U.S. Pat. No. 7,250,226, U.S. Pat. No. 7,396,598 |
| Pt(II) organometallic complexes, including polydentated ligands | 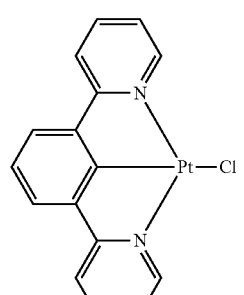 | Appl. Phys. Lett. 86, 153505 (2005) |

TABLE 4-continued
| MATERIAL | EXAMPLES OF MATERIAL | PUBLICATIONS |
|---|---|---|
| | 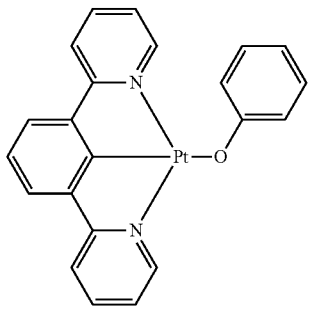 | Appl. Phys. Lett. 86, 153505 (2005) |
| | 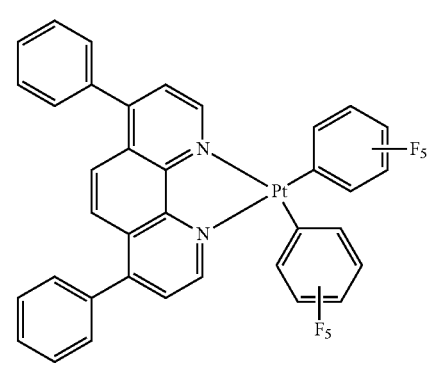 | Chem. Lett. 34, 592 (2005) |
| | 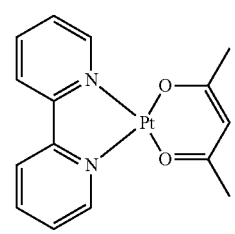 | WO2002015645 |
| | 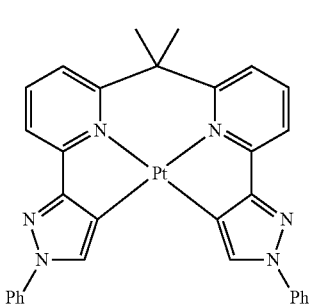 | US20060263635 |
| | 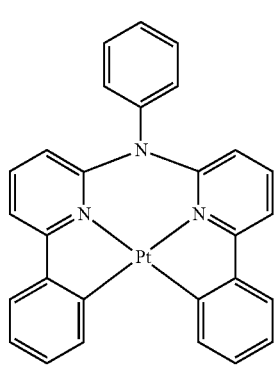 | US20060182992 US20070103060 |

TABLE 4-continued
| MATERIAL | EXAMPLES OF MATERIAL | PUBLICATIONS |
|---|---|---|
| Cu complexes | 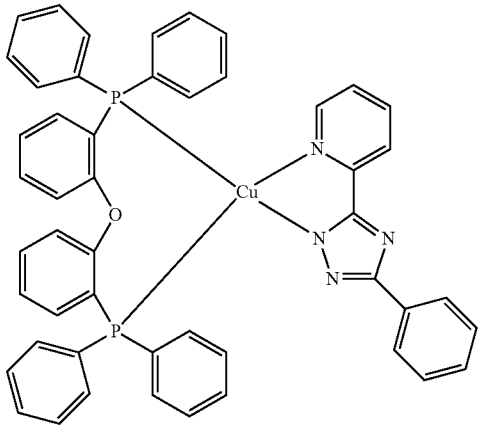 | WO2009000673 |
| | 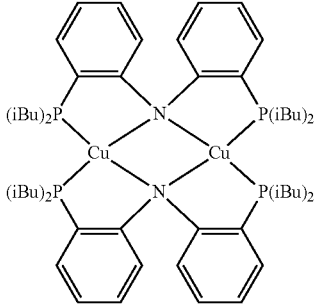 | US20070111026 |
| Gold complexes | 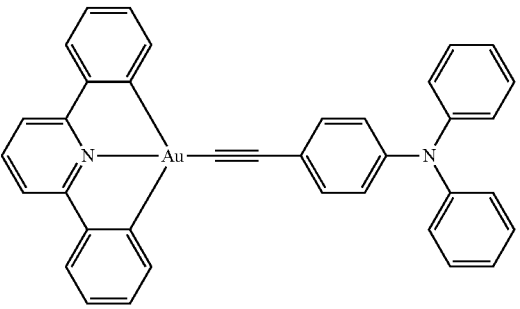 | Chem. Commun. 2906 (2005) |
| Rhenium(III) complexes | 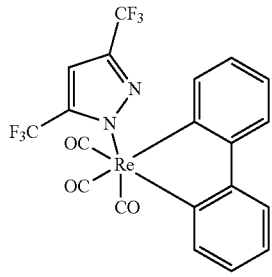 | Inorg. Chem. 42, 1248 (2003) |

TABLE 4-continued

| MATERIAL | EXAMPLES OF MATERIAL | PUBLICATIONS |
|---|---|---|
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE 4-continued
| MATERIAL | EXAMPLES OF MATERIAL | PUBLICATIONS |
|---|---|---|
| | Blue dopants | |
| Iridium(III) organometallic complexes | 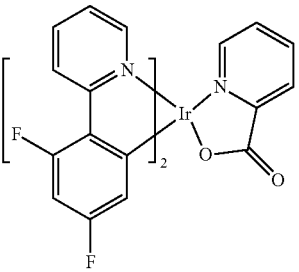 | WO2002002714 |
| | 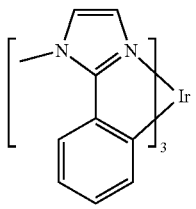 | WO2006009024 |
| | 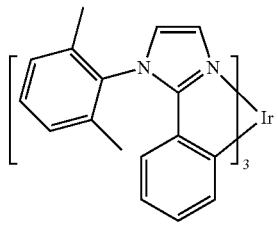 | US20060251923<br>US20110057559<br>US20110204333 |
| | 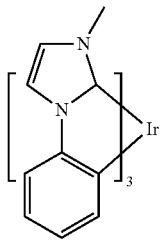 | U.S. Pat. No. 7,393,599,<br>WO2006056418,<br>US20050260441,<br>WO2005019373 |
| | 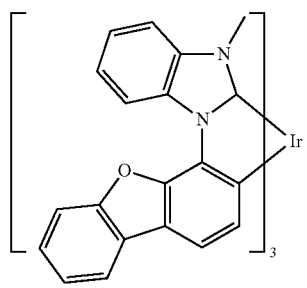 | U.S. Pat. No. 7,534,505 |

TABLE 4-continued

| MATERIAL | EXAMPLES OF MATERIAL | PUBLICATIONS |
|---|---|---|
| | | WO2011051404 |
| | | U.S. Pat. No. 7,445,855 |
| | | US20070190359, US20080297033 US20100148663 |
| | | U.S. Pat. No. 7,338,722 |
| | | US20020134984 |

| MATERIAL | EXAMPLES OF MATERIAL | PUBLICATIONS |
|---|---|---|
| | 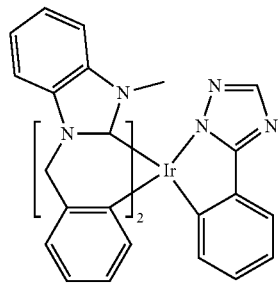 | Angew. Chem. Int. Ed. 47, 1 (2008) |
| | 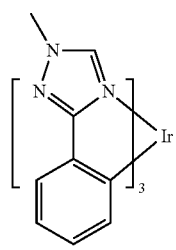 | Chem. Mater. 18, 5119 (2006) |
| | 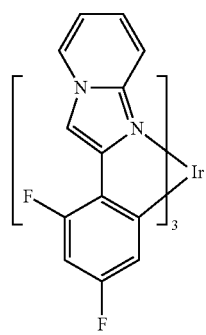 | Inorg. Chem. 46, 4308 (2007) |
| | 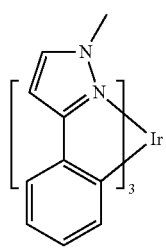 | WO2005123873 |
| | 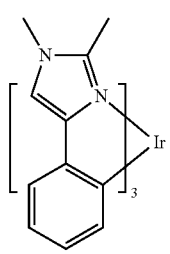 | WO2005123873 |

TABLE 4-continued
| MATERIAL | EXAMPLES OF MATERIAL | PUBLICATIONS |
|---|---|---|
| | 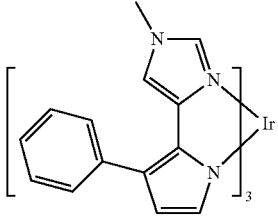 | WO2007004380 |
| | 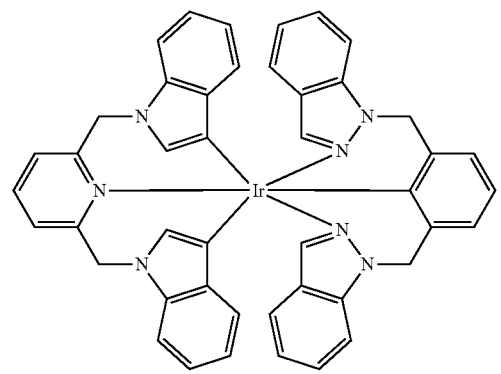 | WO2006082742 |
| Osmium(II) complexes | 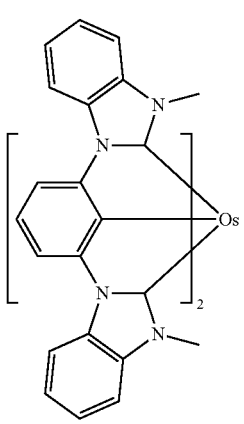 | U.S. Pat. No. 7,279,704 |
| | 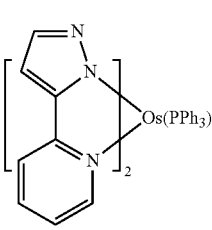 | Organometallics 23, 3745 (2004) |
| Gold complexes | 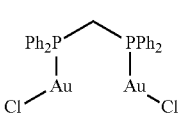 | Appl. Phys. Lett. 74, 1361 (1999) |
| Platinum(II) complexes | 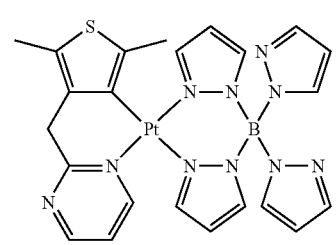 | WO2006098120, WO2006103874 |

TABLE 4-continued

| MATERIAL | EXAMPLES OF MATERIAL | PUBLICATIONS |
|---|---|---|
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

| MATERIAL | EXAMPLES OF MATERIAL | PUBLICATIONS |
|---|---|---|
| Triphenylene compounds | 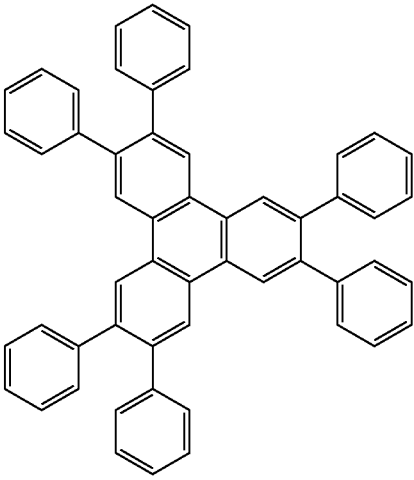 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 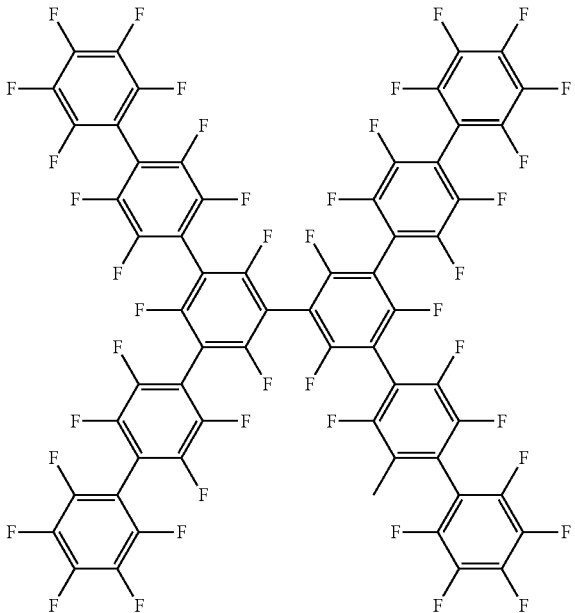 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 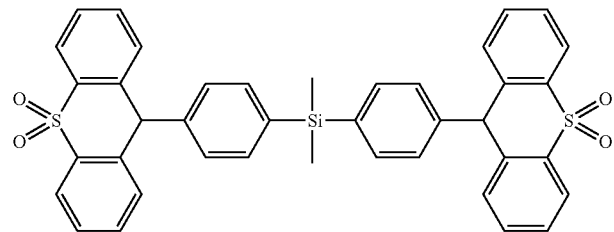 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 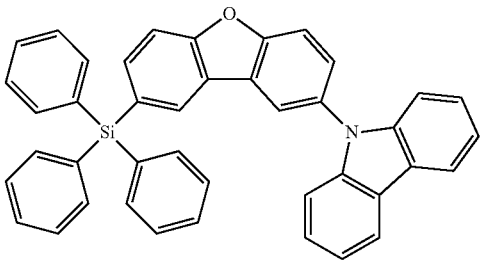 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 4-continued
| MATERIAL | EXAMPLES OF MATERIAL | PUBLICATIONS |
|---|---|---|
| Aza-carbazoles | 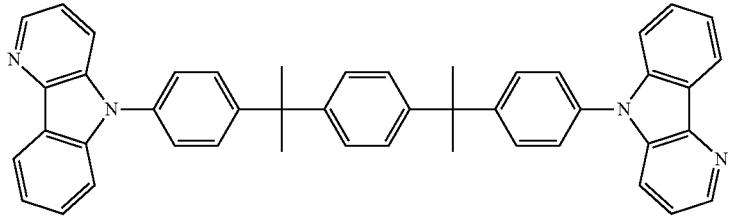 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 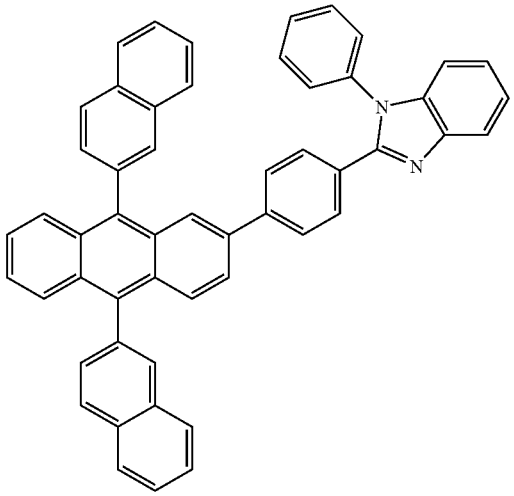 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 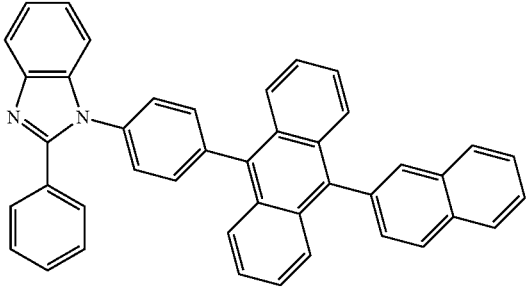 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 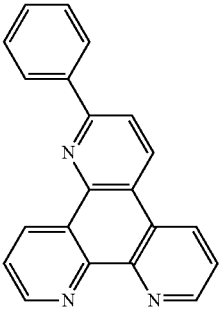 [SMILES: c1ccc(-c2ccc3c4cccnc4c4ncccc4c3n2)cc1] | US20090115316 |

TABLE 4-continued

| MATERIAL | EXAMPLES OF MATERIAL | PUBLICATIONS |
|---|---|---|
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 4-continued
| MATERIAL | EXAMPLES OF MATERIAL | PUBLICATIONS |
|---|---|---|
| | 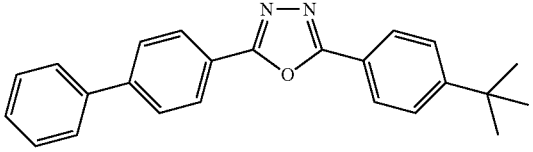 [SMILES: CC(C)(C)c1ccc(-c2nnc(-c3ccc(-c4ccccc4)cc3)o2)cc1] | Appl. Phys. Lett. 55, 1489 (1989) |
| | 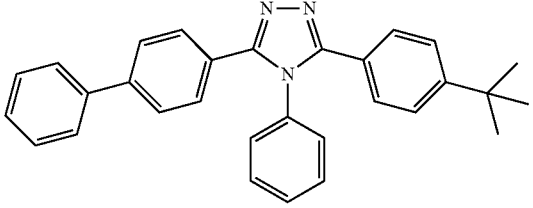 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 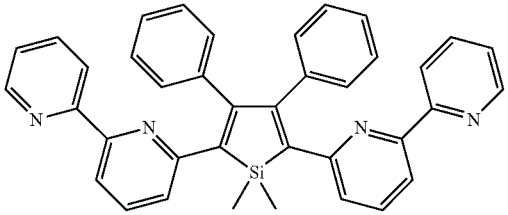 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 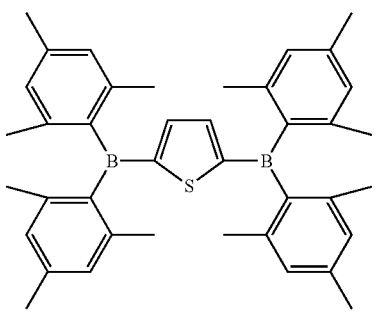 | J. Am. Chem. Soc. 120, 9714 (1998) |
| Fluorinated aromatic compounds | 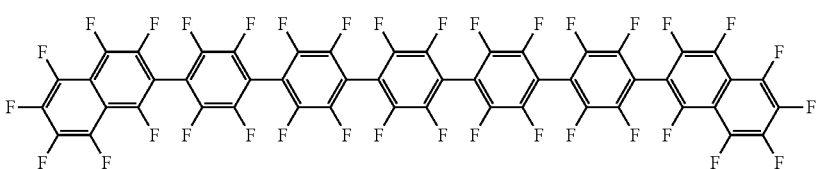 [SMILES: Fc1c(F)c(-c2c(F)c(F)c(-c3c(F)c(F)c(-c4c(F)c(F)c5c(F)c(F)c(F)c(F)c5c4F)c(F)c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 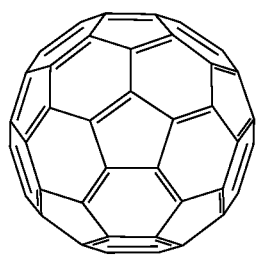 [SMILES: c1cc2c3ccc4c5ccc6c7ccc8c9ccc%10c1c1c2c2c3c4c3c5c6c4c7c8c5c9c%10c1c1c2c3c4c51] | US20090101870 |

TABLE 4-continued

| MATERIAL | EXAMPLES OF MATERIAL | PUBLICATIONS |
|---|---|---|
| Triazine complexes | | US20040036077 |
| Zn (N^N) complexes | | U.S. Pat. No. 6,528,187 |

EXPERIMENTAL

Chemical abbreviations used throughout this document are as follows: dba is dibenzylideneacetone, EtOAc is ethyl acetate, dppf is 1,1'-bis(diphenylphosphino)ferrocene, DCM is dichloromethane, SPhos is dicyclohexyl(2',6'-dimethoxy-[1,1'-biphenyl]-3-yl)phosphine, THF is tetrahydrofuran.

Synthesis of Compound 1

Compound 1

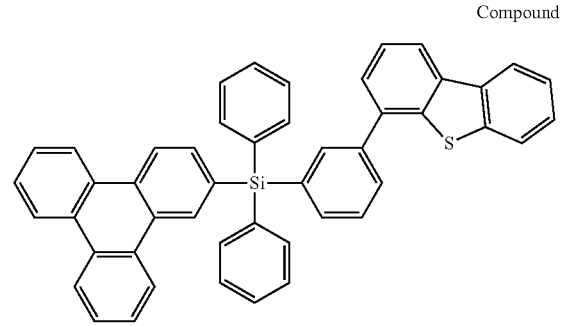

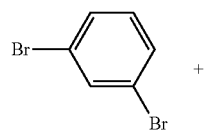

+

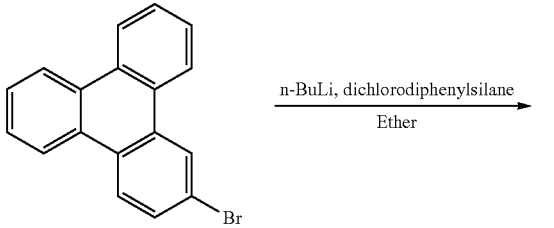

-continued

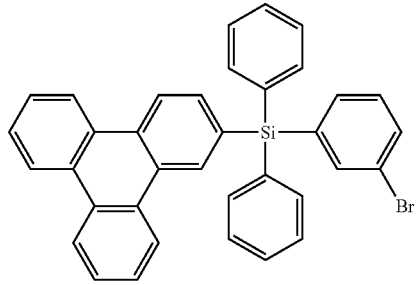

Into a suspension of 2-bromotriphenylene (7.28 g, 23.70 mmol) in ether (50 mL) was added n-butyllithium solution in hexane (14.81 mL, 23.70 mmol) dropwise at −78° C. The suspension was gradually warmed to 0° C. and stirred for 3 hours to yield a solution of triphenylenyllithium. In a separate flask a solution of 3-bromophenyllithium was prepared by dropwise addition of n-butyllithium solution in hexane (14.81 mL, 23.70 mmol) into a solution of 1,3-dibromobenzene (2.87 mL, 23.70 mmol) in ether (50 mL). The solution was stirred at this temperature for 2.5 hours before being transferred into a solution of dichlorodiphenylsilane (4.88 mL, 23.70 mmol) in ether (30 mL) at −78° C. After stirring for another 2 h, the triphenylenyllithium solution prepared above was introduced dropwise into the flask containing the dichlorophenylsilane. The reaction mixture was allowed to gradually warm to room temperature and was stirred overnight. The mixture was quenched with water and the organic phase was isolated. Upon evaporation of the solvent, the residue was purified by column chromatography on silica gel with hexane/DCM (85/15, v/v) as eluent to yield (3-bromophenyl)diphenyl(triphenylen-2-yl)silane (8.5 g, 75%) as a white powder.

Synthesis of Compound 2

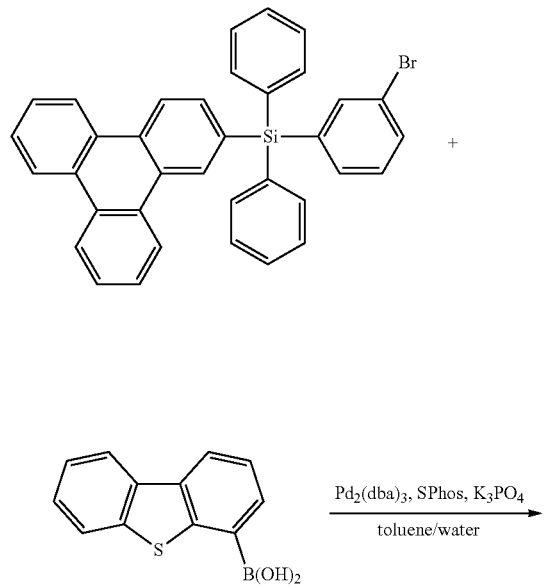

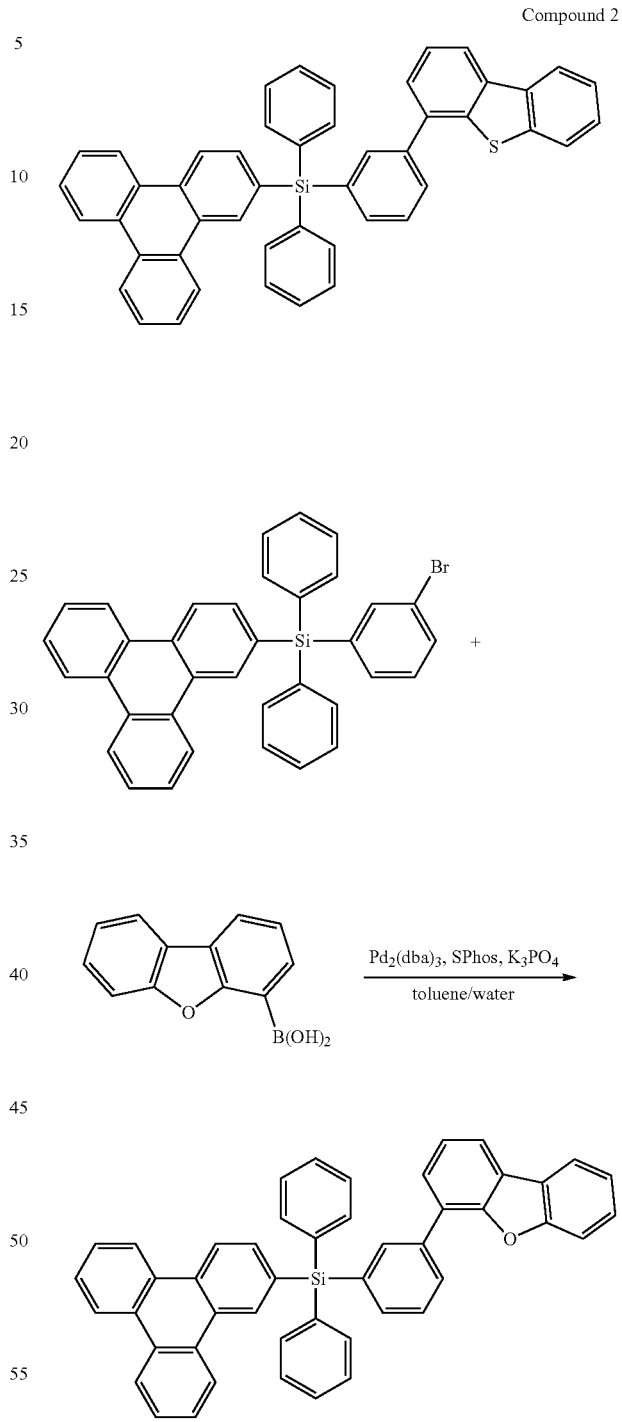

A solution of dibenzo[b,d]thiophen-4-ylboronic acid (1.573 g, 6.90 mmol), (3-bromophenyl)diphenyl(triphenylen-2-yl)silane (3, 5.30 mmol), $Pd_2(dba)_3$ (0.097 g, 0.106 mmol), SPhos (0.087 g, 0.212 mmol) and $K_3PO_4$ (3.38 g, 15.91 mmol) in toluene (50 mL) and water (7 mL) was stirred at 100° C. under nitrogen overnight. After cooling to room temperature, the organic phase was isolated, the aqueous phase was extracted with DCM, and the combined organic solution was dried over $Na_2SO_4$. Upon evaporation of the solvent, the residue was purified by column chromatography on silica gel with hexane/dichlromethane (9/1 to 8.5/1.5, v/v) as eluent to yield Compound 1 (2.4 g, 68%) as a white solid.

A solution of (3-bromophenyl)diphenyl(triphenylen-2-yl)silane (2.9 g, 5.13 mmol), dibenzo[b,d]furan-4-ylboronic acid (1.196 g, 5.64 mmol), $Pd_2(dba)_3$ (0.094 g, 0.10 mmol), SPhos (90 mg, 0.22 mmol) and $K_3PO_4$ (2.72 g, 12.82 mmol) in toluene (150 mL) and water (10 mL) was refluxed under nitrogen overnight. After evaporation off the solvent, the residue was purified by column chromatography on silica gel with hexane/DCM (4/1, v/v) as eluent to yield Compound 2 (1.5 g, 44%) as a white solid.

Synthesis of Compound 3

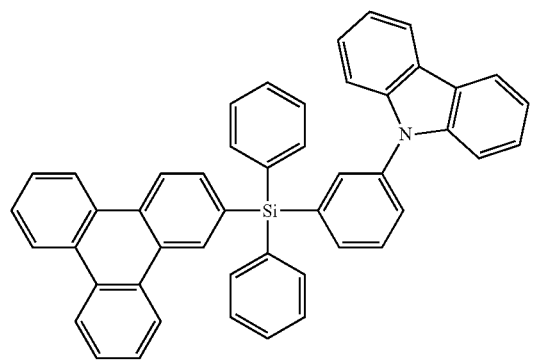

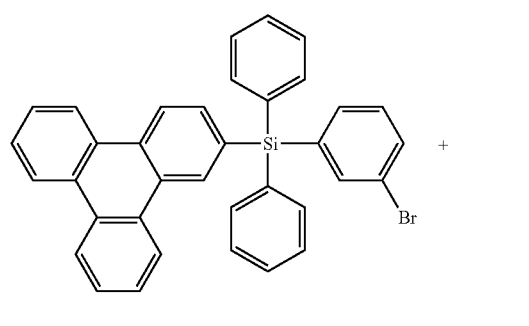

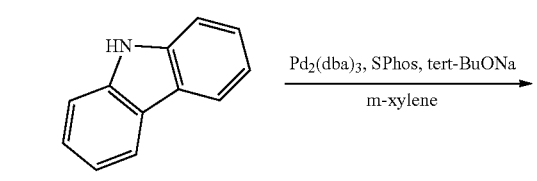

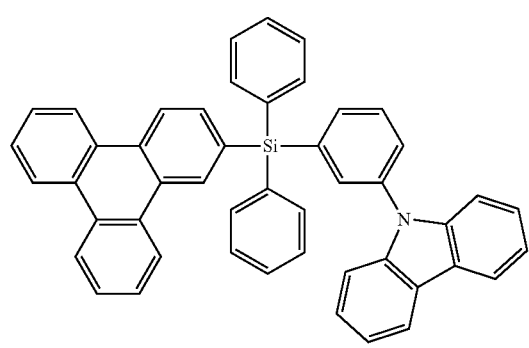

A mixture of (3-bromophenyl)diphenyl(triphenylen-2-yl)silane (3.52 g, 6.22 mmol), 9H-carbazole (1.249 g, 7.47 mmol), Pd$_2$(dba)$_3$ (0.114 g, 0.124 mmol), SPhos (0.102 g, 0.249 mmol), and sodium tert-butoxide (1.794 g, 18.67 mmol) in m-xylene (100 mL) was refluxed under nitrogen overnight. After cooling to room temperature, it was filtered through a plug of Celite®. The organic solution was concentrated, and the residue was purified by column chromatography on silica gel with hexane/DCM (85/15, v/v) as eluent and precipitation in methanol to yield Compound 3 (3.5 g, 86%) as a white powder.

Synthesis of Compound 4

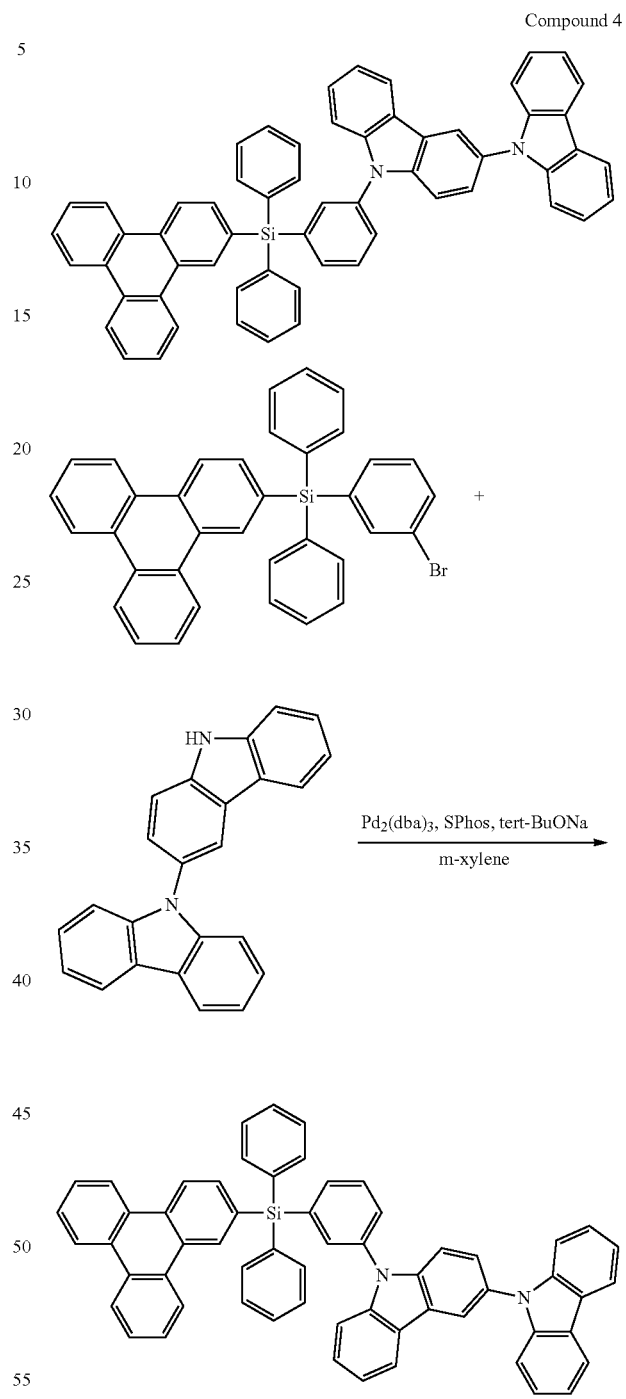

A mixture of (3-bromophenyl)diphenyl(triphenylen-2-yl)silane (3 g, 5.30 mmol), 9H-3,9'-bicarbazole (2.116 g, 6.37 mmol), Pd$_2$(dba)$_3$ (0.097 g, 0.106 mmol), SPhos (0.087 g, 0.212 mmol), and sodium tert-butoxide (1.529 g, 15.91 mmol) in m-xylene (100 mL) was refluxed under nitrogen at 165° C. overnight. After cooling to room temperature, it was filtered through a short plug of Celite®. Upon evaporation off the solvent, the residue was purified by column chromatography on silica gel with hexane/DCM(8/2 to 3/1, v/v) as eluent to yield Compound 4 (4.0 g, 92%) as a white solid.

Synthesis of Compound 5

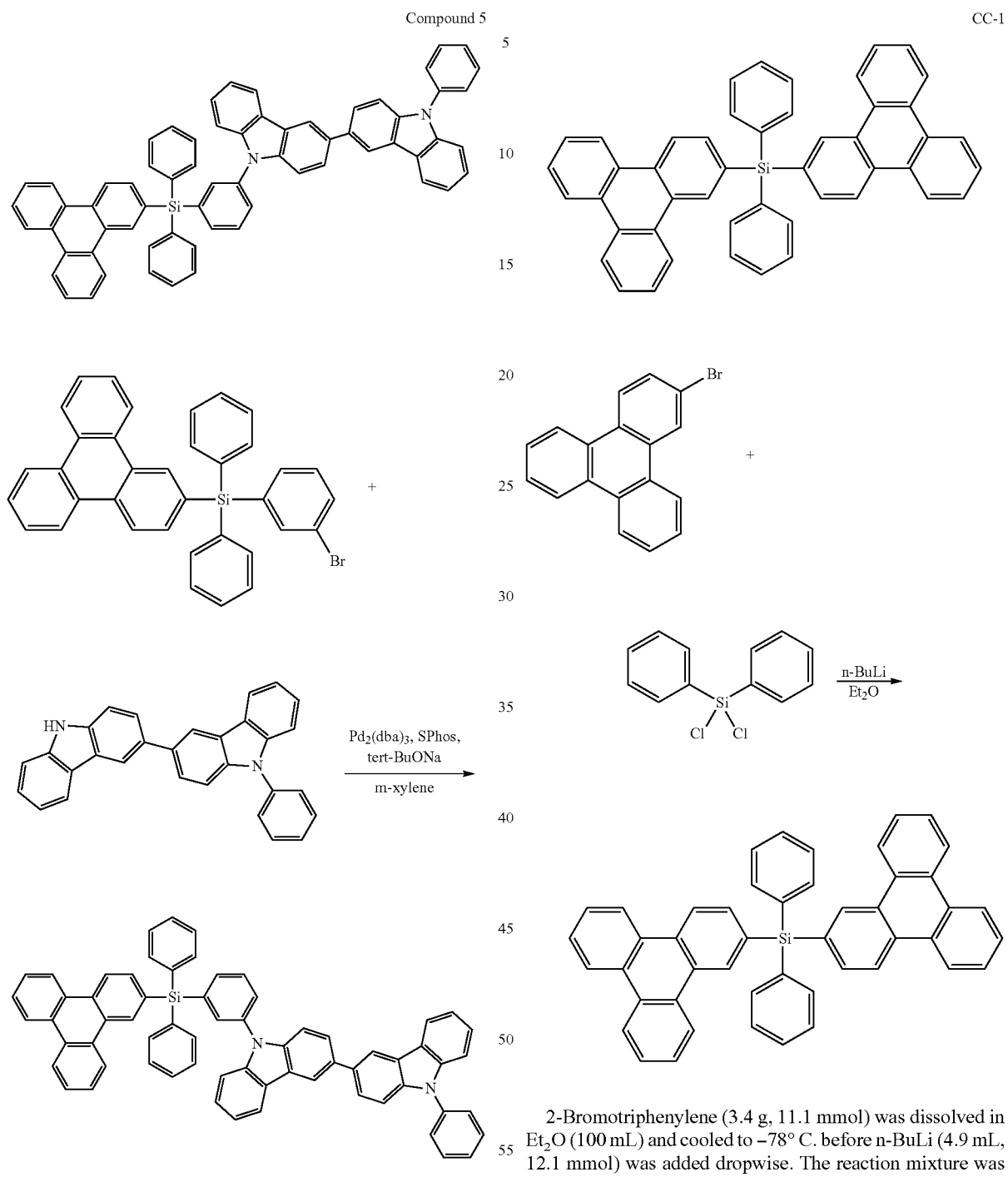

Synthesis of Comparative Compound 1 (CC-1)

A solution of (3-bromophenyl)diphenyl(triphenylen-2-yl)silane (2.5 g, 4.42 mmol), 9-phenyl-9H,9'H-3,3'-bicarbazole (1.806 g, 4.42 mmol), Pd$_2$(dba)$_3$ (0.081 g, 0.088 mmol), SPhos (0.073 g, 0.177 mmol) and sodium tert-butoxide (1.274 g, 13.26 mmol) in m-xylene (80 mL) was refluxed under nitrogen overnight. After cooling to room temperature, it was passed through a short plug of Celite®. Upon evaporation off the solvent, the residue was purified by column chromatography on silica gel with hexane/DCM (4/1 to 3/2, v/v) as eluent to yield Compound 5 as a white powder.

2-Bromotriphenylene (3.4 g, 11.1 mmol) was dissolved in Et$_2$O (100 mL) and cooled to −78° C. before n-BuLi (4.9 mL, 12.1 mmol) was added dropwise. The reaction mixture was allowed to slowly warm to −0° C. and stirred for 30 minutes before it was re-cooled to −78° C. Diphenyldichlorosilane (1.1 mL, 5.3 mmol) in 20 mL of Et$_2$O was added dropwise to the reaction mixture. After slowly warming to room temperature overnight the thick mixture was refluxed for 3 h. After cooling to room temperature, 300 mL of water was added with rapid stirring and the precipitate was filtered from the biphasic mixture, washing with Et$_2$O. The solid was dissolved in DCM and filtered through a plug of silica gel on a frit. Removal of the solvent yielded CC-1 (2.4 g, 72%) as a white solid.

Synthesis of Comparative Compound 2 (CC-2)

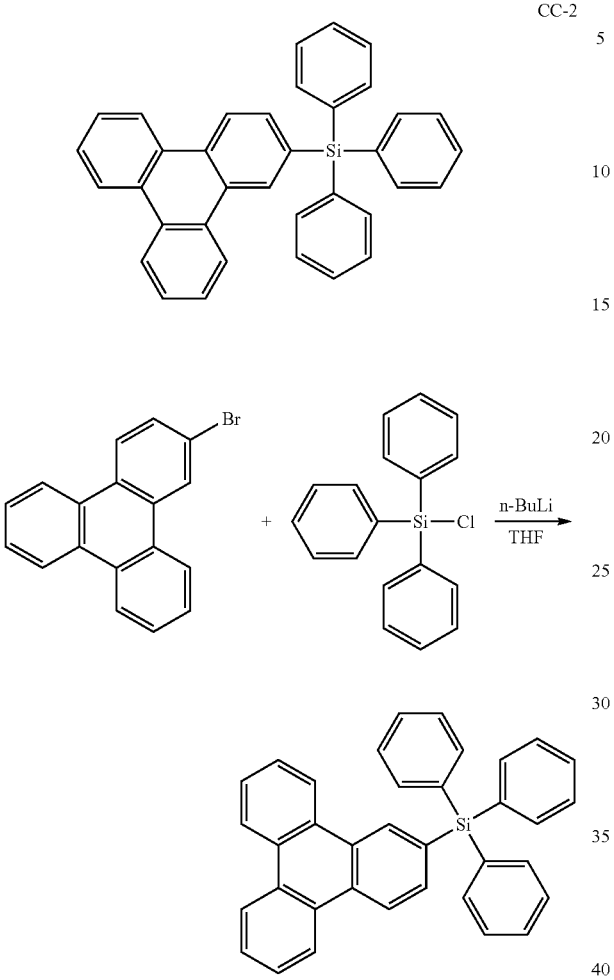

2-Bromotriphenylene (5.5 g, 14.3 mmol) was dissolved in THF (50 mL) and cooled to −78° C. before n-BuLi (5.7 mL, 14.3 mmol) was added dropwise. The reaction mixture was allowed to slowly warm to −30° C. before it was recooled to −78° C. Chlorotriphenylsilane (3.8 g, 13.0 mmol) was dissolved in 20 mL of THF and added dropwise to the reaction mixture which was subsequently allowed to slowly warm to room temperature overnight and further heated to 40° C. for 2 h. After cooling to room temperature, the reaction was quenched with MeOH and NH$_4$Cl (aq.), extracted three times with EtOAc (50 mL), dried and rotovapped to give 7.8 g of a yellow solid. The crude material was chromatographed on silica hexane/DCM (9/1, v/v) as eluent. Recrystallization from DCM/hexane gave CC-2 (5.5 g, 87%) as a white crystalline solid.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having formula:

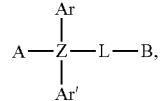

Formula I wherein Ar and Ar' are independently selected from the group consisting of phenyl, biphenyl, naphthalene, dibenzothiophene and dibenzofuran, which are optionally further substituted;

Z is selected from Si and Ge;

L is a single bond or comprises an aryl or heteroaryl group having from 5-20 carbon atoms, which is optionally further substituted;

A is a group directly bonded to Z and is selected from the group consisting of triphenylene, tetraphenylene, pyrene, naphthalene, fluoranthene, chrysene, phenanthrene, azatriphenylene, azatetraphenylene, azapyrene, azanaphthalene, azafluoranthene, azachrysene, azaphenanthrene, and combinations thereof, which are optionally further substituted with one or more groups selected from the group consisting of hydrogen, deuterium, halide, alkyl, cycloalkyl, heteroalkyl, arylalkyl, aryl, aryloxy, and combinations thereof;

B is a group selected from the group consisting of carbazole, dibenzoselenophene, aza-carbazole, aza-dibenzofuran, aza-dibenzothiophene, azadibenzoselenophene, and combinations thereof, which are optionally further substituted with one or more groups selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein the substitution is optionally fused to the carbazole, dibenzoselenophene, aza-carbazole, aza-dibenzofuran, aza-dibenzothiophene or aza-dibenzoselenophene group wherein when B is carbazole, the carbazole group is connected to L through a ring carbon.

2. The compound of claim 1, wherein A is

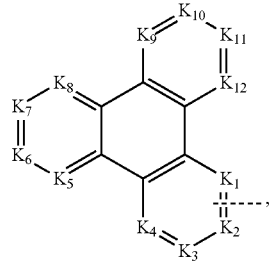

wherein K$_1$ to K$_{12}$ are independently selected from N and C—R'; and wherein R' is selected from the group consisting of hydrogen, deuterium, halide, alkyl, cycloalkyl, heteroalkyl, arylalkyl, aryl, aryloxy, and combinations thereof, wherein R' does not exist on one of K$_1$ to K$_4$ when said one of K$_1$ to K$_4$ is bonded to Z is C.

3. The compound of claim 1, wherein B is selected from the group consisting of:

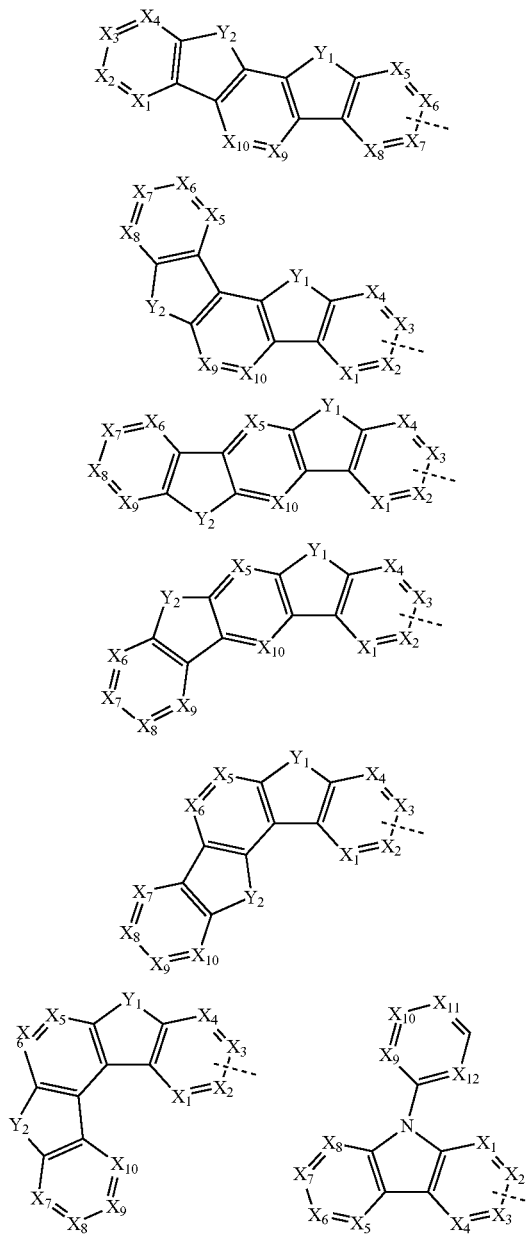

wherein $X_1$-$X_{15}$ are independently selected from the group consisting of N and C—R", wherein R" is selected from a group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein R" does not exist on one of $X_1$ to $X_8$ when said one of $X_1$ to $X_8$ that is bonded to L is C; and wherein $Y_1$ and $Y_2$ are independently selected from the group consisting of O, S, and Se.

4. The compound of claim 1, wherein A is selected from the group consisting of:

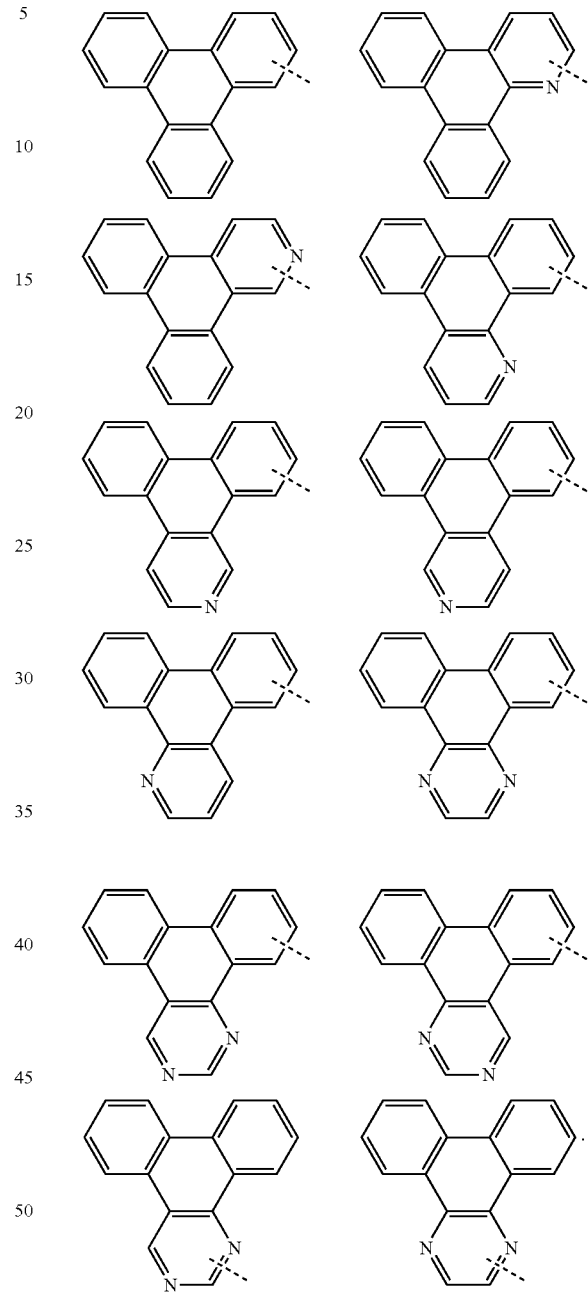

5. The compound of claim 1, wherein A is selected from the group consisting of:

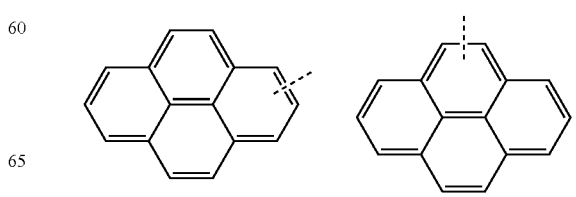

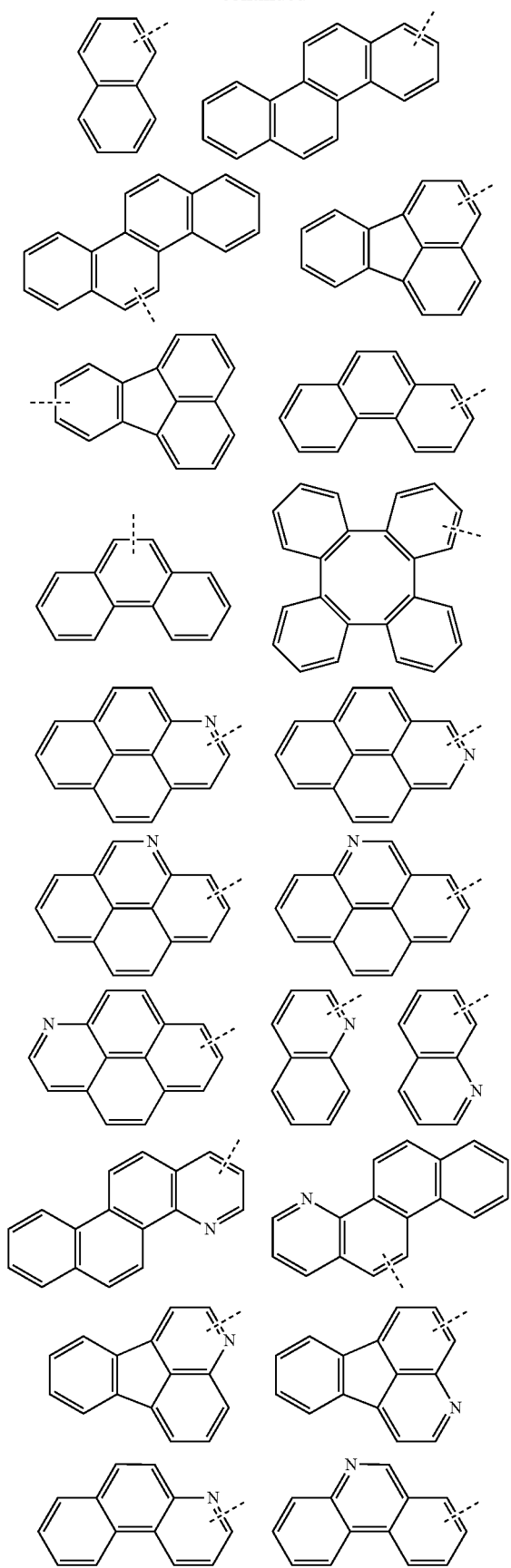
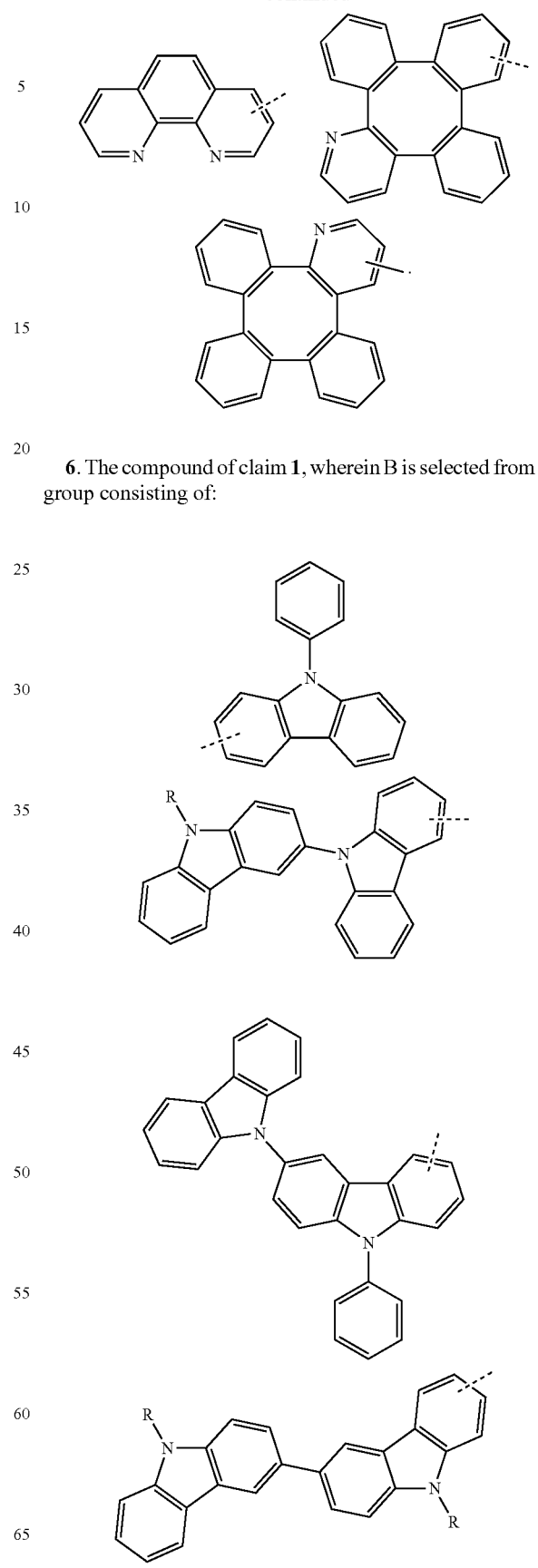
6. The compound of claim 1, wherein B is selected from the group consisting of:

-continued

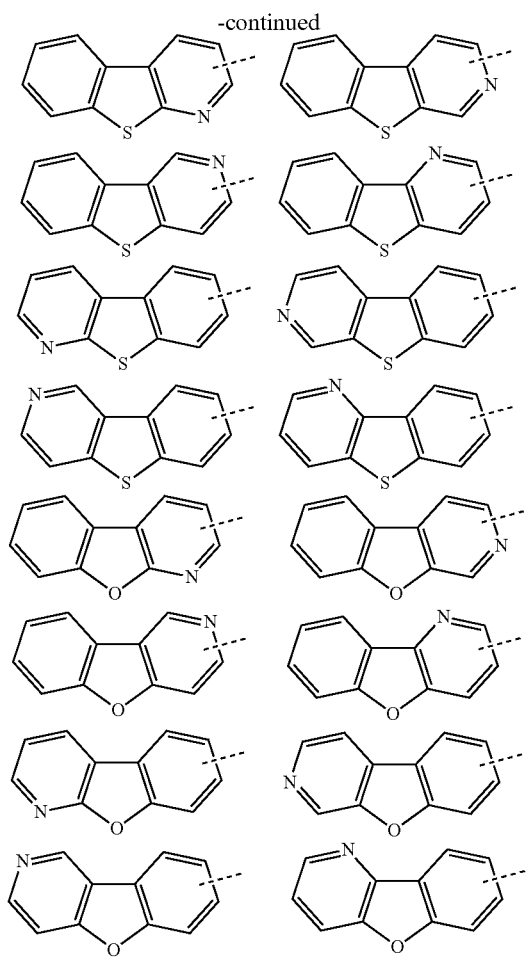

wherein $Y_1$ is selected from the group consisting of O, S, and Se;

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

7. The compound of claim 1, wherein L is independently selected from the group consisting of:

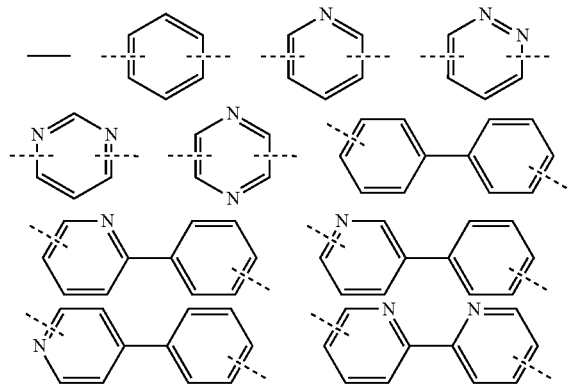

-continued

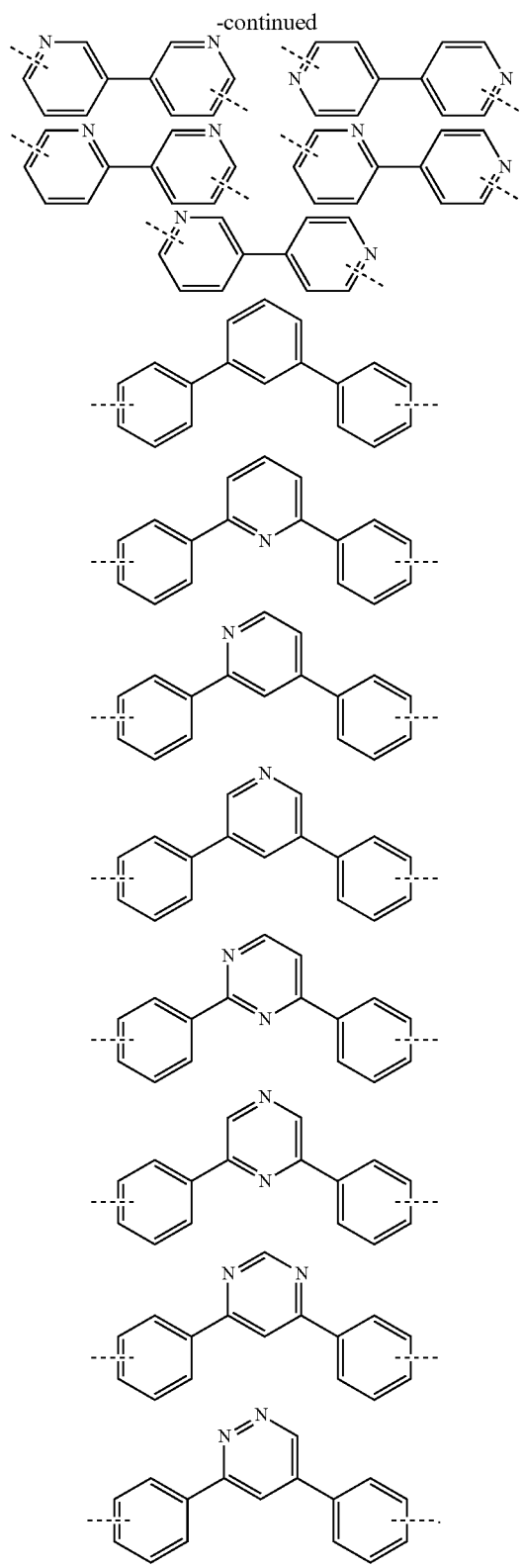

8. The compound of claim 1, wherein A is tripheynylene.

9. The compound of claim 1, wherein A is pyrene.

10. The compound of claim 1, wherein Ar and Ar' are phenyl.

11. The compound of claim 1, wherein L is phenyl.

12. The compound of claim 1, whereto the compound is selected from the group consisting of:
Compound 6
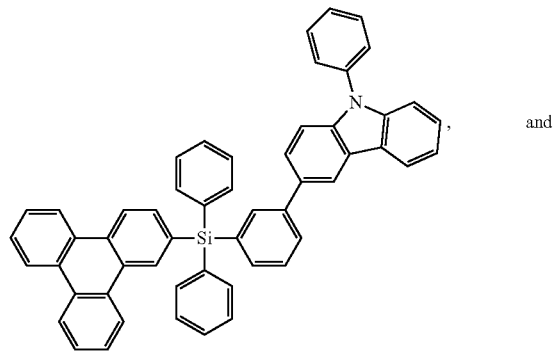
and
Compound 12
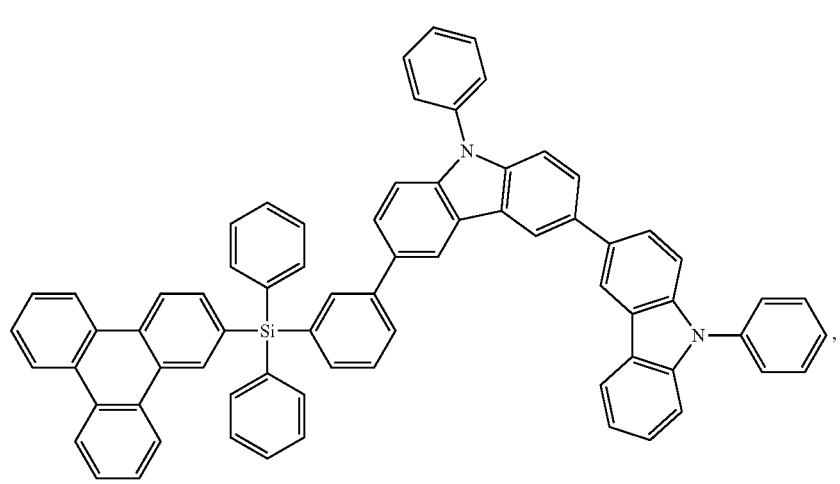
Compound 17
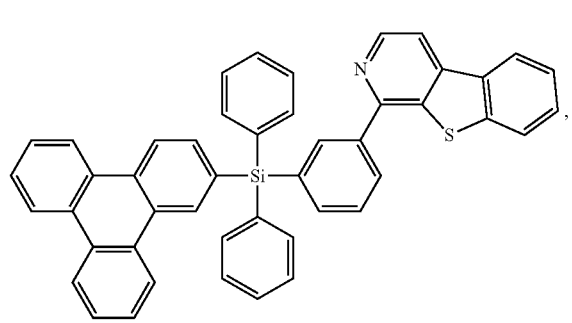
Compound 18
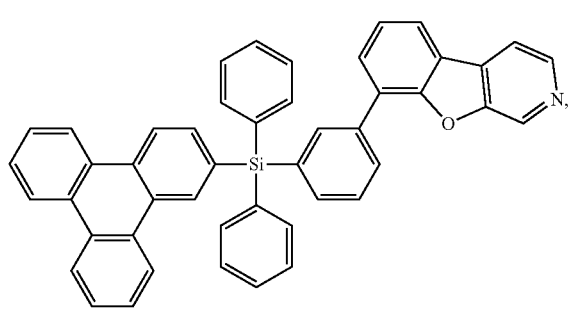

Compound 20

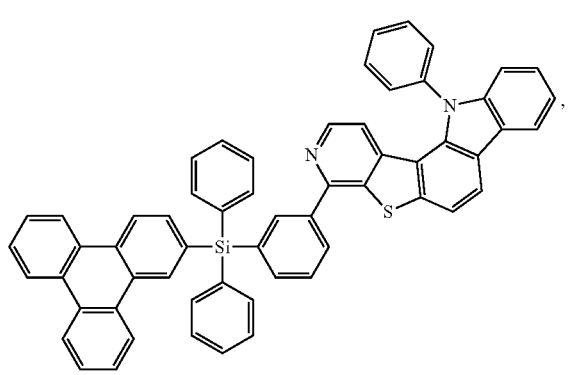

Compound 22

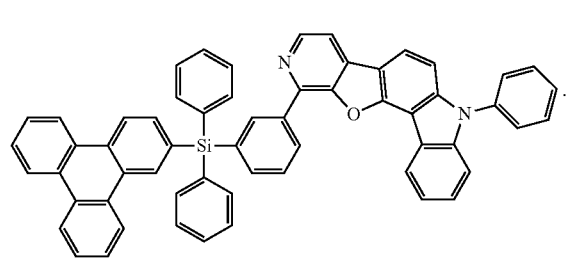

13. A first device comprising an organic light-emitting device, further comprising:
an anode;
a cathode; and
an organic layer, disposed between the anode and the cathode, comprising a compound having the formula:

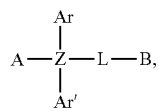

Formula I wherein Ar and Ar' are independently selected from the group consisting of phenyl, biphenyl, naphthalene, dibenzothiophene and dibenzofuran, which are optionally further substituted;
Z is selected from Si and Ge;
L is a single bond or comprises an aryl or heteroaryl group having from 5-20 carbon atoms, which is optionally further substituted;
A is a group directly bonded to Z and is selected from the group consisting of triphenylene, tetraphenylene, pyrene, naphthalene, fluoranthene, chrysene, phenanthrene, azatriphenylene, azatetraphenylene, azapyrene, azanaphthalene, azafluoranthene, azachrysene, azaphenanthrene, and combinations thereof, which are optionally further substituted with one or more groups selected from the group consisting of hydrogen, deuterium, halide, alkyl, cycloalkyl, heteroalkyl, arylalkyl, aryl, aryloxy, and combinations thereof;
B is a group selected from the group consisting of carbazole, dibenzoselenophene, aza-carbazole, aza-dibenzofuran, aza-dibenzothiophene, azadibenzoselenophene, and combinations thereof, which are optionally further substituted with one or more groups selected from hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein the substitution is optionally fused to the carbazole, dibenzoselenophene, aza-carbazole, aza-dibenzofuran, aza-dibenzothiophene or azadibenzoselenophene group
wherein when B is carbazole, the carbazole group is connected to L through a ring carbon.

14. The first device of claim 13, wherein the organic layer is an emissive layer and the compound of Formula I is a host.

15. The first device of claim 13, wherein the organic layer further comprises an emissive dopant.

16. The first device of claim 15, wherein the emissive dopant is a transition metal complex having at least one ligand selected from the group consisting of:

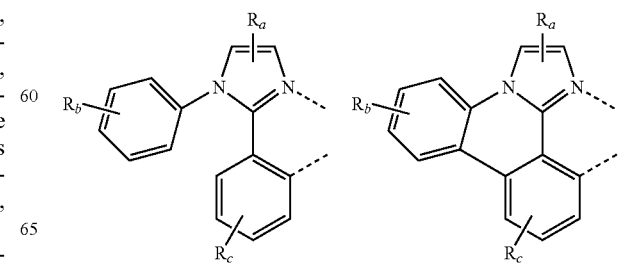

-continued

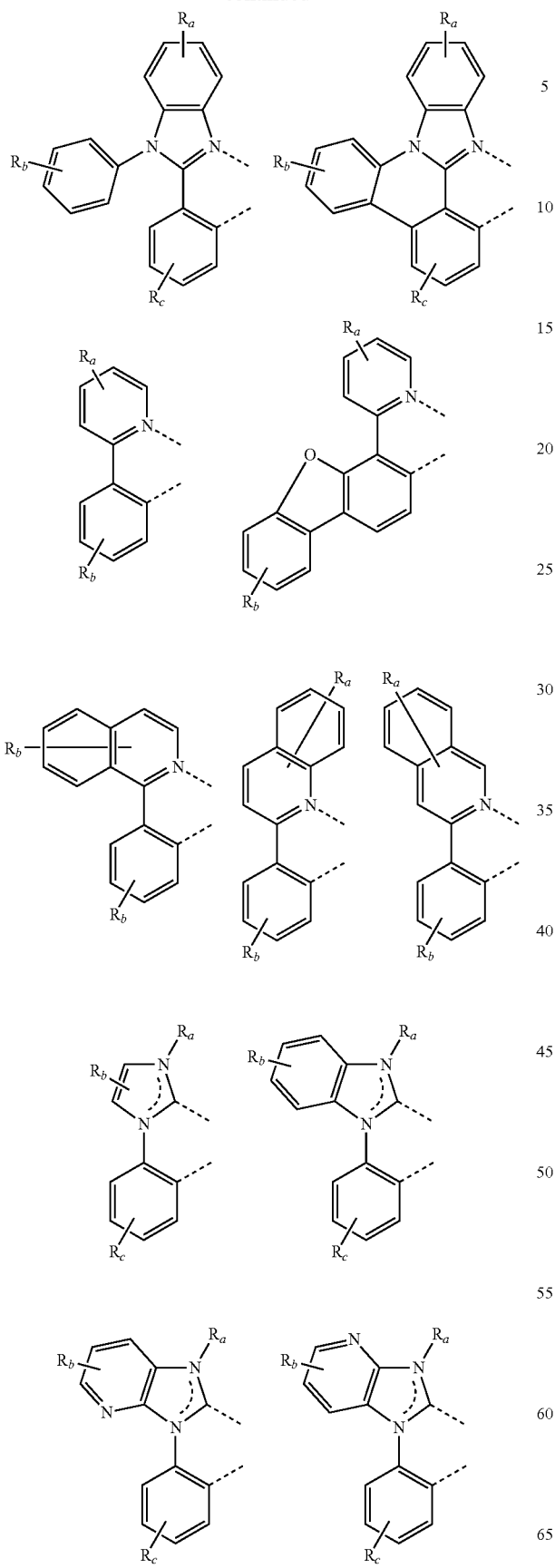

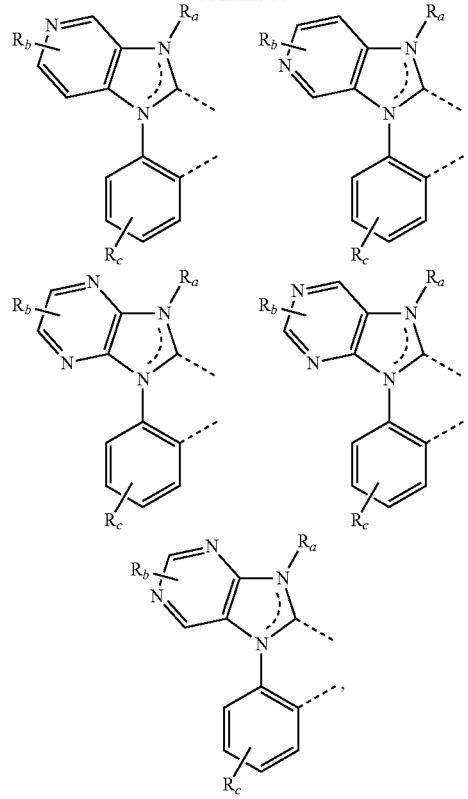

wherein $R_a$, $R_b$, and $R_c$ may represent mono, di, tri or tetra substitutions;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring.

17. The first device of claim 15, wherein the emissive dopant has the formula

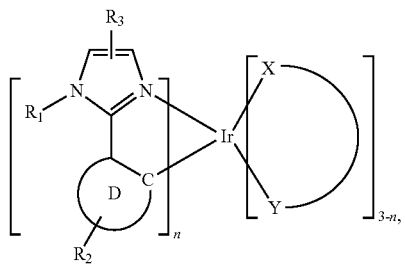

wherein D is a 5- or 6-membered carbocyclic or heterocyclic ring;

wherein $R_1$, $R_2$, and $R_3$ independently represent mono, di, tri or tetra substitution;

wherein each of $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R_1$ can be optionally linked to ring D;

wherein n is 1, 2, or 3; and wherein X—Y is another ligand.

18. The first device of claim 13, wherein the device further comprises a second organic layer that is a non-emissive layer and the compound having Formula I is a material in the second organic layer.

19. The first device of claim 18, wherein the second organic layer is a blocking layer and the compound having Formula I is a blocking material in the second organic layer.

20. The first device of claim 18, wherein the second organic layer is an electron transporting layer and the compound having the Formula I is an electron transporting material in the second organic layer.

21. The first device of claim 13, wherein the first device is a consumer product.

22. The first device of claim 13, wherein the first device is an organic light-emitting device.

23. The first device of claim 14, wherein the first device comprises a lighting panel.

* * * * *